United States Patent
Mukhopadhyay et al.

(10) Patent No.: US 11,901,078 B2
(45) Date of Patent: Feb. 13, 2024

(54) APPARATUS, SYSTEMS, AND METHODS FOR RAPID CANCER DETECTION

(71) Applicant: 4D Path Inc., Newton, MA (US)

(72) Inventors: Satabhisa Mukhopadhyay, Newton, MA (US); Tathagata Dasgupta, Newton, MA (US)

(73) Assignee: 4D Path Inc., Newton, MA (US)

( * ) Notice: Subject to any disclaimer, the term of this patent is extended or adjusted under 35 U.S.C. 154(b) by 0 days.

(21) Appl. No.: 17/506,192

(22) Filed: Oct. 20, 2021

(65) Prior Publication Data
US 2022/0037025 A1  Feb. 3, 2022

Related U.S. Application Data

(63) Continuation of application No. 16/688,910, filed on Nov. 19, 2019, now abandoned, which is a (Continued)

(51) Int. Cl.
*G06K 9/00* (2022.01)
*G16H 50/20* (2018.01)
(Continued)

(52) U.S. Cl.
CPC .......... *G16H 50/20* (2018.01); *G06T 7/0012* (2013.01); *G06T 7/10* (2017.01); *G06V 20/695* (2022.01); *G16H 10/40* (2018.01); *G16H 30/20* (2018.01); *G16H 30/40* (2018.01); *G16H 50/30* (2018.01); *G06T 2207/10024* (2013.01); *G06T 2207/10048* (2013.01); *G06T 2207/30004* (2013.01); *G06T 2207/30024* (2013.01)

(58) Field of Classification Search
None
See application file for complete search history.

(56) References Cited

U.S. PATENT DOCUMENTS 5,554,602 A  9/1996  Top et al.
5,912,165 A  6/1999  Cabib et al.
(Continued)

FOREIGN PATENT DOCUMENTS

WO   WO-2018/201072 A2   11/2018

OTHER PUBLICATIONS

Bellisola, G. and Sorio, C., Infrared spectroscopy and microscopy in cancer research and diagnosis, Am. J. Cancer Res. 2(1):1-21 (2012).
(Continued)

*Primary Examiner* — Wei Wen Yang
(74) *Attorney, Agent, or Firm* — Fish & Richardson P.C.

(57) ABSTRACT

Presented herein are systems, methods, and apparatus that analyze molecular imprints for detecting cancerous cells. Embodiments of the present disclosure include systems, methods, and apparatus that analyze metabolic imprints of cells for cancer detection. In certain embodiments, the methods/systems comprise extracting thermal and thermodynamic quantities and properties from the molecular imprints. The thermal/thermodynamic quantities and/or further-processed quantities can be mapped on a universal cancer diagnostic scale for disease stratification, thereby providing/determining a normality status of the subject cells.

21 Claims, 42 Drawing Sheets

Related U.S. Application Data continuation of application No. 15/965,664, filed on Apr. 27, 2018, now Pat. No. 10,535,434.

(60) Provisional application No. 62/491,774, filed on Apr. 28, 2017.

(51) Int. Cl.

| | | |
|---|---|---|
| *G16H 10/40* | (2018.01) | |
| *G06T 7/00* | (2017.01) | |
| *G16H 50/30* | (2018.01) | |
| *G06T 7/10* | (2017.01) | |
| *G16H 30/40* | (2018.01) | |
| *G16H 30/20* | (2018.01) | |
| *G06V 20/69* | (2022.01) | |

(56) References Cited

U.S. PATENT DOCUMENTS

| | | | |
|---|---|---|---|
| 6,876,760 | B1 | 4/2005 | Vaisberg et al. |
| 10,304,188 | B1 | 5/2019 | Kumar |
| 10,535,434 | B2 | 1/2020 | Mukhopadhyay et al. |
| 2002/0154798 | A1 | 10/2002 | Cong et al. |
| 2004/0042646 | A1 | 3/2004 | MacAulay et al. |
| 2004/0119020 | A1 | 6/2004 | Bodkin |
| 2006/0014238 | A1 | 1/2006 | Gholap et al. |
| 2006/0258018 | A1 | 11/2006 | Curl et al. |
| 2008/0045394 | A1 | 2/2008 | Kolenbrander et al. |
| 2009/0004647 | A1 | 1/2009 | Miura et al. |
| 2009/0042184 | A1 | 2/2009 | Mas et al. |
| 2011/0217713 | A1 | 9/2011 | Weaver et al. |
| 2012/0223804 | A1 | 9/2012 | Gaitas |
| 2012/0225475 | A1 | 9/2012 | Wagner et al. |
| 2012/0269418 | A1 | 10/2012 | McCulloch et al. |
| 2015/0003715 | A1 | 1/2015 | Tomoto et al. |
| 2015/0324997 | A1 | 11/2015 | Murakami |
| 2016/0231225 | A1* | 8/2016 | Hayden .................. G01N 15/10 |
| 2017/0116715 | A1 | 4/2017 | Takayama |
| 2017/0260590 | A1 | 9/2017 | Eltoukhy et al. |
| 2017/0266438 | A1* | 9/2017 | Sano .................. A61B 18/1477 |
| 2018/0103935 | A1 | 4/2018 | Pringle et al. |
| 2018/0239949 | A1 | 8/2018 | Chander et al. |
| 2018/0291459 | A1 | 10/2018 | Al-Deen Ashab et al. |
| 2018/0315506 | A1 | 11/2018 | Mukhopadhyay et al. |
| 2019/0113423 | A1 | 4/2019 | Goodman et al. |
| 2020/0090811 | A1 | 3/2020 | Mukhopadhyay et al. |

OTHER PUBLICATIONS

Draux, F. et al., IR spectroscopy reveals effect of non-cytotoxic doses of anti-tumour drug no cancer cells, Anal. Bioanal. Chem. 395:2293-2301 (2009).

Fernandez, D. C. et al., Infrared spectroscopic imaging for histopathologic recognition, Nature Biology, 23(4):469-474 (2005).

Gough, A. et al., Biologically Relevant Heterogeneity: Metrics and Practical Insights, SLAS Discovery, 22(3):213-237 (2017).

Gurcan, M. N. et al., Histopathological Image Analysis: A Review, IEEE Reviews in Biomedical Engineering, 2:147-171 (2009).

International Search Report, PCT/US2018/029995 (Apparatus, Systems, and Methods for Rapid Cancer Detection, filed Apr. 27, 2018), issued by ISA/European Patent Office, 7 pages, Nov. 16, 2018.

Isola, P. et al., Crisp Boundary Detection Using Pointwise Mutual Information, Medical image computing and computer-assisted intervention—MICCAI 2015: 18th International Conference, 18 pages, (2015).

Legrand, R. et al., Thermal microscopy of single biological cells, Applied Physics Letters, AIP Publishing LLC, 107(26):1-5 (2015).

Partial International Search Report, PCT/US2018/029995 (Apparatus, Systems, and Methods for Rapid Cancer Detection, filed Apr. 27, 2018), issued by ISA/European Patent Office, Jul. 27, 2018, 3 pages.

Provisional Opinion Accompanying the Partial Search Report, Apparatus, Systems, and Methods for Rapid Cancer Detection, filed Apr. 27, 2018), issued by ISA/European Patent Office, Jul. 27, 2018, 14 pages.

Ramoser, H., et al. Leukocyte segmentation and classification in blood-smear images, Engineering in medicine and biology society, 3371-3374, (2005).

Spagnolo, D. M. et al., Pointwise mutual information quantifies intratumor heterogeneity in tissue sections labeled with multiple fluorescent biomarkers, Journal of Pathology Informatics, 1:47, 18 pages, (2016), retrieved from internet: URL:http://www.jpathinformatics.org/temp/JPatholInform7147-2857576.pdf, [retrieved Jun. 27, 2018].

Written Opinion, PCT/US2018/029995 (Apparatus, Systems, and Methods for Rapid Cancer Detection, filed Apr. 27, 2018), issued by ISA/European Patent Office, 20 pages, Nov. 16, 2018.

healthcare-in-europe.com [online], "Medtronic—O-arm—Mobile Surgical Imaging System," Mar. 3, 2015, retrieved on Apr. 25, 2022, retrieved from URL <http://www.healthcare-in-europe.com/en/article/14083-medtronic-o-arm-mobile-surgical-imaging-system.html>, 9 pages.

International Preliminary Report on Patentability in International Appln. No. PCT/US2018/029995, dated Nov. 7, 2019, 22 pages.

Pijanka et al., "Spectroscopic signatures of single, isolated cancer cell nuclei using synchrotron infrared microscopy," Analyst, Mar. 2009, Issue 6, 134, 1176-1181.

smith-nephew.com [online], "LENS: Surgical Imaging System," available on or before Jul. 14, 2016, via Internet Archive: Wayback Machine URL <https://web.archive.org/web/20160714074525/https://www.smith-nephew.com/professional/products/all-products/lens/>, retrieved on Apr. 25, 2022, retrieved from URL <http://www.smith-nephew.com/professional/products/all-products/lens/>, 2 pages.

* cited by examiner

11 - Cancerous tissue, (12,13,14) - curved mirrors, a,b,c,d,g,h - Signal from cancerous tissue, 15 - 2D FDA IR Detector, 17 - Signal processing module (FPGA with algorithm), 18 - Memory, 19 - inference 21 - Cancerous tissue/ensembles of cells, 22 - Relay Optics, 23, 24 - Signal from cancerous tissue, 25 - 2D FPA IR Detector

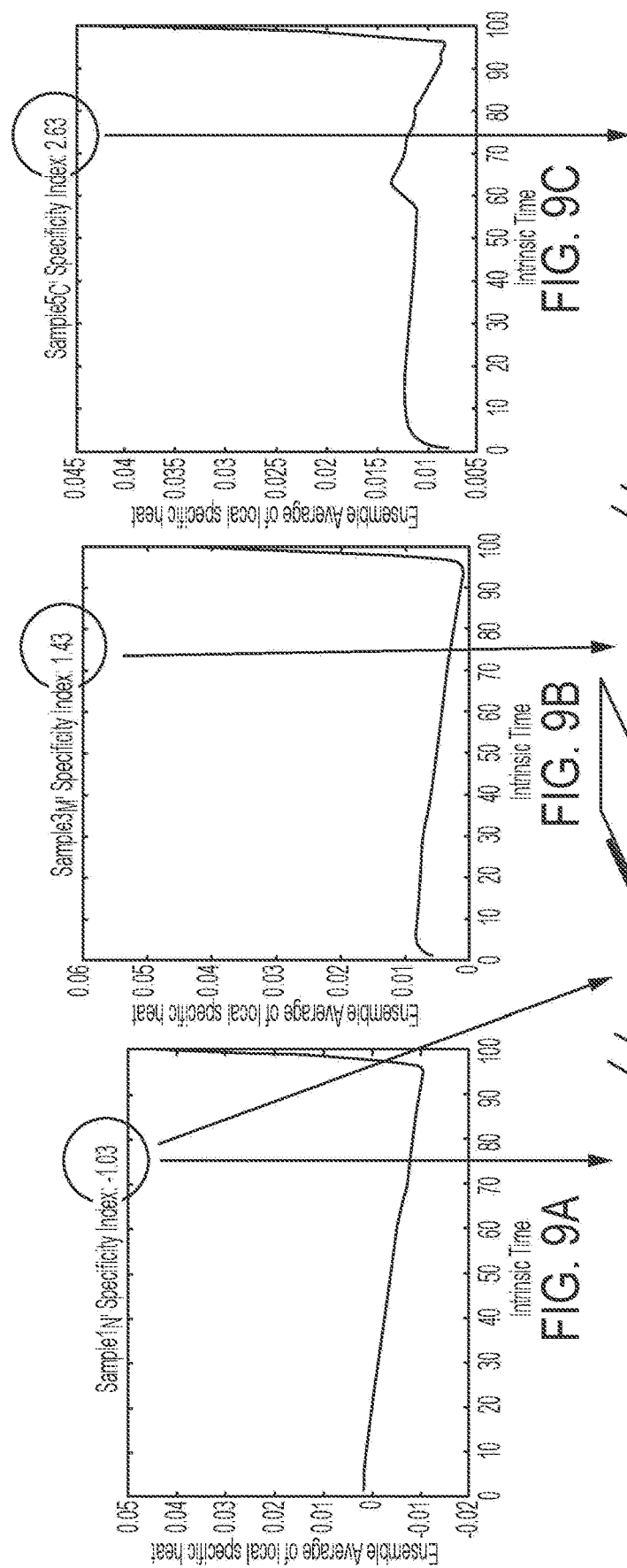
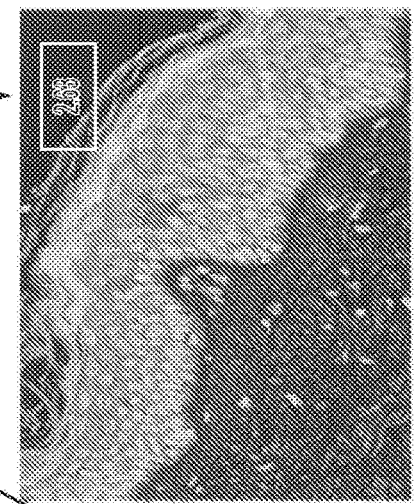
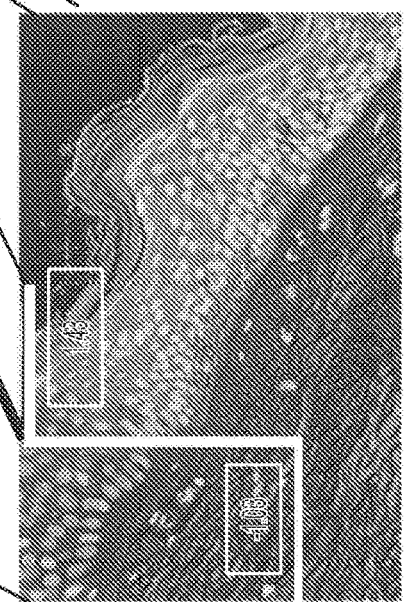
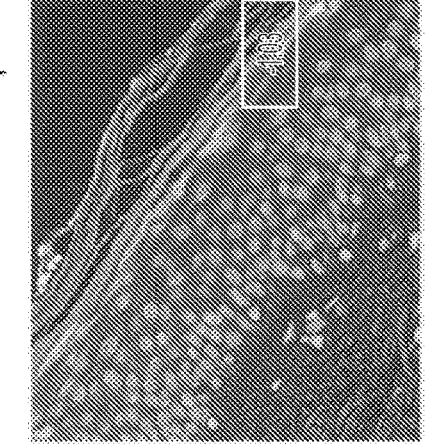
FIG. 9A FIG. 9B FIG. 9C
FIG. 9D FIG. 9E FIG. 9F

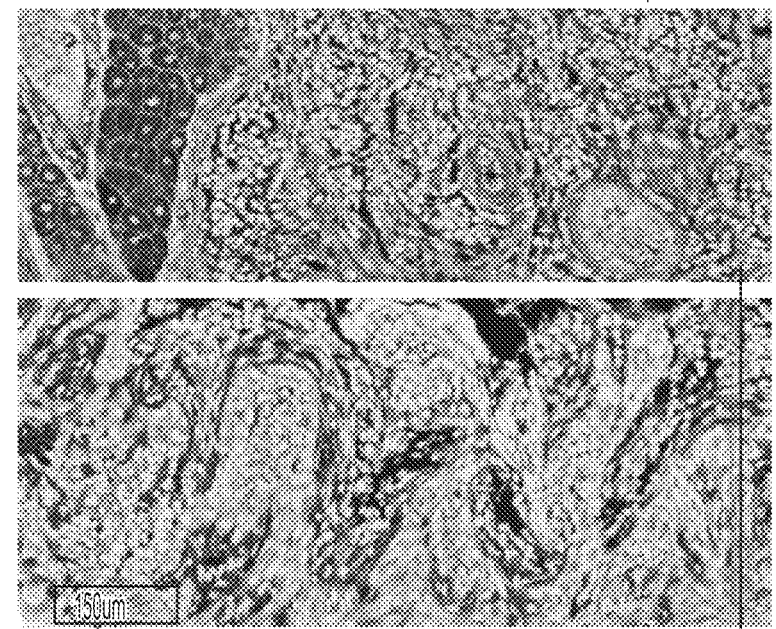
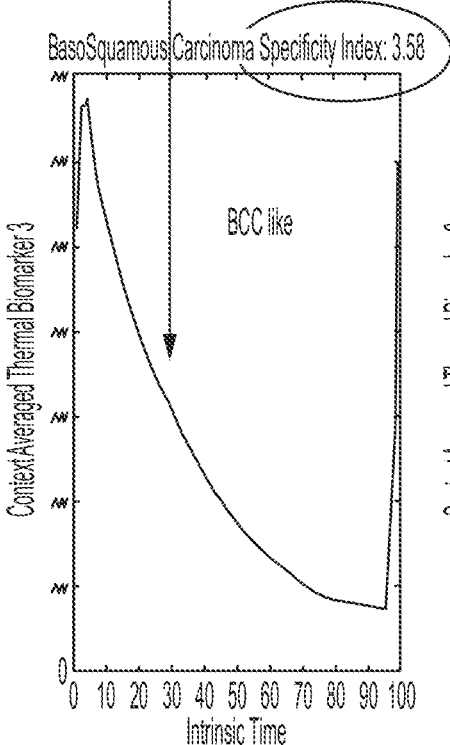
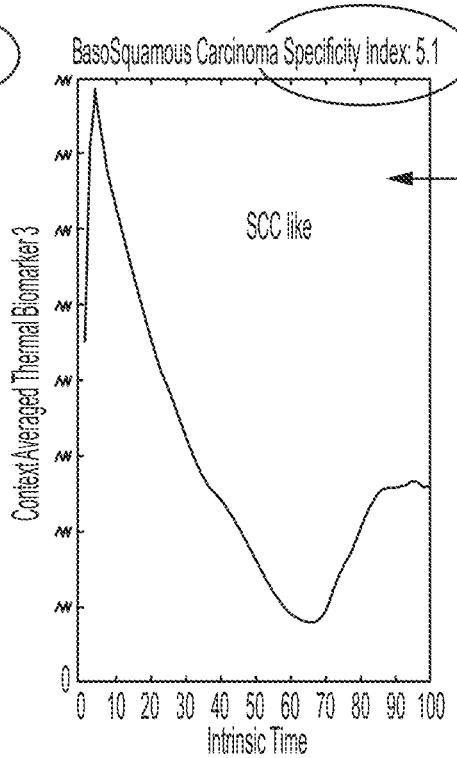
FIG. 11B

Subtle Cases and Melanoma Look-alikes
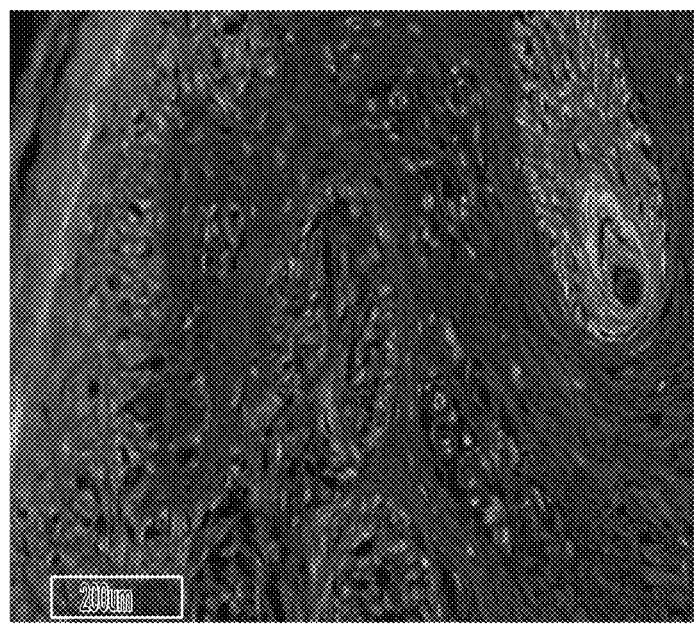
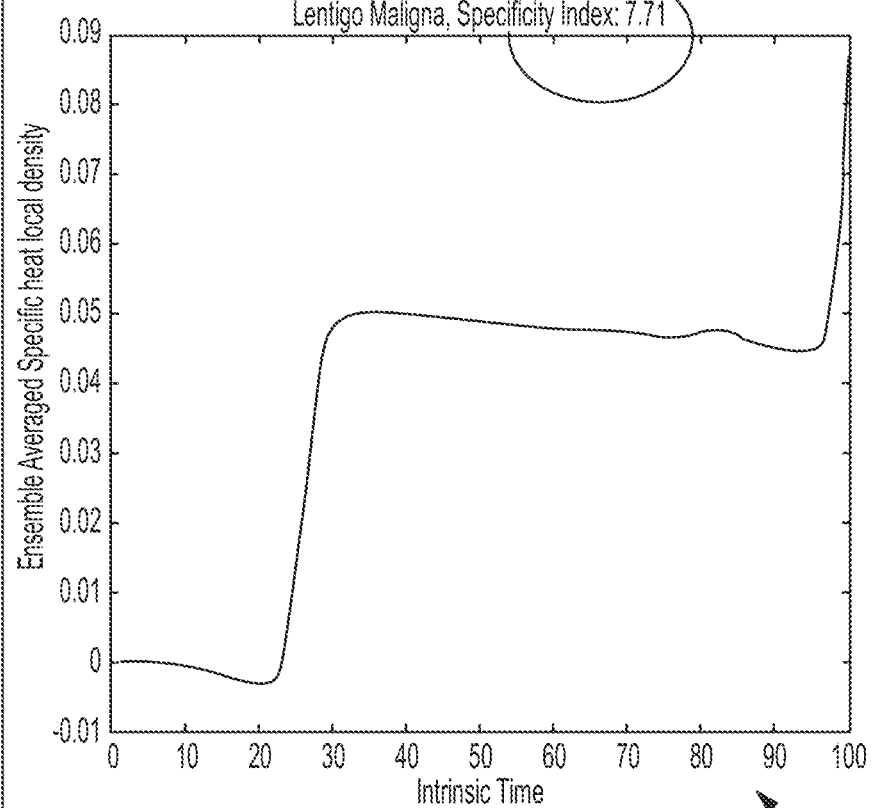
FIG. 11C

Actinic Keratosis

Bowen's Disease

SCC in-situ

SCC Poorly Differentiated

SCC Medium Differentiated

SCC Well Differentiated

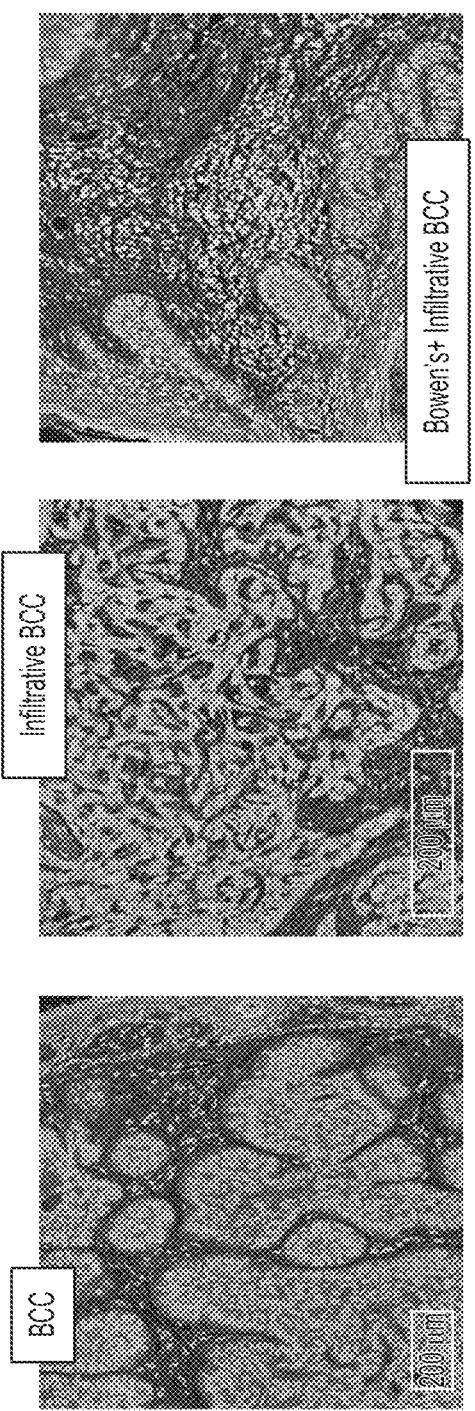
FIG. 15A BCC
FIG. 15B Infiltrative BCC
FIG. 15C Bowen's + Infiltrative BCC
FIG. 15D Superficially Spreading BCC
FIG. 15E Nodular BCC 93 - proposed device, 94 - skin lesion to be tested, 9- test subject (human mouth)

90 - proposed device, 91 - skin lesion to be tested, 92- test subject (hand)

104 - proposed device, 105 - skin lesion to be tested, 106 - test subject, φ & θ - of rotation of the detector, r - radial distance of the detector from the body, I, II - direction of rotation 100 - proposed device, 101,102 - skin lesion to be tested, 103 - test subject pat 110 - Human subject (patient), 111 - Colon, 112 - Hollow tube, 113 - Cancerous tissue/skin lesion/polyp to be tested, 114 - 2D FPA iR Detector, 115 - Relay Optics (Transmission or/and Reflective), 116 - Signal from cancerous tissue, 117 - Signal from detector, 121, 122, 123 - additional colonoscopy channels, 119 - Signal processing module (FPGA with algorithm), 120 - memory 130 - Human subject (patient), 131 - breast, 132 - Cancerous tumor to be tested, 133 - Hollow surgical needle (with or without additional channels), 134 - Hollow tube, 135 - Relay Optics (Transmission and/or Reflective), 136 - Signal from cancerous breast tumor, 137 - 2D FPA IR detector, 138 - Signal processing module (FPGA with algorithm), 139 - Memory, 140 - inference 150 - Relay Optics (Transmission and/or Reflective), m, n - signal from cells/tissue, 151 - 2D detector, 152 - Signal processing module (FPGA with algorithm), 153 - Memory, 154 - inference, A,C - zones of healthy tissue, B - zones of cancerous tissue, 156 - direction of scan

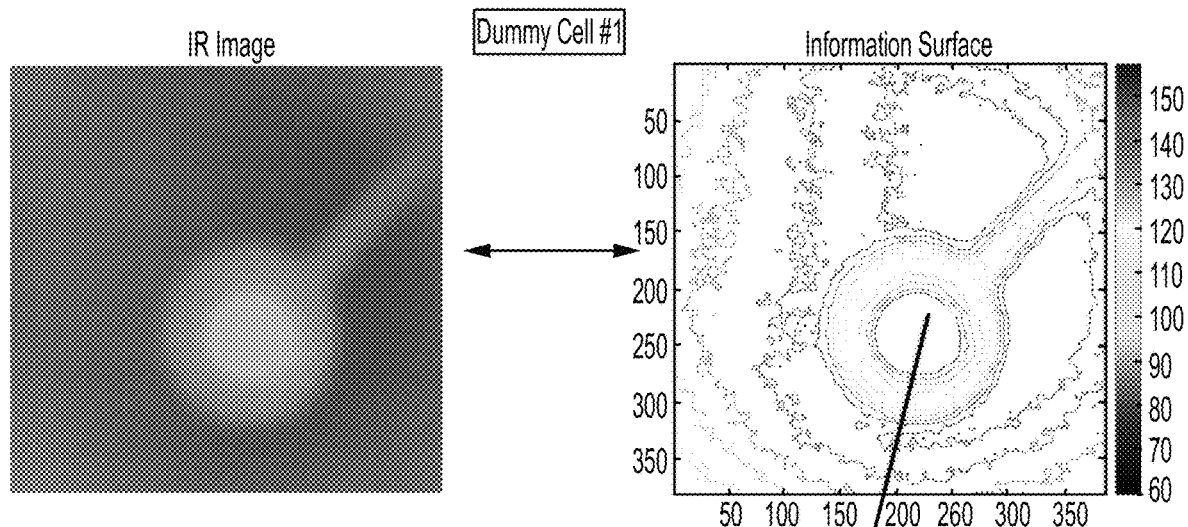
FIG. 32A
FIG. 32B
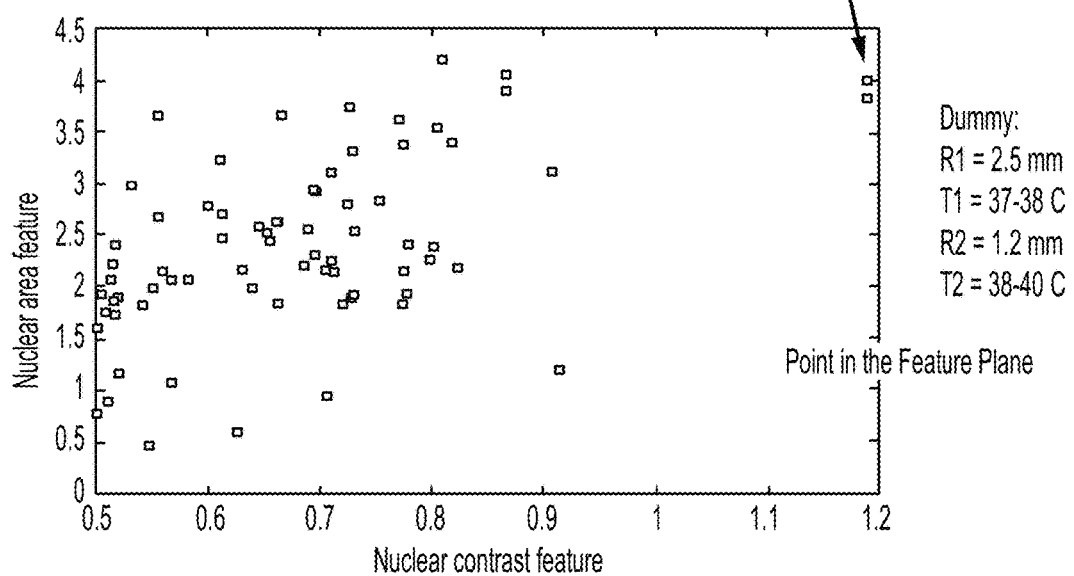
FIG. 32C

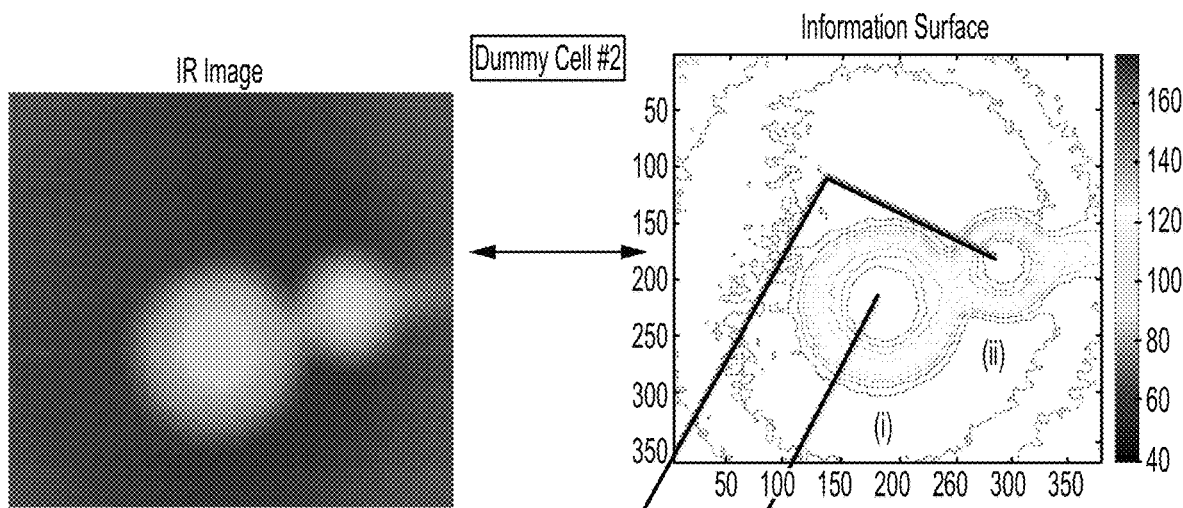
FIG. 33A
FIG. 33B
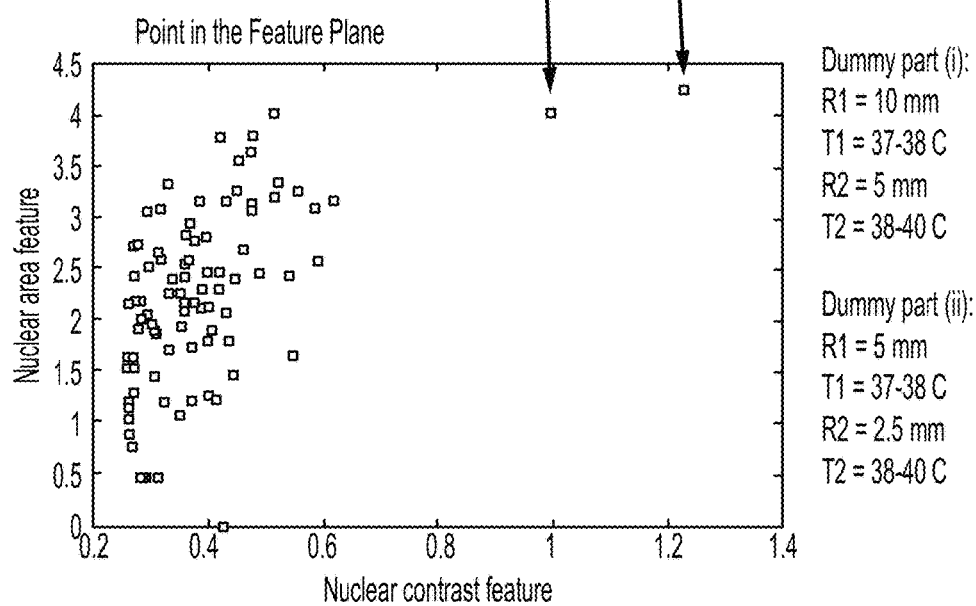
FIG. 33C

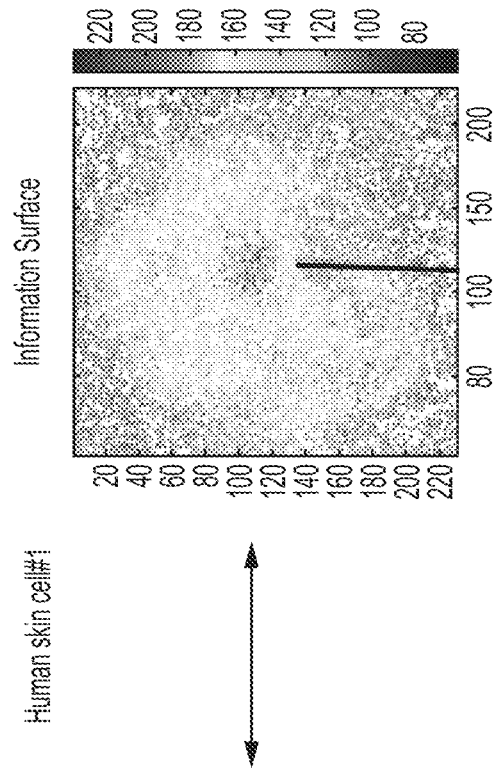
FIG. 34A
FIG. 34B
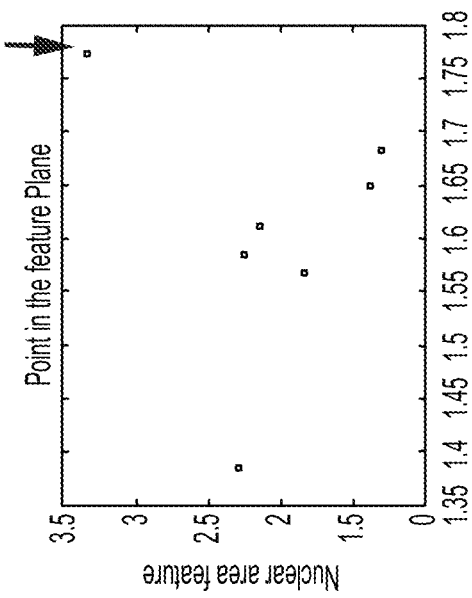
FIG. 34C

APPARATUS, SYSTEMS, AND METHODS FOR RAPID CANCER DETECTION

CROSS REFERENCE TO RELATED APPLICATIONS

This application is a continuation of U.S. patent application Ser. No. 16/688,910 filed on Nov. 19, 2019, which is a continuation of U.S. patent application Ser. No. 15/965,664 filed on Apr. 27, 2018 and granted as U.S. Pat. No. 10,535,434, and claims the benefit of U.S. Provisional Patent Application No. 62/491,774 filed on Apr. 28, 2017.

TECHNICAL FIELD

The invention relates generally to methods, systems, and apparatus for cancer detection.

BACKGROUND

Cancer has traditionally been viewed as a genetic disease. In 1924, Otto Warburg pointed out that cancer could be understood as a metabolic disease originated by damage of a cell's capacity to generate energy with oxygen, i.e., respiratory insufficiency. When mitochondria of a cell have a certain degree of damage, and the cell shifts energy production to non-oxidative metabolism to obtain energy, cancer has begun. However, the metabolic theory of cancer was mostly discarded when it was reported that cancer cells have mutations to deoxyribonucleic acid (DNA). Recently, many phenotypes and manifestations of cancers, including diverse somatic mutations (e.g., mutations in genes controlling cell division), are discovered to be caused directly or indirectly from insufficient respiration. A direct translation of these altered metabolic imprints has been observed in increased cell proliferations at different cell cycle stages.

Most current cancer detection methods are developed for specific types or subtypes of cancers. The detection methods are typically dependent on specific molecular signatures, for example, phenotype biomarkers. These methods sometimes lack specificity, because the methods detect nonspecific signals (e.g., bulk imaging/tomography for picking up nonspecific shadows as tumors), which often do not have a direct connection to specific cancers. Furthermore, current methods compromise detection sensitivity, as a specific molecular signal for a certain type of cancer is much weaker than the background signal from all other molecular interaction (e.g., which is not the specific molecular signal). Thus, there is a need for improved methods, systems and apparatus for detecting cancer with high specificity and sensitivity, contained therein.

SUMMARY

Described herein are various systems, methods, and apparatus for cancer detection. In certain embodiments, the present invention relates to methods and/or systems for analyzing molecular imprints for detecting cancerous cells.

The methods and systems herein address shortcomings associated with prior strategies for detecting cancer. Embodiments of the present disclosure include methods, systems and apparatus that analyze metabolic imprints of cells for cancer detection. In certain embodiments, the methods/systems comprise extracting thermal and thermodynamic quantities and properties from the molecular imprints (e.g., from naturally emitted infrared radiations (IR) of cells/tissues). The thermal/thermodynamic quantities and/or further-processed quantities (e.g., specificity index, diagnostic score) can be mapped on a universal cancer diagnostic scale for disease stratification, thereby providing/determining a normality status of the subject cells, for example.

In one aspect, the invention is directed to a method for detecting one or more types of cancers (e.g., deciding a normality status, e.g., subtle cases of cancers) from metabolic imprints of cells, which comprises (i) accessing an image in a database, (ii) identifying, by a processor, of a computing device, one or more cells in the image, (iii) segmenting, by the processor, each of the one more cells into a nucleus area and a cellular area, (iv) for each of the one or more cells, extracting, by the processor, an information surface value associated with a nuclear contrast feature (e.g., temperature difference between the nucleus area and the cellular area, e.g., contrast difference between the nucleus area and the cellular area), and a nuclear area feature (e.g., a ratio of a nucleus area to a nuclear volume projection), (v) calculating, by the processor, a specificity index, a log thermal capacity or a diagnostic score from the information surface values, and (vi) determining, by the processor, a normality status for at least a portion of the image by mapping the specificity index on a reference scale (e.g., identifying one or more portions of the cells in the image that are cancerous, and/or identifying one or more stages of cancer for one or more portions of the cells in the image). In certain embodiments, the method comprises selecting an area to be analyzed in the image.

In certain embodiments, the specificity index is determined by (1) calculating each of an ensemble average of local specific heats for each of subpopulations of cells (e.g., wherein the subpopulations of cells are decided by the information surface values) (e.g., each of the subpopulations of cells corresponds to different cell cycle stages and/or different intrinsic cell cycle time), and (2) integrating the ensemble average of local specific heats over cell cycle stages or intrinsic cell cycle time.

In certain embodiments, the log thermal capacity is calculated by integrating logarithm of local specific heats for each of subpopulations of cells.

In certain embodiments, the diagnostic score is $$\frac{\text{Specificity Index}}{\text{shape feature}} \text{ or }$$

$$\frac{\Pi_i \text{ Shape } feature_i \times \text{Log Thermal Capacity}}{\text{Specificity Index}},$$

wherein the shape feature represents a shape of a piecewise curve, wherein the piecewise curve is a curve of intrinsic cell cycle time vs the specificity index, or a curve of the intrinsic cell cycle time vs the log thermal capacity, wherein the shape feature is selected from the group consisting of a number of subsections in the piecewise curve, a value of the intrinsic cell cycle time at one or more junctions in the piecewise curve, a curvature at the junction of the subsections the piecewise curve and combinations thereof, and wherein i is an integer and i>0.

In certain embodiments, the image is produced from a long wavelength infrared radiation (IR) (e.g., naturally emitted IR from one or more cells, e.g., having a wavelength of 3 μm to 20 μm, e.g., having a wavelength of 8 μm to 14 μm) detector. In certain embodiments, the long wavelength infrared radiation detector is operated at room temperature (e.g., 15° C. to 25 ° C.). In certain embodiments, the long wavelength infrared radiation detector is operated at physiological temperature (e.g., 35° C. to 38° C.). In certain embodiments, the long wavelength infrared radiation detector is operated at a temperature of below 15° C. (e.g., below 10° C., below 5° C.).

In certain embodiments, the nuclear contrast feature and/or the nuclear area feature are obtained at a wavelength corresponding to a maximal radiant power of the naturally emitted IR from one or more cells. In certain embodiments, the nuclear contrast feature is an averaged value of one or more nuclear contrast features obtained at one or more wavelengths of naturally emitted IR from one or more cells. In certain embodiments, the nuclear area feature is an averaged value of one or more nuclear area features obtained at one or more wavelengths of the naturally emitted IR from one or more cells.

In certain embodiments, the specificity index is calculated by (1) calculating each of ensemble average of local specific heats for each of subpopulations of cells and (2) integrating the ensemble averaged local specific heat over cell cycle stages or intrinsic cell cycle time. In certain embodiments, the subpopulations of cells are decided by the information surface values. In certain embodiments, each of the subpopulations of cells corresponds to different cell cycle stages and/or different intrinsic cell cycle time.

In certain embodiments, the method further comprises one or more of (vii) to (xi) as follows: (vii) objectively auto-detecting, by the processor, one or more of (a) to (c) as follows: (a) cancer rare subpopulations, (b) subtle mimics, and/or (c) look alike cases (that are normally difficult to diagnose by human eye and thus an extremely hard goal to be achieved by machine learning and AI techniques requiring lots of training data where the training data, to start with is provided by human experts), (viii) following step (vii), extracting, by the processor, prognostic features comprising (including but not limited to) differentiation status and grade of the disease, and (ix) determining, by the processor, progression of disease and its possible regression after therapy/drug treatment from evolution of the diagnostic features and indices, such as the specificity index, from the (temporally) longitudinal data, (x) determining, by the processor, in real time, efficacy of cancer drug treatment from (temporally) longitudinal data; and (xi) detecting, by the processor, drug resistant subpopulations (that are often left unnoticed and cause the disease to recur).

In certain embodiments, the image is an H&E stained image.

In certain embodiments, the one or more types of cancers are rare subpopulations, subtle mimics or look-alike cases. In certain embodiments, the one or more types of cancers are difficult to be diagnosed by human eye and/or require machine learning.

In certain embodiments, the method comprises refining the normality status using a pre-trained machine learning technique.

In certain embodiments, the method comprises further determining, by the processor, a prognostic feature (e.g., a disease state or grade) based at least in part on the specificity index.

In certain embodiments, the method further comprises selecting an area to be analyzed in the image, wherein the area comprises at least two adjacent sections, repeating the steps of (i)-(v) for each of the at least two adjacent sections; and deciding if the area comprises a cancer boundary by comparing normality statuses of the two adjacent sections (e.g., wherein two adjacent sections of the cancer boundary have different stages of cancer).

In certain embodiments, the method comprises providing one or more therapeutic treatments to a subject or a sample (e.g., cell culture from a subject), repeating steps (i)-(v); and comparing the normality status before the one or more therapeutic treatments and the normality status after the one or more therapeutic treatments.

In certain embodiments, the steps of repeating and comparing are performed periodically to monitor an effect of the one or more therapeutic treatments.

In certain embodiments, the method determines the normality status substantially in real-time (e.g., using a field-programmable gate array (FPGA)).

In another aspect, the invention is directed to a system for detecting one or more types of cancers (e.g., deciding a normality status) from metabolic imprints of cells, which comprises a processor, a memory having instructions stored thereon, wherein the instructions, when executed by the processor, cause the processor to perform operations comprising (i) accessing an image in a database, (ii) identifying one or more cells in the image, (iii) segmenting each of the one more cells into a nucleus area and a cellular area, (iv) for each of the one or more cells, extract an information surface value associated with a nuclear contrast feature (e.g., temperature difference between the nucleus area and the cellular area, e.g., contrast difference between the nucleus area and the cellular area), and a nuclear area feature (e.g., a ratio of a nucleus area to a nuclear volume projection), (v) calculating a specificity index or a diagnostic score from the information surface values, and (vi) determining a normality status for at least a portion of the image by mapping the specificity index on a reference scale (e.g., identifying one or more portions of the cells in the image that are cancerous, and/or identifying one or more stages of cancer for one or more portions of the cells in the image.

In certain embodiments, the instructions, when executed by the processor, cause the processor to perform operations comprising selecting an area to be analyzed in the image.

In certain embodiments, the nuclear contrast feature and/or the nuclear area feature are obtained at a wavelength corresponding to a maximal radiant power of the naturally emitted IR from one or more cells. In certain embodiments, the nuclear contrast feature is an averaged value of one or more nuclear contrast features obtained at one or more wavelengths of naturally emitted IR from one or more cells. In certain embodiments, the nuclear area feature is an averaged value of one or more nuclear area features obtained at one or more wavelengths of the naturally emitted IR from one or more cells.

In certain embodiments, In certain embodiments, the specificity index is calculated by calculating each of ensemble average of local specific heats for each of the subpopulations of cells, and (2) integrate the ensemble averaged local specific heat over cell cycle stages or intrinsic cell cycle time. In certain embodiments, the subpopulations of cells are decided by the information surface values. In certain embodiments, each of the subpopulations of cells corresponds to different cell cycle stages and/or different intrinsic cell cycle time.

In certain embodiments, the instructions, when executed by the processor, cause the processor to perform operations further comprising one or more of (vii) to (xi) as follows: (vii) objectively auto-detecting, by the processor, one or more of (a) to (c) as follows: (a) cancer rare subpopulations, (b) subtle mimics, and/or (c) look alike cases (that are normally difficult to diagnose by human eye and thus an extremely hard goal to be achieved by machine learning and AI techniques requiring lots of training data where the training data, to start with is provided by human experts), (viii) following step (vii), extracting, by the processor, prognostic features comprising (including but not limited to) differentiation status and grade of the disease, (ix) determining, by the processor, progression of disease and its possible regression after therapy/drug treatment from evolution of the diagnostic features and indices, such as the specificity index, from the (temporally) longitudinal data, (x) determining, by the processor, in real time, efficacy of cancer drug treatment from (temporally) longitudinal data, and (xi) detecting, by the processor, drug resistant subpopulations (that are often left unnoticed and cause the disease to recur).

In certain embodiments, the system comprises a long wavelength infrared radiation (e.g., naturally emitted IR from one or more cells, e.g., having a wavelength of 6 μm to 12 μm) detector (e.g., wherein the detector does not need a light source). In certain embodiments, the image is produced from the long wavelength infrared radiation (IR) detector.

In certain embodiments, the image is an H&E stained image.

In certain embodiments, the one or more types of cancers are rare subpopulations, subtle mimics or look-alike cases. In certain embodiments, the one or more types of cancers are difficult to be diagnosed by human eye and/or require machine learning.

In certain embodiments, the instructions, when executed by the processor, cause the processor to perform operations further comprising refining the normality status using a pre-trained machine learning technique.

In certain embodiments, the instructions, when executed by the processor, cause the processor to perform operations further comprising further determining a disease state based at least in part on the specificity index.

In certain embodiments, the instructions, when executed by the processor, cause the processor to perform operations further comprising selecting an area to be analyzed in the image, wherein the area comprises at least two adjacent sections, repeating steps (ii)-(v) for each of the at least two adjacent sections, and deciding if the area comprises a cancer boundary by comparing normality statuses of the two adjacent sections. In certain embodiments, two adjacent sections of the cancer boundary have different stages of cancer.

In certain embodiments, the instructions, when executed by the processor, cause the processor to perform operations further comprising providing one or more therapeutic treatments to a subject or a sample (e.g., cell culture from a subject), repeating steps (i)-(v), and comparing the normality status diagnosed before the one or more therapeutic treatments and after one or more therapeutic treatments.

In certain embodiments, steps repeating and comparing are performed periodically to monitor an effect of the one or more therapeutic treatments.

In certain embodiments, the system determines the normality status substantially in real-time (e.g., using a field-programmable gate array (FPGA)).

In another aspect, an apparatus for creating a long wavelength infrared image for detecting one or more types of cancers, which comprises a spatial magnification module providing an optical path, an infrared radiation detector for detecting long wavelength infrared radiation emitted from a subject (e.g., measuring photon flux), a signal processing module, and a memory, the signal processing module operable with the memory to record a signal corresponding to infrared radiation detected by the infrared radiation detector and to cause rendering of an image corresponding to the signal. In certain embodiments, the long wavelength infrared IR is naturally emitted IR from one or more cells, or has a wavelength of 4 μm to 20 μm. In certain embodiments, the spatial magnification module has a resolution of 20 microns or less. In certain embodiments, the detector comprises a focal-plane array, comprising a vanadium oxide surface, and/or comprising a mercury cadmium telluride surface. In certain embodiments, the image is 1-dimensional, 2-dimensional, 3-dimensional. In certain embodiments, the apparatus is operable to measure photon flux from the subject. In certain embodiments, the apparatus is operable without an external light source. In certain embodiments, the apparatus further comprises a heat source for enhancing the infrared radiation emitted from the subject. In certain embodiments, the apparatus is operable to produce the long wavelength infrared radiation image in any one of the preceding claims.

In certain embodiments, the signal processing module comprises a field-programmable gate array (FPGA).

In certain embodiments, the apparatus comprises an attachment locating the infrared radiation detector nearby (e.g., within 10 cm, 5 cm or 1 cm) an area (e.g., internal sites of human) to be diagnosed. In certain embodiments, the attachment is a biopsy needle.

In certain embodiments, the spatial magnification module comprises a first biconvex lens having a first focal length (f1), a second biconvex lens having a second focal length (f2), and a third biconvex lens having a third focal length (f3). In certain embodiments, a distance between the object and the first biconvex lens is no less than f1 (e.g., f1 is in range from 1 mm to 5 mm), so that the first biconvex lens generates a first magnified image (e.g., a real inverted magnified image) of the subject. In certain embodiments, a distance between the first biconvex lens and the first magnified image is no less than 2*f1. In certain embodiments, a distance between the first magnified image and the second biconvex lens is less than f2. In certain embodiments, the second biconvex lens re-magnifies the first magnified image, thereby generating a second magnified image. In certain embodiments, the third biconvex lens focuses the second magnified image on the infrared radiation detector. In certain embodiments, the spatial magnification module further comprises an aperture for filtering the naturally emitted IR.

In certain embodiments, the spatial magnification module comprises a convex mirror, a concave mirror, and a flat mirror. In certain embodiments, the convex mirror and the concave mirror are substantially concentric. In certain embodiments, a reflective surface of the convex mirror faces a reflective surface of the concave mirror. In certain embodiments, the concave mirror comprises on opening, so that a reflected radiation from the convex mirror passes through the opening. In certain embodiments, the opening is located on the optical path.

In another aspect, the invention is directed to a handheld diagnostic imaging device for performing one or more of the methods provided herein, which comprises relay optics (e.g., transmission and/or reflective optics) for transmitting a signal from a biological sample (e.g., in vivo, in vitro, or ex vivo) to a detector, the detector (e.g., a 2-D detector), a signal processing module (e.g., FPGA running algorithm) and a memory for processing a signal received from the detector, and optionally, a display for providing a diagnostic result determined by the signal processing module.

Elements of embodiments involving one aspect of the invention (e.g., methods) can be applied in embodiments involving other aspects of the invention, and vice versa.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "cancer" refers to a disease, disorder, or condition in which cells exhibit relatively abnormal, uncontrolled, and/or autonomous growth, so that they display an abnormally elevated proliferation rate and/or aberrant growth phenotype characterized by a significant loss of control of cell proliferation. In some embodiments, a cancer is characterized by one or more tumors. Those skilled in the art are aware of a variety of types of cancer including, for example, adrenocortical carcinoma, astrocytoma, basal cell carcinoma, carcinoid, cardiac, cholangiocarcinoma, chordoma, chronic myeloproliferative neoplasms, craniopharyngioma, ductal carcinoma in situ, ependymoma, intraocular melanoma, gastrointestinal carcinoid tumor, gastrointestinal stromal tumor (GIST), gestational trophoblastic disease, glioma, histiocytosis, leukemia (e.g., acute lymphoblastic leukemia (ALL), acute myeloid leukemia (AML), chronic lymphocytic leukemia (CLL), chronic myelogenous leukemia (CML), hairy cell leukemia, myelogenous leukemia, myeloid leukemia), lymphoma (e.g., Burkitt lymphoma [non-Hodgkin lymphoma], cutaneous T-cell lymphoma, Hodgkin lymphoma, mycosis fungoides, Sezary syndrome, AIDS-related lymphoma, follicular lymphoma, diffuse large B-cell lymphoma), melanoma, merkel cell carcinoma, mesothelioma, myeloma (e.g., multiple myeloma), myelodysplastic syndrome, papillomatosis, paraganglioma, pheochromacytoma, pleuropulmonary blastoma, retinoblastoma, sarcoma (e.g., Ewing sarcoma, Kaposi sarcoma, osteosarcoma, rhabdomyosarcoma, uterine sarcoma, vascular sarcoma), Wilms' tumor, and/or cancer of the adrenal cortex, anus, appendix, bile duct, bladder, bone, brain, breast, bronchus, central nervous system, cervix, colon, endometrium, esophagus, eye, fallopian tube, gall bladder, gastrointestinal tract, germ cell, head and neck, heart, intestine, kidney (e.g., Wilms' tumor), larynx, liver, lung (e.g., non-small cell lung cancer, small cell lung cancer), mouth, nasal cavity, oral cavity, ovary, pancreas, rectum, skin, stomach, testes, throat, thyroid, penis, pharynx, peritoneum, pituitary, prostate, rectum, salivary gland, ureter, urethra, uterus, vagina, or vulva.

As used herein the term "detector" includes any detector of electromagnetic radiation including, but not limited to, CCD camera, photomultiplier tubes, photodiodes, and avalanche photodiodes.

Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

As used herein, "diagnosis" refers to providing any type of diagnostic information, including, but not limited to, whether a subject is likely to have or develop a disease, disorder or condition, state, staging or characteristic of a disease, disorder or condition as manifested in the subject, information related to the nature or classification of a tumor, information related to prognosis and/or information useful in selecting an appropriate treatment. Selection of treatment may include the choice of a particular therapeutic agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc.

As used herein, the term "electromagnetic radiation" or "radiation" is understood to mean self-propagating waves in space of electric and magnetic components that oscillate at right angles to each other and to the direction of propagation, and are in phase with each other. Electromagnetic radiation includes: radio waves, microwaves, red, infrared, and near-infrared light, visible light, ultraviolet light, X-rays and gamma rays.

As used herein, the term "genotype" refers to the diploid combination of alleles at a given genetic locus, or set of related loci, in a given cell or organism. A homozygous subject carries two copies of the same allele and a heterozygous subject carries two distinct alleles. In the simplest case of a locus with two alleles "A" and "a", three genotypes can be formed: A/A, A/a, and a/a.

As used herein, an "image"—for example, a 3-D image of mammal—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

The term "in vitro" as used herein refers to events that occur in an artificial environment, e.g., in a test tube or reaction vessel, in cell culture, etc., rather than within a multi-cellular organism.

The term "in vivo" as used herein refers to events that occur within a multi-cellular organism, such as a human and a non-human animal. In the context of cell-based systems, the term may be used to refer to events that occur within a living cell (as opposed to, for example, in vitro systems).

As used herein, the term "map" is understood to mean a visual display, or any data representation that may be interpreted for visual display, which contains spatially-correlated information. For example, a three-dimensional map of a given volume may include a dataset of values of a given quantity that varies in three spatial dimensions throughout the volume. A three-dimensional map may be displayed in two-dimensions (e.g., on a two-dimensional screen, or on a two-dimensional printout).

As used herein, the term "phenotype" refers to a trait, or to a class or set of traits displayed by a cell or organism. In some embodiments, a particular phenotype may correlate with a particular allele or genotype. In some embodiments, a phenotype may be discrete; in some embodiments, a phenotype may be continuous.

As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

As used herein, the term "sample" typically refers to an aliquot of material obtained or derived from a source of interest, as described herein. In some embodiments, a source of interest is a biological or environmental source. In some embodiments, a source of interest may be or comprise a cell or an organism, such as a microbe, a plant, or an animal (e.g., a human). In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., brocheoalvealar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIGS. 9A-9F depict exemplary cancer (melanoma) boundary detection. Different sections of the subject tissue may have different normality statuses, which can be detected by the exemplary embodiments of the present invention.

FIGS. 11A-11C show exemplary diagnosis of fibroepitheliomas of pinkus, Basosquamal Carcinoma and Lentigo Maligna as described in Examples 2-4.

FIGS. 12A-16D show tissue images (H&E in grayscale) of various skin cancers (e.g., Melanoma, squamous cell carcinoma (SCC), basal cell carcinoma (BCC), Merkel Cell Carcinoma, Porocarcinoma) and benign lesions (e.g., Blue Nevus, Compound Nevus, Viral Wart, Benign Intra-dermal Nevus). FIGS. 12A-16D also depict variants and subtypes of each of the skin cancer types (e.g., SCC grading, BCC variants, in-situ or pre-malignant Melanoma etc.).

FIGS. 17A-19B show H&E tissue images of breast cancer. FIGS. 19A-19B depict lobular breast cancer with different grades.

FIGS. 32A-33C show IR images, thermal contours and feature plane points of Dummy Cell #1 and Dummy Cell #2.

FIG. 34A shows an IR image of a single biological cell from an exemplary IR imaging device, according to illustrative embodiments of the present invention. FIGS. 34B, 35B, and 36B depict temperature differences between the cell's nucleus and cytoplasm. The information surfaces of FIGS. 34C, 35C and 36C were calculated from these IR images.

FIG. 37A is an IR image of the loop made from a copper wire with a diameter of 561 μ. FIG. 37B is an IR image of the loop made from a bronze wire with a diameter of 222 μm. FIG. 37C is an IR image of the loop made from a copper wire with a diameter of 160 μm. FIGS. 37D-37F depict IR images of a silver mesh with a diameter of 270 micrometer and an opening size of 1580 μm.

DETAILED DESCRIPTION

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

All references cited herein, including patent applications and publications, are incorporated by reference in their entirety.

As mentioned above, the present disclosure relates to cancer detection. The present disclosure encompasses systems, methods, and apparatus for detecting cancer.

Metabolic imprints in cells are functions of cellular (e.g., molecular, physiological and phenotypic) parameters and cell cycle parameters (e.g., nuclear and nucleolar area, chromatin content, nuclear and nucleolar temperature, hotness of nucleus and nucleolus with respect to the rest of the cellular parts), which represent underlying tissue/cell conditions. In certain embodiments, detection of different types and subtypes of cancers and/or determination of a normality status of a subject tissue are extracted from the metabolic imprints by computing and measuring thermal and thermodynamic parameters.

Figure 5:
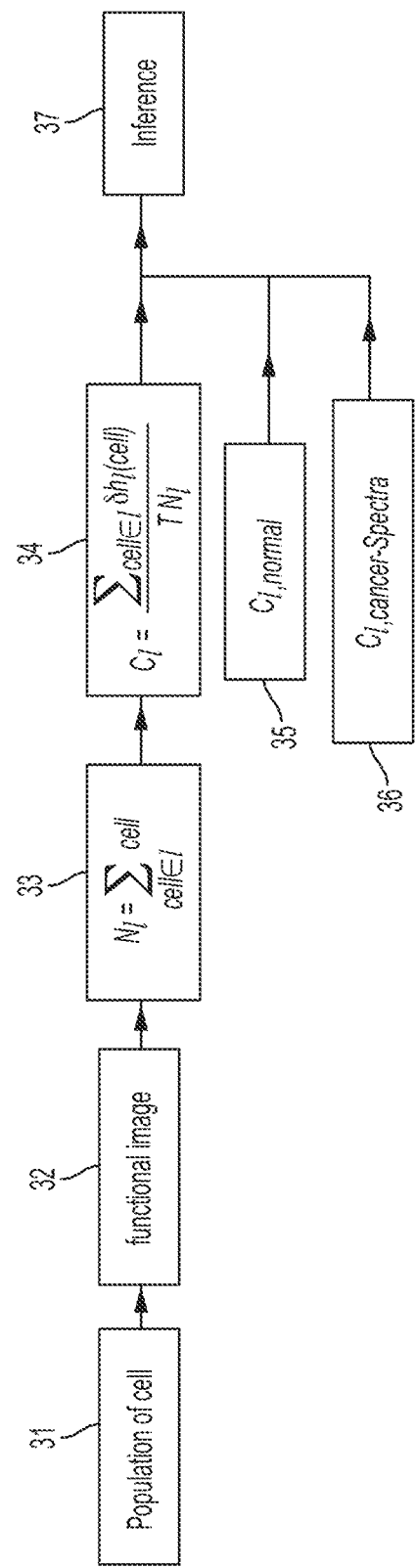
FIG. 5 is a schematic diagram of how molecular imprints are analyzed for determining a normality status.
Figure 7A:
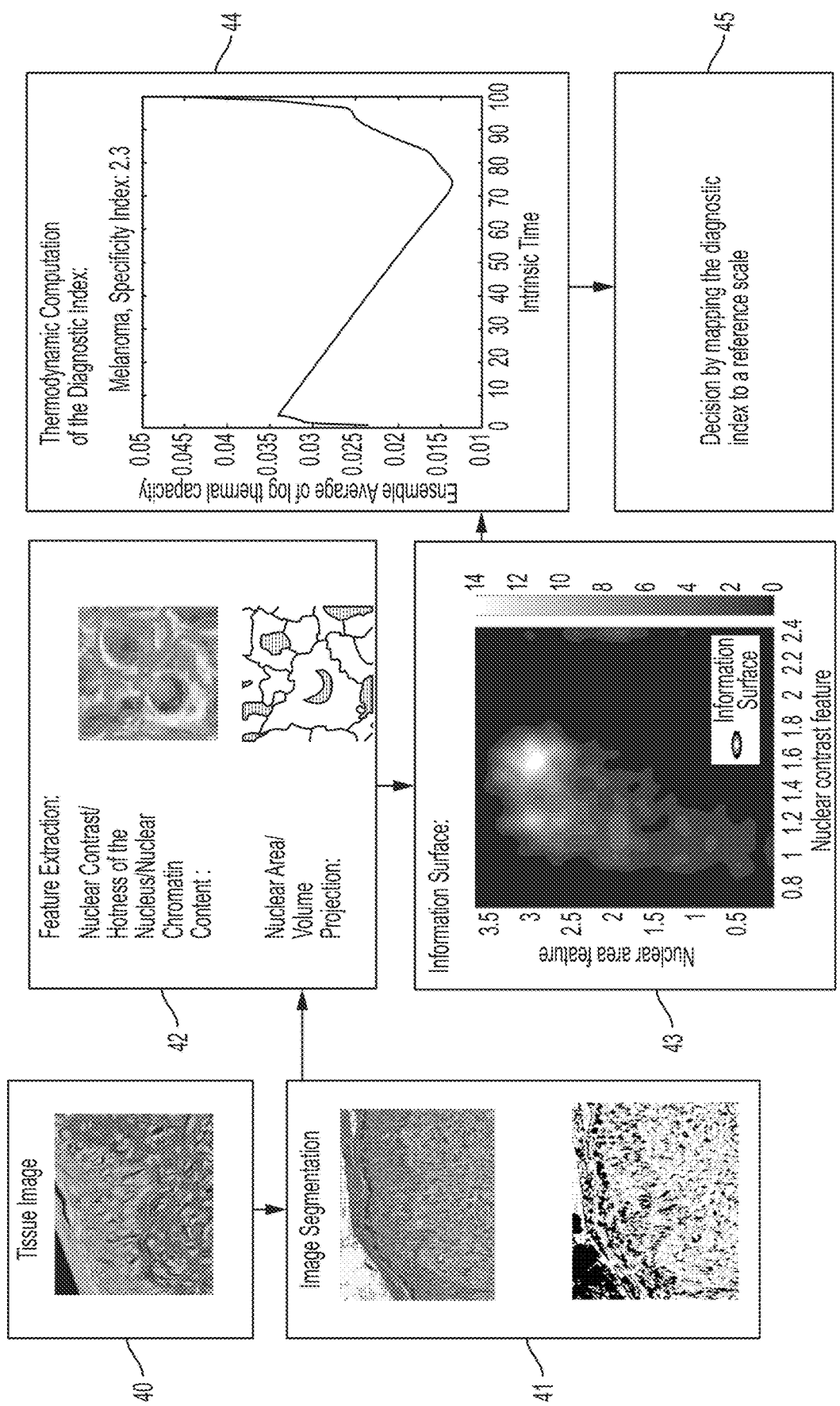
FIGS. 7A and 7B illustrate exemplary processes for obtaining a specificity index or a diagnostic score from a tissue image, which determines a normality status of a subject.
Figure 7B:
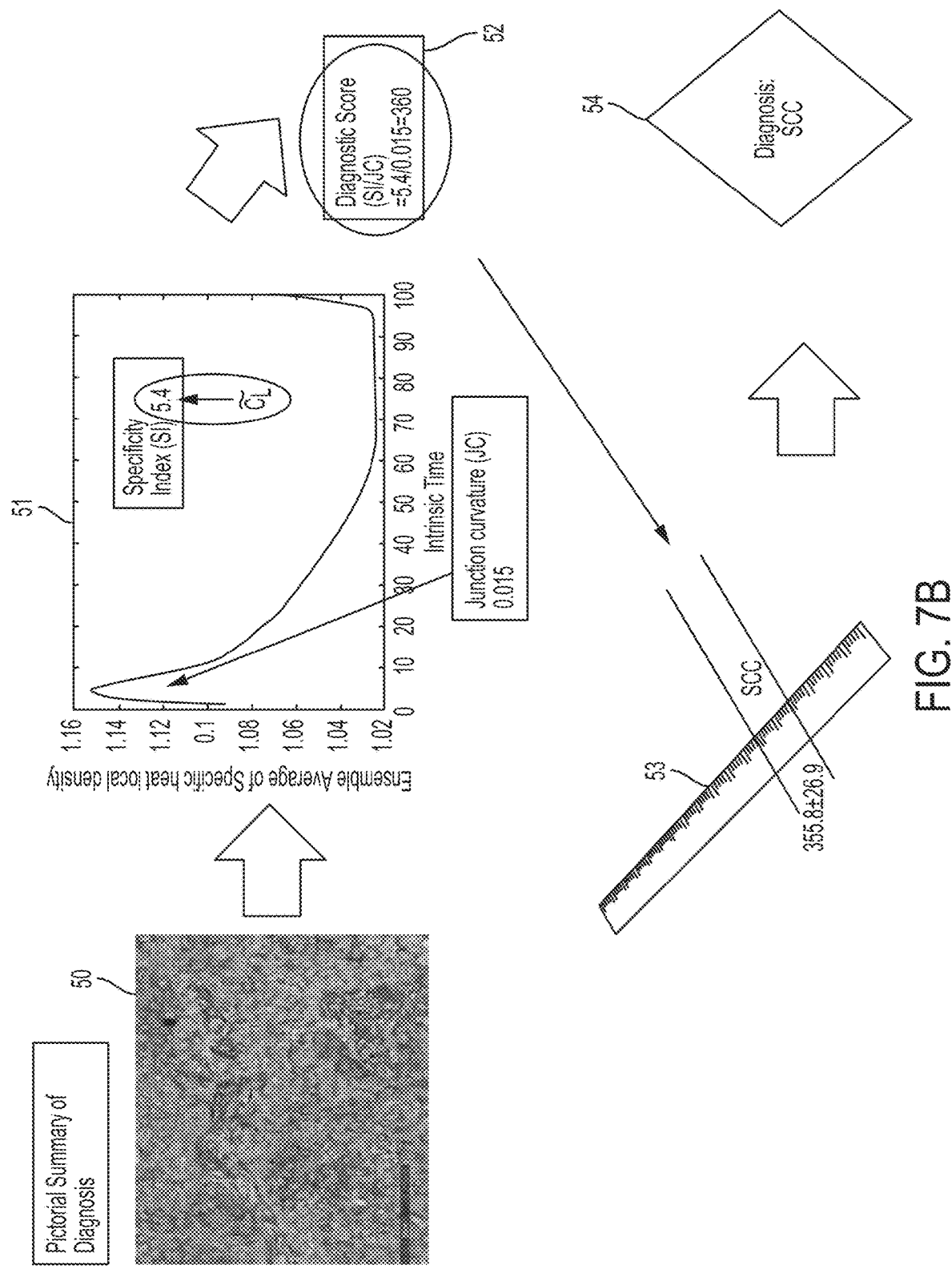
Figure 8:
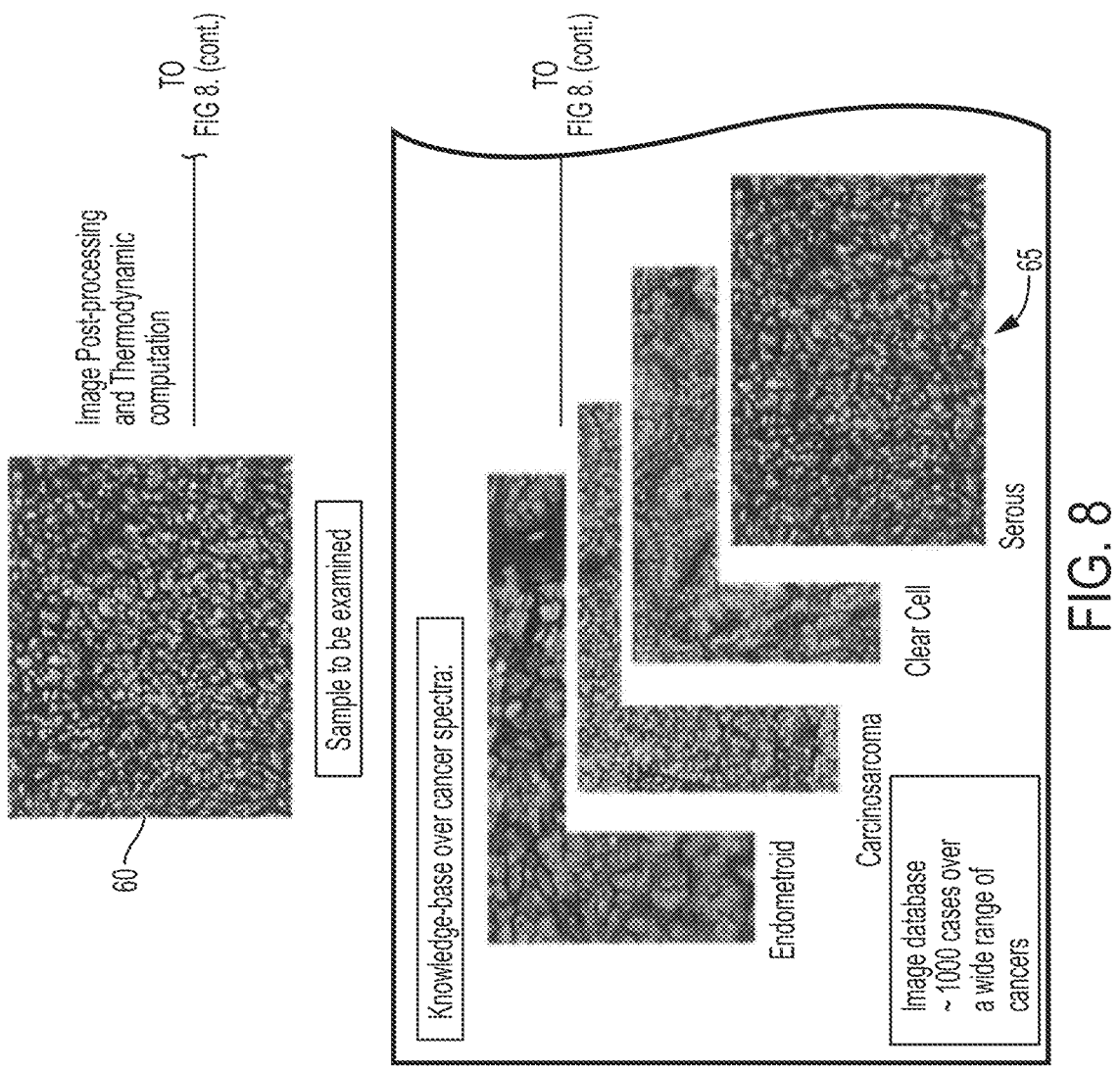
FIG. 8 shows an exemplary process for enhancing sensitivity and specificity of cancer detection by incorporating a knowledge-base.
Figure 8:
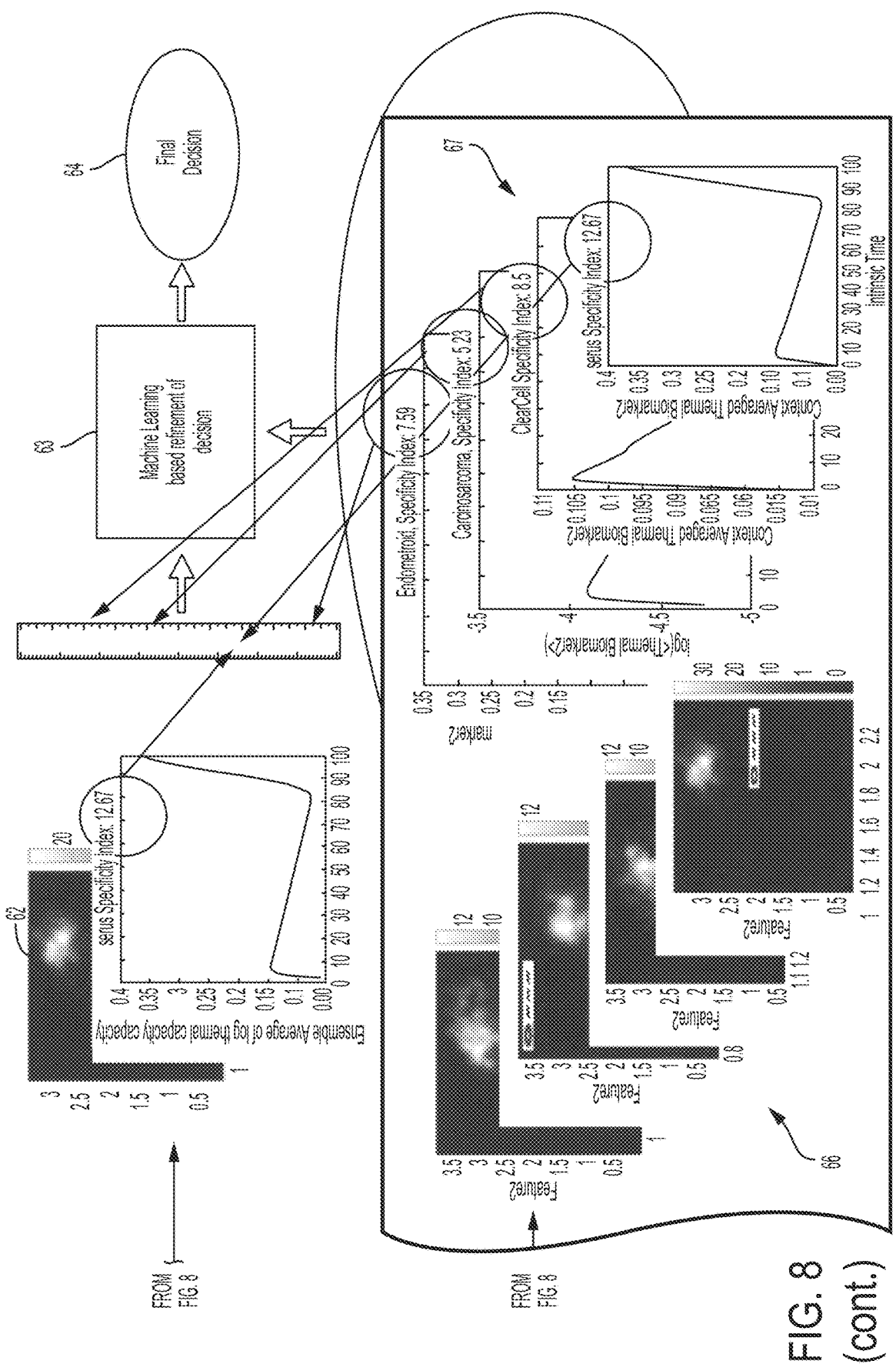
Figure 10:
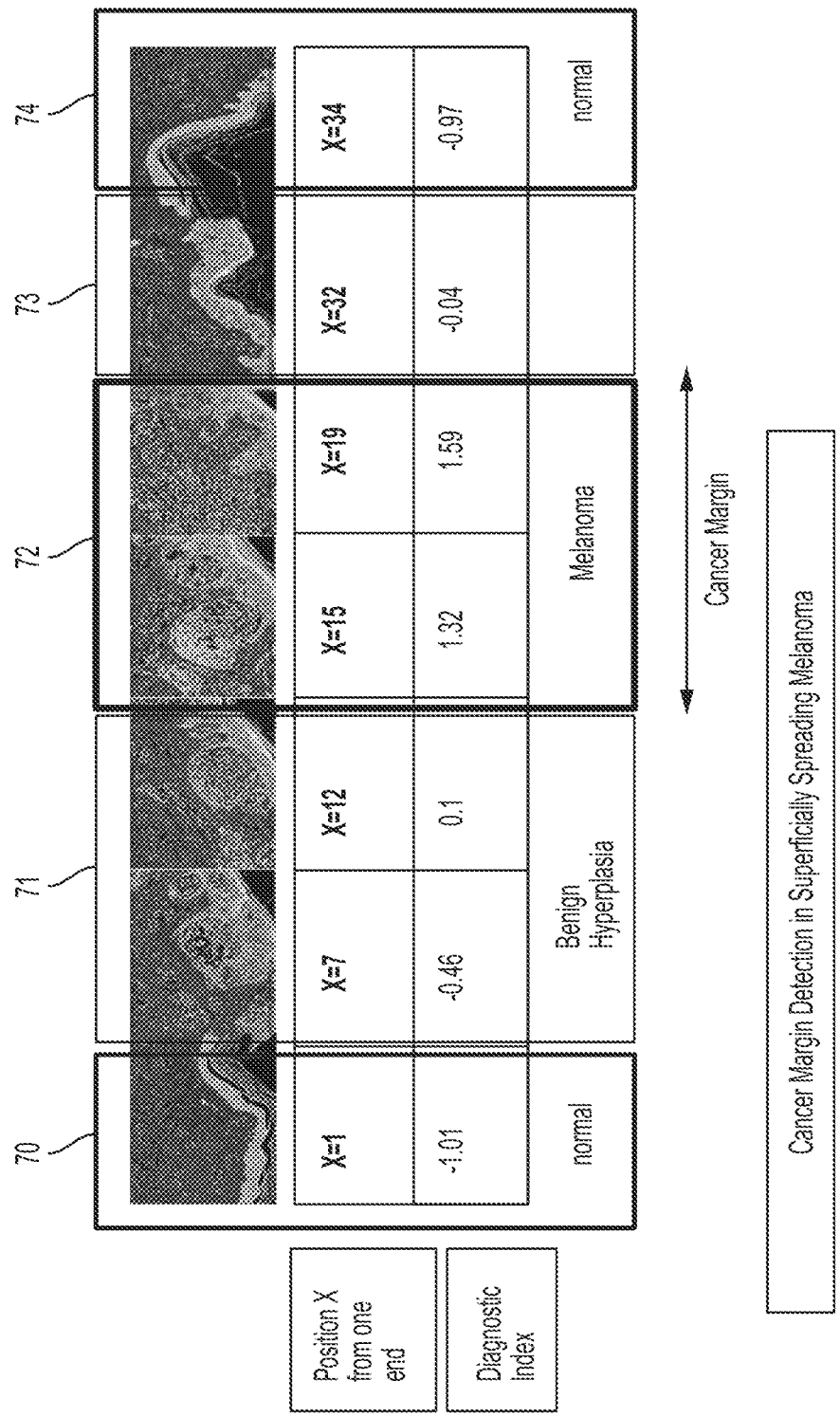
FIG. 10 depicts exemplary cancer boundary detection for the case of superficially spreading Melanoma.

In certain embodiments, the thermal and thermodynamic diagnostic parameters are computed from the ensemble (e.g., ensemble average) dynamics of the total heat generated at different cellular compartments, their contrasts and respective area or other size parameters. In certain embodiments, the thermal and thermodynamic diagnostic parameters are computed as a function of all wavelengths (e.g., a function averaged over the entire range of naturally emitted IR wavelengths from a cell or cells thereof). FIGS. 5, 7A and 7B show a schematic of an exemplary method for detecting cancer from molecular imprints of cells.

An exemplary method described herein includes identifying one or more cells in an image (e.g., an emitted IR image, an H&E image) of a subject tissue. Each of the cells in a field of view is segmented into a cellular area and a nuclear area. A nuclear area feature (a) is related to the ratio between a nuclear area and a nuclear volume projection. For example, the nuclear area feature (a) may be a function of a number of pixels within a nuclear area. A nuclear contrast feature (δh) is related to the hotness of the nuclear area with respect to the cellular area, the nuclear chromatin content, and/or the temperature of the nuclear area. For example, the nuclear contrast feature (δh) may be related to an average of pixel intensities within a nuclear area, which are higher than normal cytoplasmic intensity (e.g., an average of the pixel intensity within cytoplasmic area of normal healthy cells in a field of view).

In certain embodiments, the nuclear contrast feature and/or the nuclear area feature is obtained at the wavelength corresponding to the maximal radiant power of the naturally emitted IR. The nuclear contrast feature may be an average of multiple nuclear contrast features obtained at multiple wavelengths of the naturally emitted IR. The nuclear area feature may be an averaged value of multiple nuclear area features obtained at multiple wavelengths of the naturally emitted IR.

In certain embodiments, an information surface value (S) for each cell is calculated from spatial probability densities (e.g., $\Omega(a)$, $\Omega(\delta h)$, $\Omega(\delta h \times a)$, $\Omega(\delta h, a)$) of the nuclear contrast feature ($\delta h$) and the nuclear area feature (a). For example, information surface value (S) may be $$S = -\log\left(\frac{\Omega(\delta h \times a)}{\Omega(\delta h)\Omega(a)}\right) \quad (1)$$

In certain embodiments, the spatial probability densities of each cell is proportional to or a function of a fraction of cells. For example, the fraction of cells may be a ratio of a number of cells having a certain nuclear area or a range of nuclear area (e.g., greater than 5% of the median nuclear area) to the total number of cells in a field of view.

In certain embodiments, the cells in the subject tissue are divided into one or more subgroups depending on the information surface values (e.g., dimensionally reduced information surface values). The subgroups may correspond to different cell cycle stages and/or different intrinsic cell cycle time (L). In certain embodiments, the intrinsic cell cycle time (L) is related to chromatin content in a cell. For example, the intrinsic cell cycle time (L) is a function of the nuclear area feature and the nuclear contrast feature.

In certain embodiments, the thermal and thermodynamic diagnostic parameter is a specificity index (SI). The specificity index may be related to an ensemble average of local specific heats among cells ($<C_L>$) in each of the subgroups. The subgroups may be determined by, for example, the information surface values, extremization of the information surface values, and/or one or more intrinsic cell time (L) of the information surface values. In certain embodiments, the specificity index is an integration of the ensemble average of the local specific heats over cell cycle stages and/or intrinsic cell cycle time, e.g., $$\widetilde{C}_L = \!\!\int\!\!(\text{ensemble average of local specific heat})dL \quad (2)$$

In certain embodiments, the thermal and thermodynamic diagnostic parameter is a log thermal capacity (C). The log thermal capacity (C) may be related to a log of local specific heat among cells per unit area. In certain embodiments, the log thermal capacity (C) is an integration of the logarithm of the local specific heats among cells over cell cycle stages and/or intrinsic cell cycle time.

$$C = \!\!\int\!\!\log(\text{local specific heat among cells})dL \quad (3)$$

In certain embodiments, a normality status of the subject tissue is determined by a diagnostic score (e.g., calculated from the thermal and thermodynamic decision parameters). In certain embodiments, the diagnostic score is mapped on a reference diagnostic scale. The reference diagnostic scale may include pre-assigned values for different types of cancers and their respective subtypes, benign inflammations, and various normal healthy conditions. In certain embodiments, normal healthy tissues have low positive score or negative score in the reference diagnostic scale. In certain embodiments, the diagnostic score (F) is a function of the thermal and thermodynamic diagnostic parameter.

$$F = g[<c_L>, <c_L>_{max}, \widetilde{C}_L, \text{shape}(<c_L>), e^{-s}, <C>, \text{shape}(<C>)] \quad (4)$$

where is $<c_L>_{max}$ a maximum value of $<c_L>$ in a given field of view, shape($<c_L>$) is a shape feature of $<c_L>$, and shape($<C>$) is a shape feature of $<C>$. In certain embodiments, the shape feature is a value representing a shape of a curve of L vs $<c_L>$ or L vs $<C>$. For example, when the curve is a piecewise function, the shape feature is a number of subsections, a value of L at junctions, a curvature at a junction of the subsections, relative $<C_L>$ or $<C>$ between consecutive subsections, or critical exponents capturing nature of singularities if any at any of such subsections, for example.

In certain embodiments, the diagnostic score is F1, computed as follows:

$$F1 = \frac{SI}{\text{shape feature}} \quad (5)$$

For example, such diagnostic score can be utilized when identifying whether a sample is benign or cancerous. The diagnostic score (F1) may help to identify cancer types (e.g., malignant Melanoma, BCC, SCC, Merckel cell carcinoma, Porocarcinoma). Example 6 and Table 2 exemplify such diagnostic scores.

In certain embodiments, the diagnostic score is F2, computed as follows:

$$F2 = \frac{\Pi_i \text{ Shape } feature_i \times C}{SI} \quad (6)$$

where i is an integer and i>0. For example, such diagnostic score can be utilized when identifying different cancer variants, sub-types, grading, and/or stage within a particular cancer type. Example 6 and Tables 3-13 exemplify such diagnostic scores. In certain embodiments, one may calculate both F1 and F2. In certain embodiments, F1 is computed first to determine if a cell is cancerous or not. Then F2 may be calculated, so that one can diagnose different cancer variants, sub-types cancer variants, sub-types, grading, and/or stage of the cancers.

Figure 6:
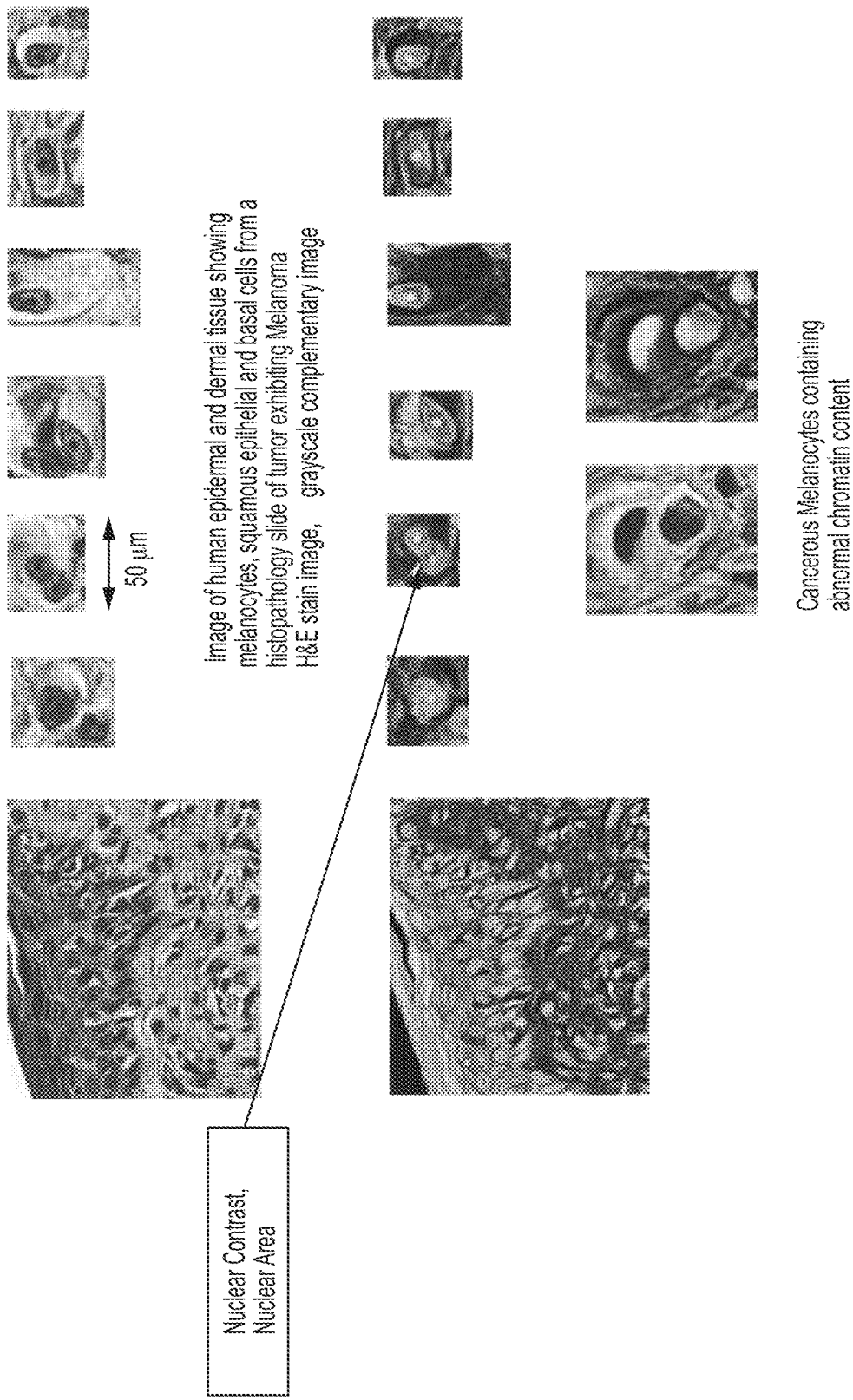
FIG. 6 depicts hematoxylin and eosin (H&E) stained images of human cells and their grayscale images. Cancerous cells in FIG. 6 contain abnormal chromatin contents.

FIG. 6 is images of human epidermal and dermal tissue showing melanocytes, squamous epithelial and basal cells from a histopathology slide of tumor exhibiting Melanoma. FIG. 6 includes H&E stain images, and their grayscale complementary images. Both of the H&E stain images and the grayscale images show cancerous Melanocytes containing abnormal chromatin content. FIG. 6 can be analyzed for cancer detection as shown in FIGS. 5, 7A, and 7B.

According to some embodiments, the present methods/systems may be applicable to detections of many cancer types and subtypes. The present invention does not require specific molecular signatures, unlike most of the cancer detection technics (e.g., Raman spectroscopy, optical absorption and scattering methods relying on scattering center pigmentation and chemistry, genetic and proteomic signature profiling methods). The present invention may not rely on phenomenological models based on phenotype detection methods (unlike machine learning based image analysis and prediction methods).

In certain embodiments, the thermal and thermodynamic decision parameters can detect cancer with high sensitivity, as the thermal and thermodynamic decision parameter can reflect tissue conditions by observing metabolic imprints. In certain embodiments, the present methods may reduce the chance of false positive or false negative cases. Characteristic curves (e.g., information surface, ensemble average of local specific heats) for each type of cancer have unique and distinct shapes. The high sensitivity may stem from the unique shape of the characteristic curve for each cancer (e.g., relative to the normal situation).

In certain embodiments, the specificity of cancer detection is further enhanced (e.g., once enough samples are analyzed) by creating a knowledge-base of characteristic curves for an entire spectrum of cancer types and subtypes at various tissue origins. Then, the detection of cancer types and subtypes can be further analyzed by comparing the updated characteristic curve via machine learning based classification/inference module, giving back a probabilistic score.

The present method may be used for locating cancer/normal cell boundaries. The image of the subject tissue is segmented into one or more sections. Each section is analyzed separately, assigning the specificity index or diagnostic score for each section. If a sudden change of the specificity index/ diagnostic score is observed, the image contains cancer/normal cell boundaries. FIGS. 9A-9F and 10 show exemplary cancer boundary detection.

Living tissues and cells are a heat reservoir that emits radiation. The wavelength of this radiation depends on temperature of the tissues and cells. An idealized physical body, which absorbs all incident electromagnetic radiations regardless of frequency or angle of incidence, is called a blackbody. A black body in thermal equilibrium emits electromagnetic radiations (i.e., black body radiations) which can be modeled by Planck's Law. The radiations have a specific spectrum and intensity that depend on the temperature of the body. Although the black body is a theoretical concept, living tissues may be approximated that its emitted energy spectra can be modeled by Planck's distribution formula. In practice, living tissues, similarly to other physical energy emitting sources, are a gray body and Planks' distribution formula still applies with a correction factor (e.g., gray body factor).

In certain embodiments, of the present method is capable of detecting subtle and difficult cases of cancer, when there are no prominent visual cancer signatures (e.g., human histopathologists are unable to come to a consensus conclusion) (e.g., detecting rare subpopulations of cancer, subtle mimics, Melanoma in situ, Melanoma look alike). In certain embodiments, the present method is capable of detecting subtle and difficult cases without requiring machine learning and/or artificial intelligence techniques.

Figure 3:
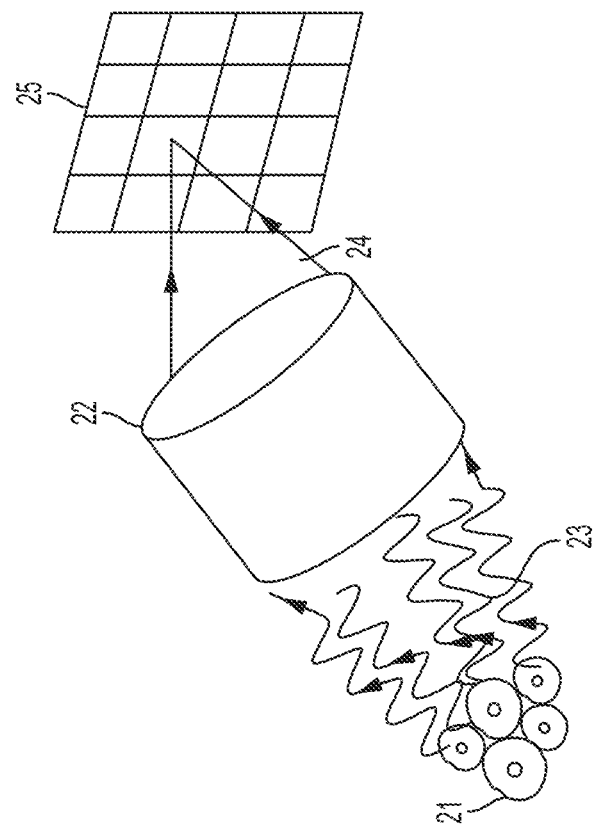
FIG. 3 is a schematic representation of exemplary cancer detection. Cancerous tissues or cells emit IR, which can be detected by devices presented herein.

Certain embodiments of the present invention provide in-vivo pre-surgery biopsy/cancer detection via infrared (IR) imaging devices that use naturally emitted IR from mammalian (e.g., human) tissues. In certain embodiments, the infrared imaging system measures the infrared heat energy emitted from a cellular area (e.g., cytoplasm, cytoskeleton), a nuclear area, or a whole cell (FIG. 3).

In certain embodiments, the infrared imaging system comprises a spatial magnification module, an IR detector, a signal processing module, and a memory. The spatial magnification module magnifies IR. The IR detector detects long wavelength IR emitted from a subject. The signal processing module operable with the memory to record a signal corresponding to infrared radiation detected by the infrared radiation detector and to cause rendering of an image (e.g., 1D, 2D, or 3D image) corresponding to the signal.

In certain embodiments, the infrared imaging system comprises a spatial magnification module made from a plurality of lenses. The lenses are permeable to infrared radiation and create images of cells/tissues in the focal plane of the IR detector. In certain embodiments, the infrared imaging system comprises a spatial magnification module made from a plurality of mirrors. The mirrors create images of cells/tissues in the focal plane of the IR detector. The spatial magnification module provides sufficient magnification to capture spatially resolved thermal contrast image of cells, internal and external parts of the cells.

In certain embodiments, the infrared imaging system comprises an IR detector to measure the emitted infrared radiation from cells. The IR detector may comprise an uncooled vanadium oxide surface. Vanadium oxide surface may be used in microbolometer configuration as a detector. In certain embodiments, the infrared imaging system comprises a mercury cadmium telluride (HgCdTe) surface.

Figure 27:
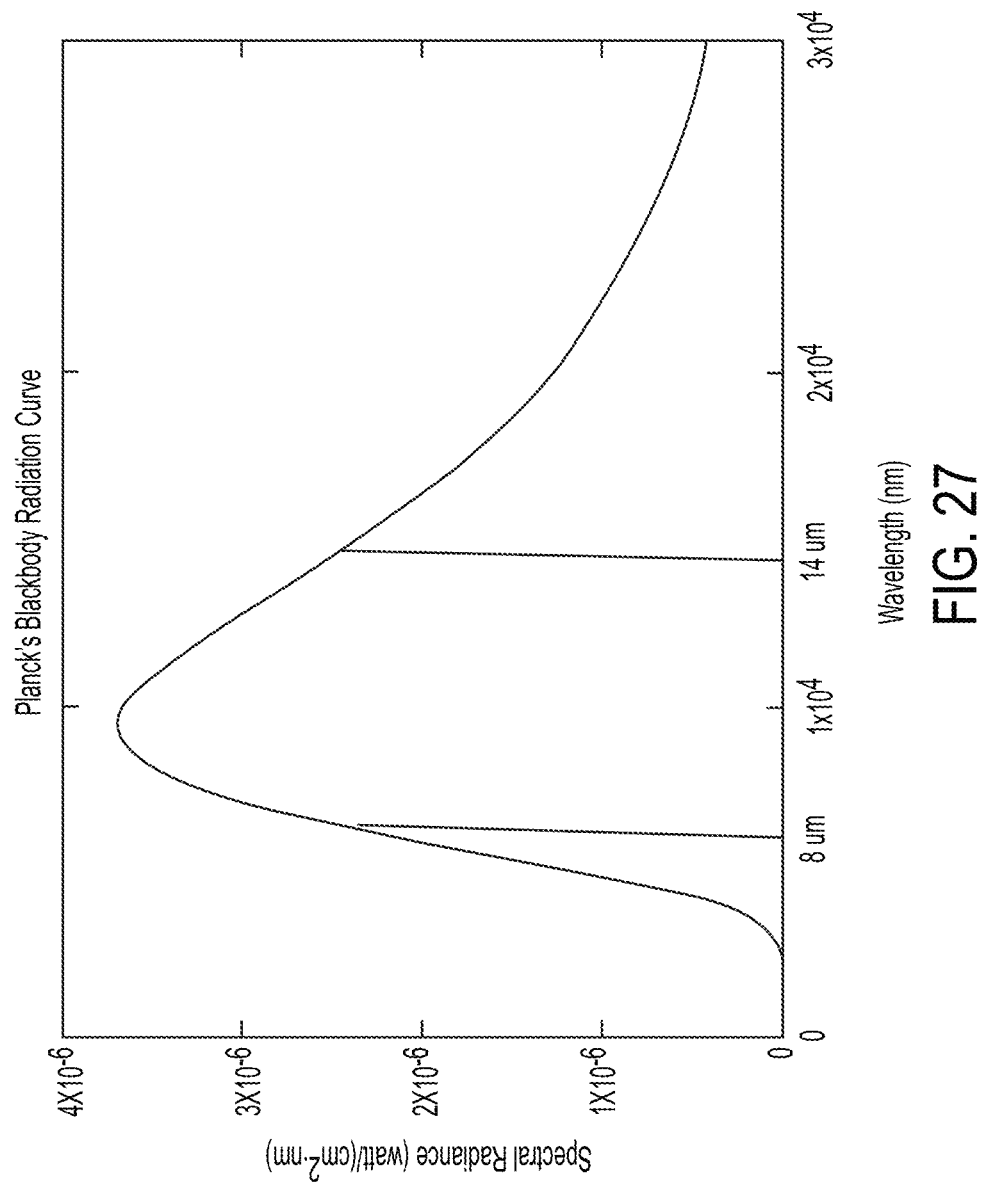
FIG. 27 depicts Planck's blackbody radiation curve, when the temperature is 37° C. (i.e., 310K).

Planck's distribution can be expressed as follows:

$$\rho(\lambda, T) = \frac{(2hc^2/\lambda^5)}{1 - e^{-hc/\lambda kT}} \qquad (7)$$

where p is the spectral radiance, $\lambda$ is the wavelength, h is the Planck's constant, c is the speed of light, k is Boltzmann's constant ($1.38 \times 10^{-23}$), T is temperature in Kelvin. For a typical human body, the temperature ranges 27-38° C., i.e., 310-322 K. Planck's blackbody radiation curve of T =310 K has a peak around X=10 μm, and the curve starts at around $\lambda$=3 μm and extends beyond $\lambda$=30 μm, as shown in FIG. 27.

In certain embodiments, the IR detector detects IR having a wavelength of 3 to 30 pm. In certain embodiments, the IR detector detects IR having a wavelength of 6 to 20 μm. In certain embodiments, the IR detector detects IR having a wavelength of 8 to 14 μm. For detecting IR in the whole range of 3-30 μm, one needs to detect thermal photons having a photon energy range of 40 to 400 meV. Such a large range of photon energy requires the use of many sensors made from many materials with different energy bandgap, different operating conditions and sensitivity. For example, in order to collect IR having a wavelength below 8 μm, a mercury cadmium telluride (MCT) or Barium Strontium Titanate (BST) may be used, however, they require extensive liquid $N_2$ (77 K or -196° C.) cooling. To collect IR having a wavelength above 14 μm, MCT also may be used, but also requires liquid $N_2$ cooling. The cooling apparatus are typically bulky, not suitable for portable use. To collect IR having a wavelength of 8-14 μm (e.g., with a peak at 10 μm), a vanadium oxide detector can be used. The vanadium oxide detector can be operated at room temperature, has great signal to noise performance, and can be portable (e.g., due to its small size). Images for cancer detection may be produced from IR having a wavelength of 8-14 μm.

Figure 1:
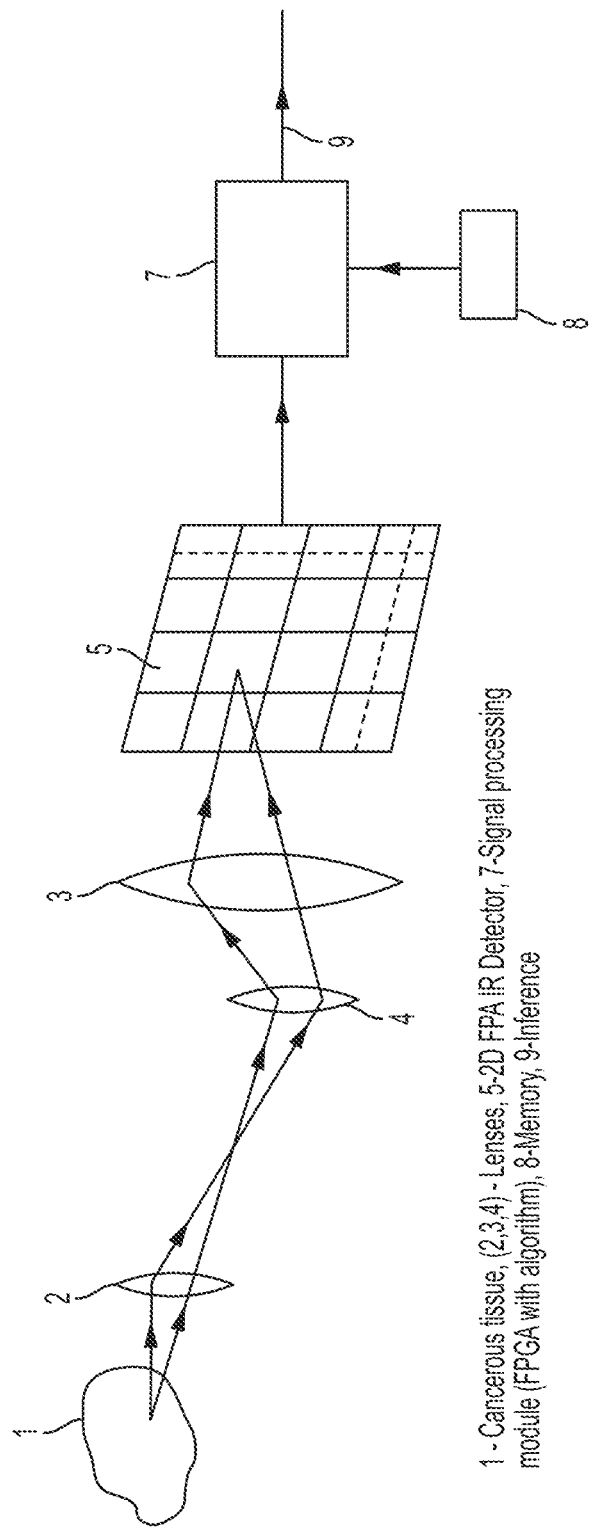
FIGS. 1 and 2 depict exemplary devices for detecting cancer, according to illustrative embodiments of the present invention. Each of the devices comprises a two dimensional IR detector and either (a) a series of optical lens (FIG. 1) or (b) a series of curved mirrors (FIG. 2), providing spatial magnification for the image formed by the signal emitted from cells/tissues to be observed.
Figure 2:
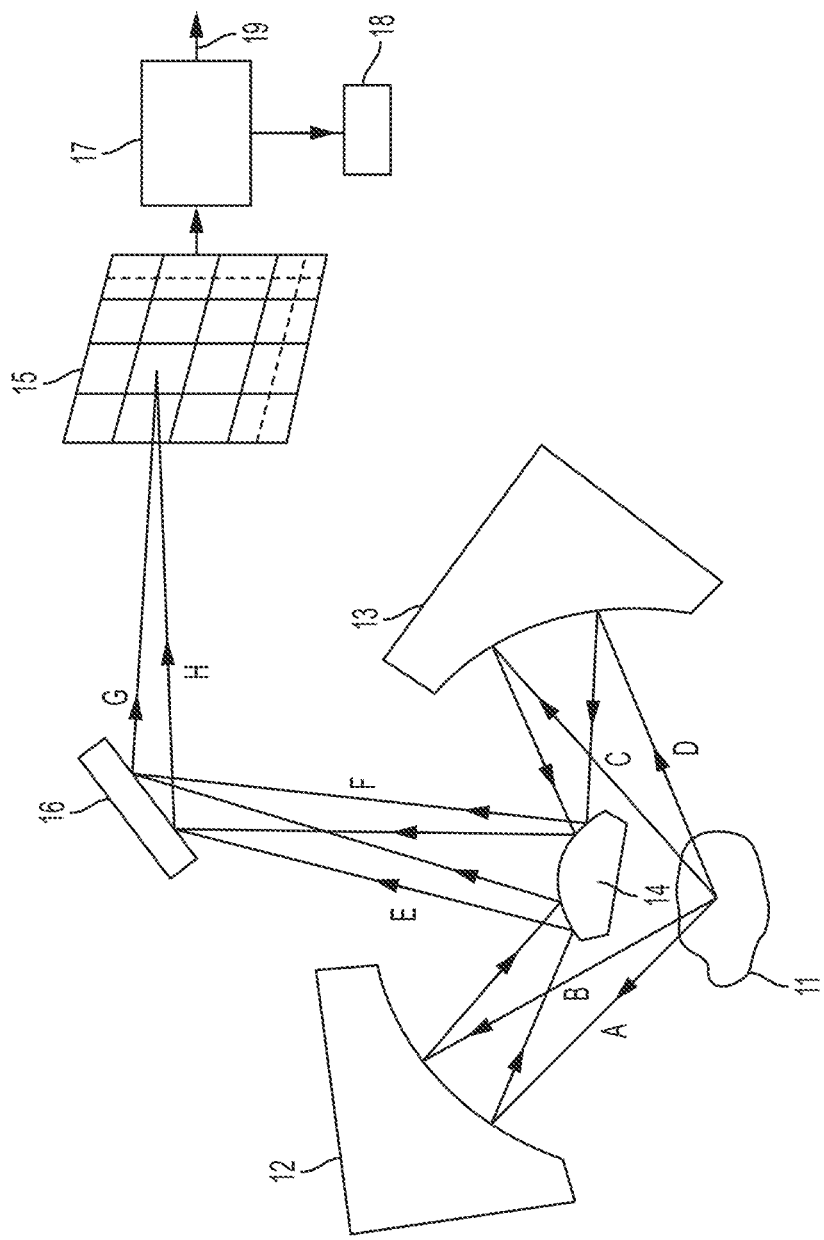

FIGS. 1 and 2 illustrate the layout of two exemplary devices. The devices comprise a two dimensional detector (e.g., Focal plane array (FPA)), IR detector, and either spaced apart optical lens in transmission configuration (FIG. 1) or curved mirrors in reflection configuration (FIG. 2). Both provide spatial magnification for the image formed by emitted signal irrespective of the wavelength of the signal emitted from the cells or tissues, to be measured. The space between the optical elements may be filled with a neutral gas medium (e.g., dry air, nitrogen), or may be kept at vacuum. The thermal signal (e.g., IR) emitted from the cancerous cells or tissues (1) may be detected by the detector (5), after passing through either the lens system or mirror system. Such an emitted signal carries the necessary and sufficient 'spatial' and 'temporal' metabolic and thermodynamic information of the cell cycle and subsequently detected of the cell cycle and is subsequently detected by the 2D FPA IR detector. The detector measures the Intensity I (i.e., photon energy flux) of such emitted signal over a broad band of emitted signal wavelength (k). Signal intensity can also be expressed by the incident signal IR photon number flux N(E) integrated over the incident signal IR photon energy (E) distribution. Hence the detector output voltage signal S(k) can be expressed as $$S(\lambda)=\int I(\lambda)d\lambda=\int N(E)dE \quad (8)$$

In certain embodiments, in addition to individual detector pixels registering the integrated Photon energy flux N(E), the reflective or transmissive optical system provides the spatial magnification (M) for the objects (i.e., the cell/tissue) emitting the signal. The signal creates a 2-D image due to the difference of IR signal photon flux emitted from different parts of the object differing in temperature and subsequently detected by the spatial array of pixels on the 2-D detector. The efficiency of capturing images is dependent upon several factors (e.g., objective magnification, numerical aperture, resolution). The ultimate optical resolution of the detector is a function of the number of sensing pixels and their size relative to the image projected onto the array surface by the optical magnification system. The image size projected onto the surface of the detector depends upon both the optical resolution and the optical magnification (e.g., image size on the detector=Optical Resolution (R)×Magnification (M)). For an objective with a 35× magnification factor at a numerical aperture (NA) value of 0.95, the Optical Resolution (R) is given by R=(0.61×λ)/(NA=(0.61× 10 μm)/(0.95=6.4 μm)). The image size on the detector is 6.4×35=224 μm. Thus, to achieve the full resolution, in certain embodiments, the pixel size of the detector is 112 μm or less. The detector pixel size used in the proposed system is 17 μm and is well within the size requirement. The detector output voltage signals $S(\lambda)_{m,n}$(m=1 . . . N, n=1 . . . N) from 2D array of each individual pixel are fed to the signal processing module (7) comprising an FPGA. The FPGA is connected with a memory interface. The algorithm associated with the FPGA then extracts the required ensemble averaged thermodynamic and metabolic information from the detector signals, and draws the final inference.

In certain embodiments, the spatial magnification module comprises three lenses, for example, as shown in FIG. 1. A subject (e.g., cells or tissues) may be placed outside the focal distance of a first lens (e.g., Lens 2 in FIG. 1) (e.g., The first lens may have a short focal length e.g., 1-10 mm, 1-5 mm, about 1 mm, about 2 mm, about 3 mm, about 4 mm, about 5 mm). The first lens creates a real inverted magnified image. A distance between the first lens and the real inverted magnified image may be more than twice the focal length of the first lens. A distance between the real inverted magnified image and the second lens (e.g., Lens 4 in FIG. 1) may be less than the principal focus of the second lens. The second lens re-magnifies the real inverted magnified image, which is focused on the detector plane 5 by the third lens (e.g., Lens 3 in FIG. 1).

In certain embodiments, the spatial magnification module comprises two mirrors (e.g., similarly to Schwartzschild Cassegranian aplanatic telescope system), for example, as shown in FIG. 2. The spatial magnification module may comprise a convex mirror (e.g., 13 in FIG. 2) and a concave mirror (e.g., 11 and 12 in FIG. 2, each of which are a part of one same mirror). The two mirrors are substantially concentric. The reflective surface of the convex mirror faces the reflective surface of the concave mirror. The concave mirror comprises an opening, so that the IR passes through.

In certain embodiments, the infrared imaging system measures photon flux from different part of the object as a function of wavelength to create the two dimensional images. In certain embodiments, the infrared imaging system comprises an external infrared source (e.g., heat source), which heats up the cells or tissues and increases the average threshold of the emitted infrared radiation flux from those cells and tissues. In certain embodiments, the infrared imaging system is operable without an external light source.

In certain embodiments, the image acquisition and analysis (Image processing module) are performed in real time using field-programmable gate array (FPGA). Extraction of thermodynamic quantities and computation of diagnostic score (Thermodynamic Computation Module) may be performed in real time using an FPGA. Cross checking the diagnostic score with the knowledge base of cancer spectra (e.g., machine learning based probabilistic inference module) may be performed in real time using an FPGA.

Figure 21:
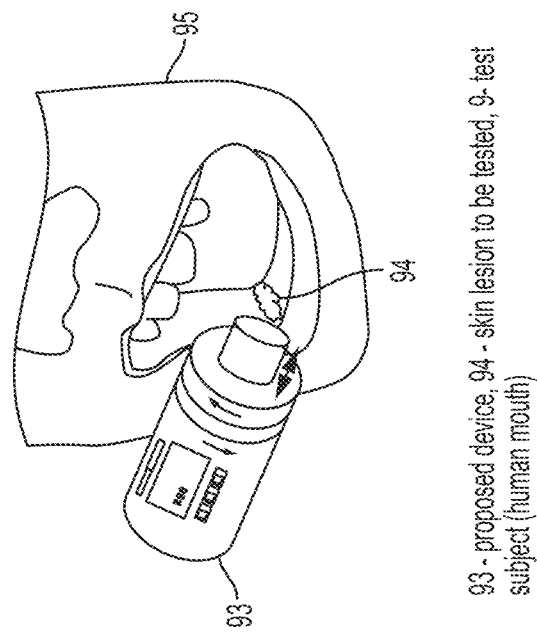
FIGS. 20-22 illustrate exemplary devices for detecting molecular imprints of cancerous cells from skin lesions, according to illustrative embodiments of the present invention.
Figure 20:
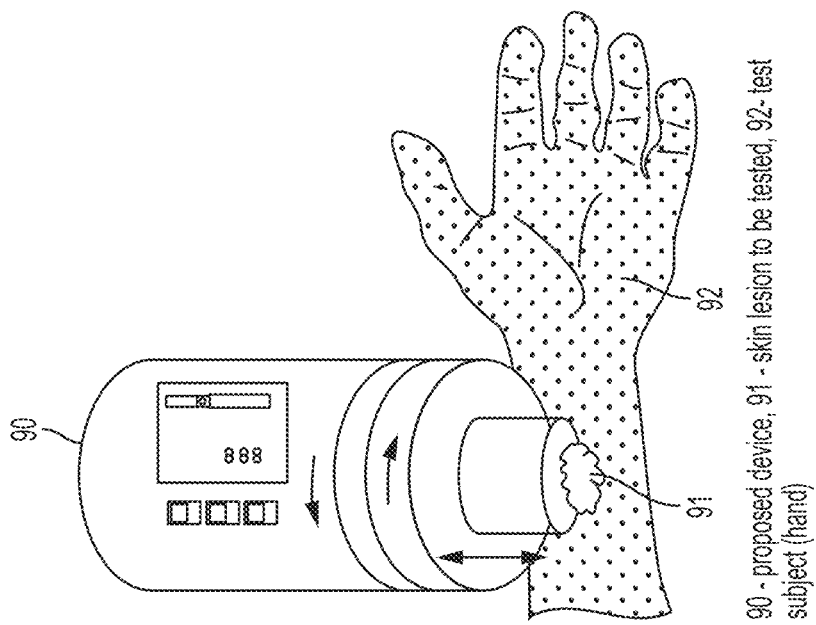
Figure 22:
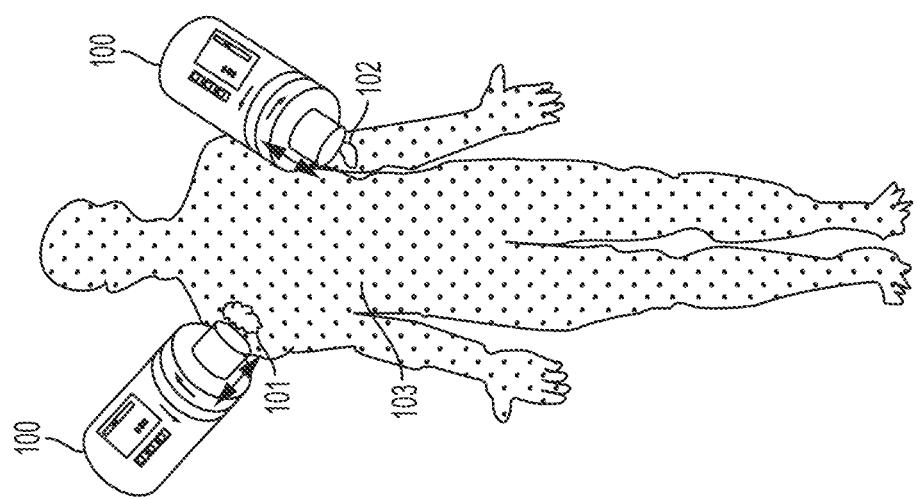
Figure 28:
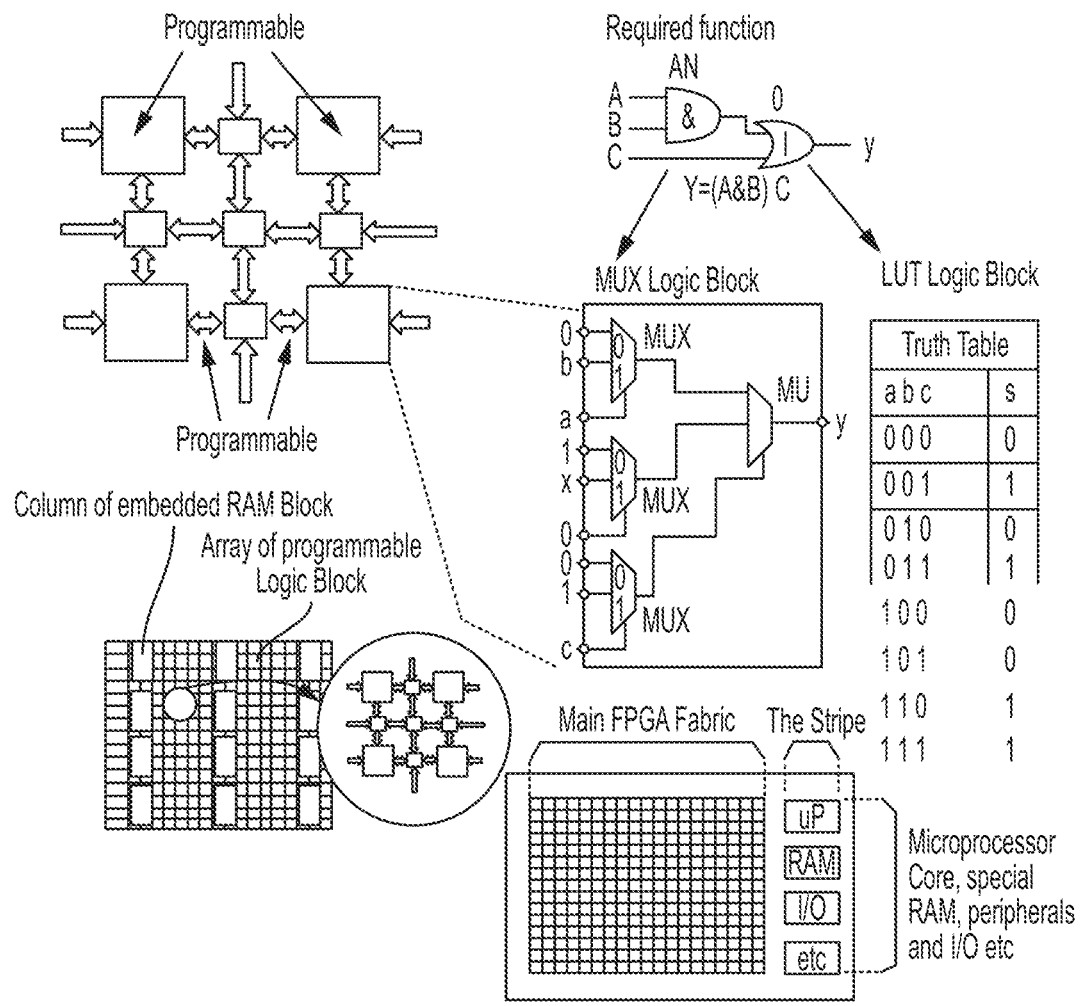
FIG. 28 depicts an exemplary FPGA architecture and implementation.

In certain embodiments, FPGA is used for implementing the real-time algorithm implementation and the associated device control, so that a portable handheld real-time device can be realized (as shown in FIGS. 20-22). An FPGA is an integrated circuit consisting of a large number of programmable logic blocks, I/O cells and interconnection resources implemented on a chip which allows the chip to be reconfigured to implement a certain program in many different ways (as shown in FIG. 28). A large number of logic blocks can be connected together to perform parallel and fast real-time processing. Many electronic circuits can be implemented physically through programming of the FPGA logic blocks using a Hardware description language (DHL) (e.g., VHDL or Verilog).

Figure 29:
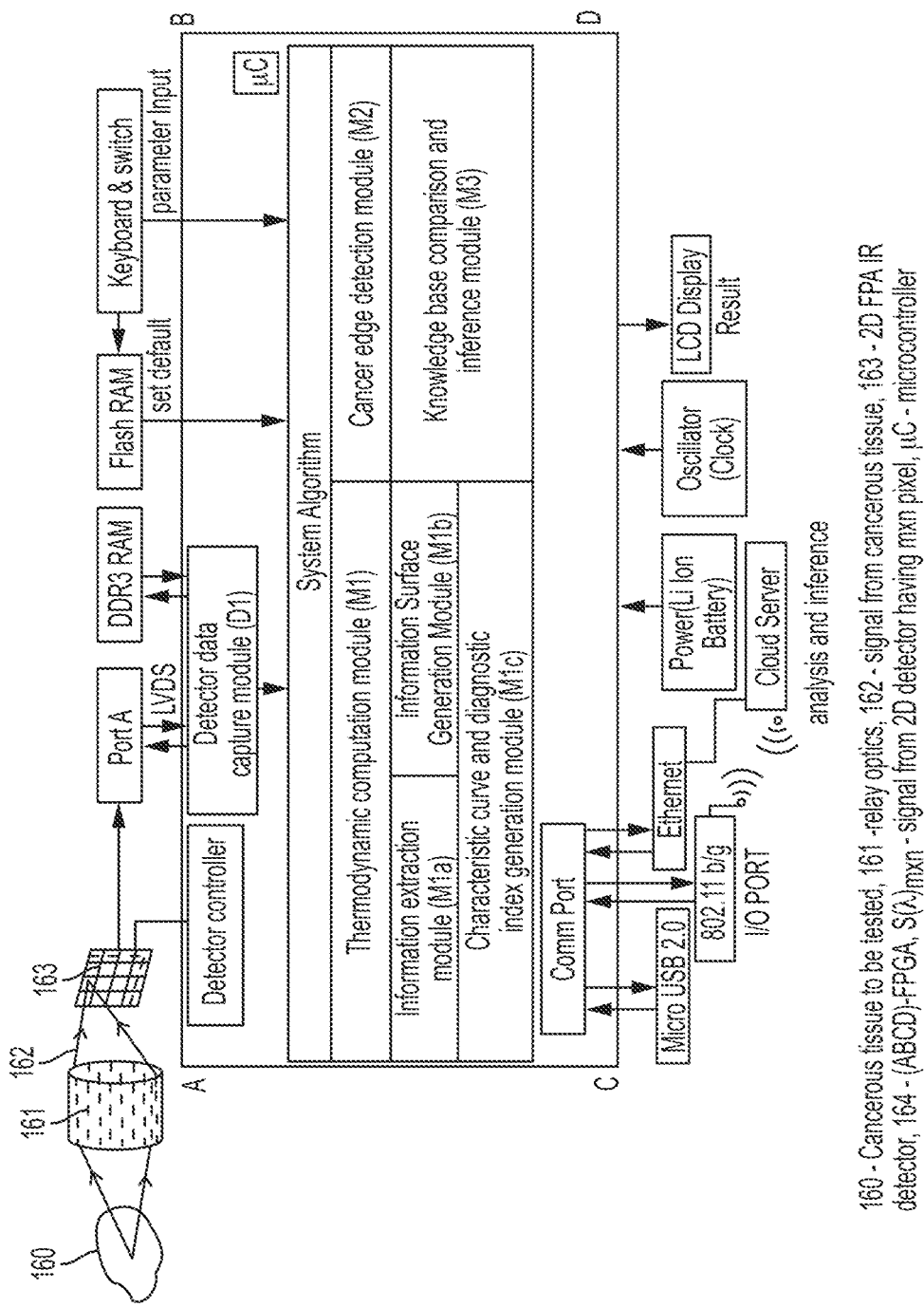
FIG. 29 depicts signal processing sections of an exemplary device.

In certain embodiments, architecturally FPGA contains a large number of the programmable logic blocks (or Logic Cell) embedded in programmable interconnection. Each logic block can be used to implement a simple function. For example, it might be possible to configure the block to act as any 3-input function such as a primitive logic gate (e.g., AND, OR, NAND) or a storage element (e.g., D-type flip-flop, D-type latch) as shown in FIG. 29. Hard-wired multiplier blocks and dedicated adder blocks are used for Multiply, Add, and aCcumulate (i.e., MAC) operation. Such logic blocks are implemented either as MUX (multiplexer) based or LUT (lookup table) based. MUX based logic blocks contain multiple layers of multiplexers, and each input to the block is presented with a logic 0, a logic 1, and that allows each block to be configured to implement a plethora of possible functions. In a LUT based system, a group of input signals is used as an index (pointer) into a lookup table. The contents of the table are arranged such that the cell pointed by each input combination contains the desired value.

In certain embodiments, each logic cell's LUT, MUX, and register have their own data inputs and outputs. Clock, clock enable, and set/reset signals are common to logic cells. Many applications require the use of memory. Thus, FPGAs include relatively large embedded RAM called block RAM as shown in FIG. 18.

Often FPGA logic blocks are named differently by (a) different vendor(s). For example, FPGA from Xilinx is called a logic cell (LC). An LC comprises of a 4-input LUT, a multiplexer and a register. A LUT can also work as a 16×1 RAM or a 16-bit shift register. The next step up the hierarchy of the structure, which contains two logic cells, is called a slice. For example, the Virtex-5 FPGA family from Xilinx has four 6-input LUTs per slice. One more level up in the hierarchy is called the configurable logic block (CLB) (in Xilinx) or logic array block (LAB) (in Altera). A CLB from Xilinx may contain 2 (or 4) Slice.

As mentioned above, an electronic design may be realized in hardware (e.g., using logic gates and registers etc.) and/or software (e.g., as instructions to be executed on a microprocessor). Fast process (e.g., picosecond and nanosecond logic) mandates software implementation in hardware (e.g., in the FPGA fabric). In certain embodiments, fast process is to be used to achieve the real-time imaging and algorithm data processing while slower millisecond logic may be implemented as a microprocessor code for non-time processes (e.g., the detector function control). Microprocessor may be implemented as a hard- microprocessor core using dedicated, predefined block inside or in a strip next to main FPGA. It is also possible to configure a group of programmable logic blocks to act as a microprocessor (e.g., soft cores (e.g., PicoBlaze, MicroBlaze etc. from Xilinx)).

In certain embodiments, to implement an electronic circuit, the FPGA logic blocks have to be programmed using a Hardware description language (DHL) (e.g.,VHDL or Verilog). Each FPGA vendor also offers its own selection of hard, firm, and soft implementation of HDL, which is called intellectual property (IP) core. The hard IP comes in the form of pre-implemented blocks such as microprocessor cores, gigabit interfaces, multipliers, adders, MAC functions, FFT core, etc. IP core can be used as a module inside a big program, which simplifies the work of writing a big program. Several of low level IP is used to implement the present method in Xilinx FPGA (Virtex) using Xilinx Vivado design suite and also in Altera FPGA (Stratix) using Altera' s Quartus prime development environment.

Referring to FIG. 29, the signal (3) emitted from the cancerous tissue/tumor (1) is processed through the Optical module (2) and detected by the 2-D FPA IR detector (4). The detector has its own FPGA circuit that processes the detected integrated signals over wavelength λ, i.e., f I. (λ)dλ from all m×n {m=1 . . . N, n=1 . . . N} pixel of the 2-D detector. The 2-D signal matrix $S(\lambda)_{m \times n}$ after processing are passed to the port A of the processing FPGA (ABCD) through a LVDS (Low Voltage Differential Signaling) bus and then processed in real-time and stored on board by a detector data capture module (D1) using a fast onboard DDR3 RAM storage. The captured signal is passed to a System Algorithm module consisting of following various sub modules e.g., 1) Thermodynamic Computation module (M1) comprising of but not limited to information extraction module (M1a), information surface generation module (M1b), characteristic curve and diagnostic index generation module (M1c), 2) cancer boundary detection module (M2) and 3) knowledge base comparison and Inference Module (M3). These modules processed the signal matrix $S(\lambda)_{m \times n}$ and calculated various thermodynamic parameters, indexes, and edges, which display the final results (inference) in the LCD display and is also available through several I/O communication port (Comm) e.g., micro USB 2.0, 802.11b/g and Ethernet.

For a portable device, the full processing may be done inside FPGA. While for some other cases, FPGA is used for partial data manipulation (e.g., detector data capture and pre-processing) while the rest of the work (e.g., analysis and inference) is done by uploading the data to a cloud server and using a web app for analysis and inference, for example. A microcontroller (X) is used to control various internal operations and a detector controller module controls the various detector operations. An oscillator provides the necessary time signal and the power is provided by a Lithium ion battery. A keyboard and several switches are used to provide parameter inputs to the modules and a Flash RAM is used to store default parameter values to be loaded during startup. The FPGA used here consist of a large number of programmable logic blocks, I/O Cells and interconnection resources which are programmed to realize the necessary electronic circuit to process the detector signal in real-time. The modules (e.g., D1, M1a, M1b, M1c, M2, M3) are programmed using a hardware description language (e.g., verilog) and either written from scratch and/or by using several pre-implemented blocks of hard or soft intellectual property core from the vendor (e.g., Xilinx, Altera). Programs are implemented in Xilinx FPGA (Virtex) using Xilinx Vivado design suite and also in Altera FPGA (Stratix) using Altera's Quartus prime development environment.

In certain embodiments, the spatial resolution (e.g., 5 microns) obtained by the present device at mid-IR range is sufficient to capture images of mammalian cells. In certain embodiments, the spatial magnification module has a resolution of 40 microns or less. In certain embodiments, the spatial magnification module has a resolution of 30 microns or less. In certain embodiments, the spatial magnification module has a resolution of 20 microns or less. In certain embodiments, the spatial magnification module has a resolution of 10 microns or less. In certain embodiments, the spatial magnification module has a resolution of 5 microns or less.

To detect spatial temperature differences within different parts of the cell/tissue, a suitable thermal detector is required. In certain embodiments, an intrinsic thermal sensitivity and a noise-equivalent temperature (NET) value of a detector is an important parameter. NET specifies an amount of radiation required to produce an output signal equal to the detector's own internal noise (e.g., the signal-to-noise (S/N) ratio is one). NET may represent a minimum temperature difference, which the thermal detector can resolve. NET can be calculated by dividing a temporal noise by response per degree (e.g., responsivity measuring electrical output per optical input). NET is typically expressed in units of Kelvin (K). Cooled infrared detector systems typically have low noise levels, in a range of 10-30 milli Kelvin (mK). Uncooled infrared detector systems are typically noisier, in a range of 30-120 milli Kelvin (mK). The NET and the sensitivity of the thermal detector are inversely correlated.

Among uncooled detectors, vanadium oxide microbolometer thermal detector has a relatively low NET value (e.g., about 39 mK at T=25 ° C.). An uncooled Barium Strontium Titanate (BST) has NET of about 100 mK. A mercury cadmium telluride (HgCdTe) detector has a NET value of about 10 mK but requires liquid nitrogen cooling to operate, which is expensive, bulky and hard to use in portable devices. Hence, 2-dimensional (e.g., 640×512 array, 17 μm pixel or similar) vanadium oxide microbolometer thermal detector operating in 8 -14 μm range may be suitable for the present system. For example, for a metabolically active live cell/tissue, a temperature difference within the cell/tissue (ΔT) is about 0.5-1 Kelvin, which is several order higher than the NTE value of detectors (e.g., vanadium oxide, HgCdTe). Thus, the detectors may have high enough sensitivities for imaging a temperature difference between the nucleus and cytosol of a cell.

Overall thermal sensitivity or NET value for a device is also related to several other noises contribution (e.g., shot noise or Johnson noise). The effect of such noises may be decreased (e.g., the NET value decreased) by increasing integration time. The Johnson noise voltage of a resistor can be expressed as $$E = (4kTR\Delta f)^{1/2} \qquad (9)$$

where E is a Root-Mean-Square voltage level, k is Boltzmann's constant (1.38 x $10^{-23}$), T is temperature in Kelvin, R is resistance, and $\Delta f$ is circuit bandwidth in Hz. A vanadium oxide detector has an impedance R of about 100 Kohm. An a-Si detector has an impedance of about 30 Mohm. A resistor of the vanadium oxide detector will have a higher current than one of the a-Si detector at the same voltage. Therefore, the Johnson noise (or thermal noise) of vanadium oxide will be lower than that of a-Si detector. Some noise can come from associated electronics hardware, which can be reduced to about zero.

IR detector performance parameters (e.g., detector responsivity R, which is a measure of electrical output as a function of optical input) can be calculated as a function of various experimental conditions (e.g., IR source temperature T (e.g., Human body at ~310° K±3° K), emitted IR wavelength range $\Delta k$, and its spatial resolution $\Delta \lambda / \lambda 0$, temperature sensitivity $\Delta T$ of the detector, transmittance $\Delta \lambda$, of the ambient media, source solid angle at the detector plane given by object/source distance, source and lens area, etc.). The electrical output may be measured by creating voltage fluctuation, which in turn can be mapped to spatial temperature fluctuation via a thermal change of resistance. Combining the definition of detector responsivity R and Planck's radiation law, and integrating over the wavelength range of IR from $\lambda_0$ to $\lambda_0 + \therefore \lambda$ (e.g., 8-14 μm), where C and a are constants set by source's thermal property and Planck's radiation law:

$$R = \frac{C}{\tau(\lambda_0 \to \lambda_0 + \Delta\lambda)} \times \frac{d_{source}^2}{A_{source} A_{lens}} \times \left[ \frac{\Delta T \lambda_0^5}{\Delta \lambda} \exp\left(\frac{a}{\lambda_0 T} - 1\right) \right] \quad (10)$$

Figure 4A:
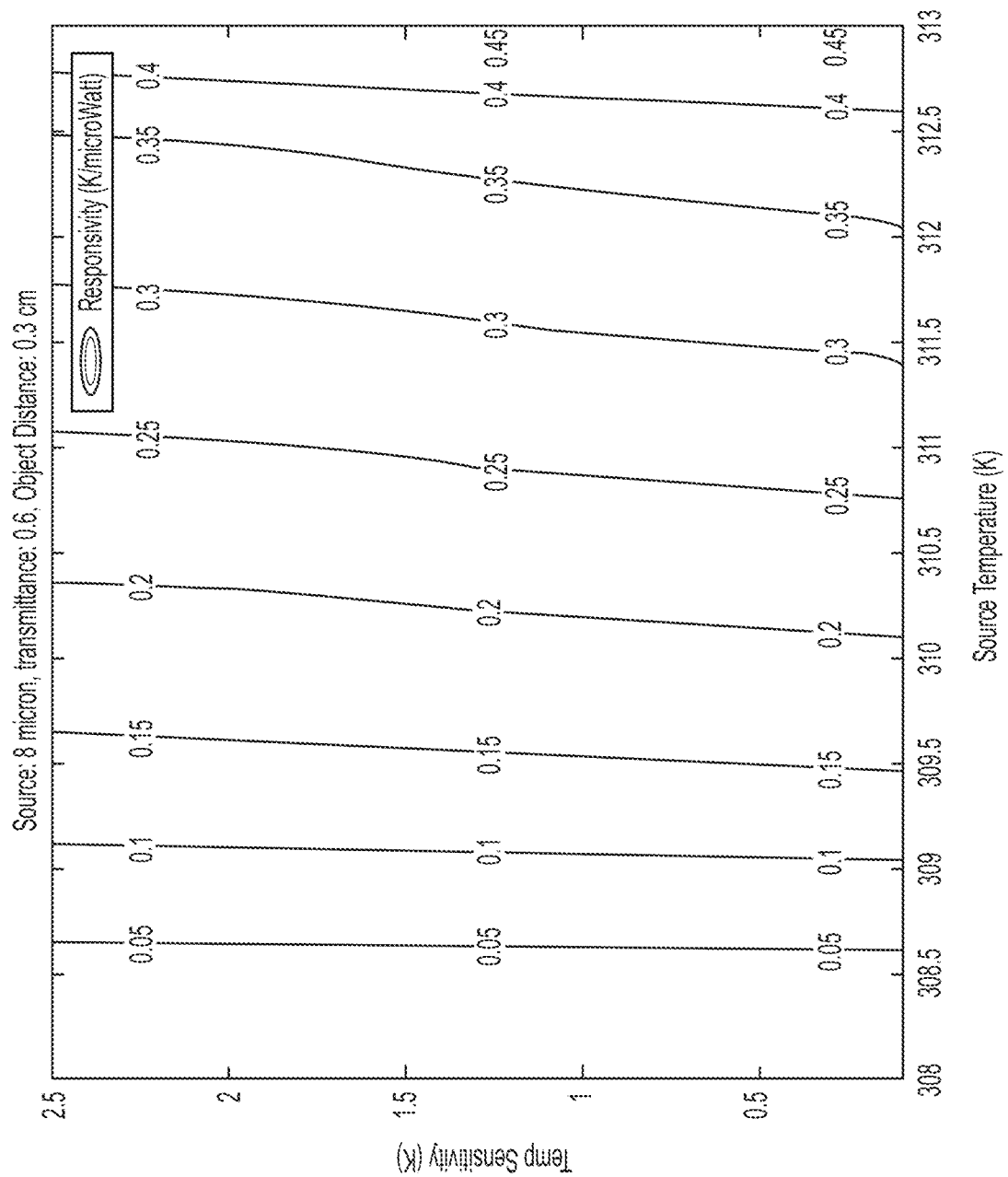
FIG. 4A is a plot showing detector responsivity R contours as a function of the source Temperature (T) and temperature sensitivity (ΔT) at a given source wavelength, air transmittance and object distance.
Figure 4B:
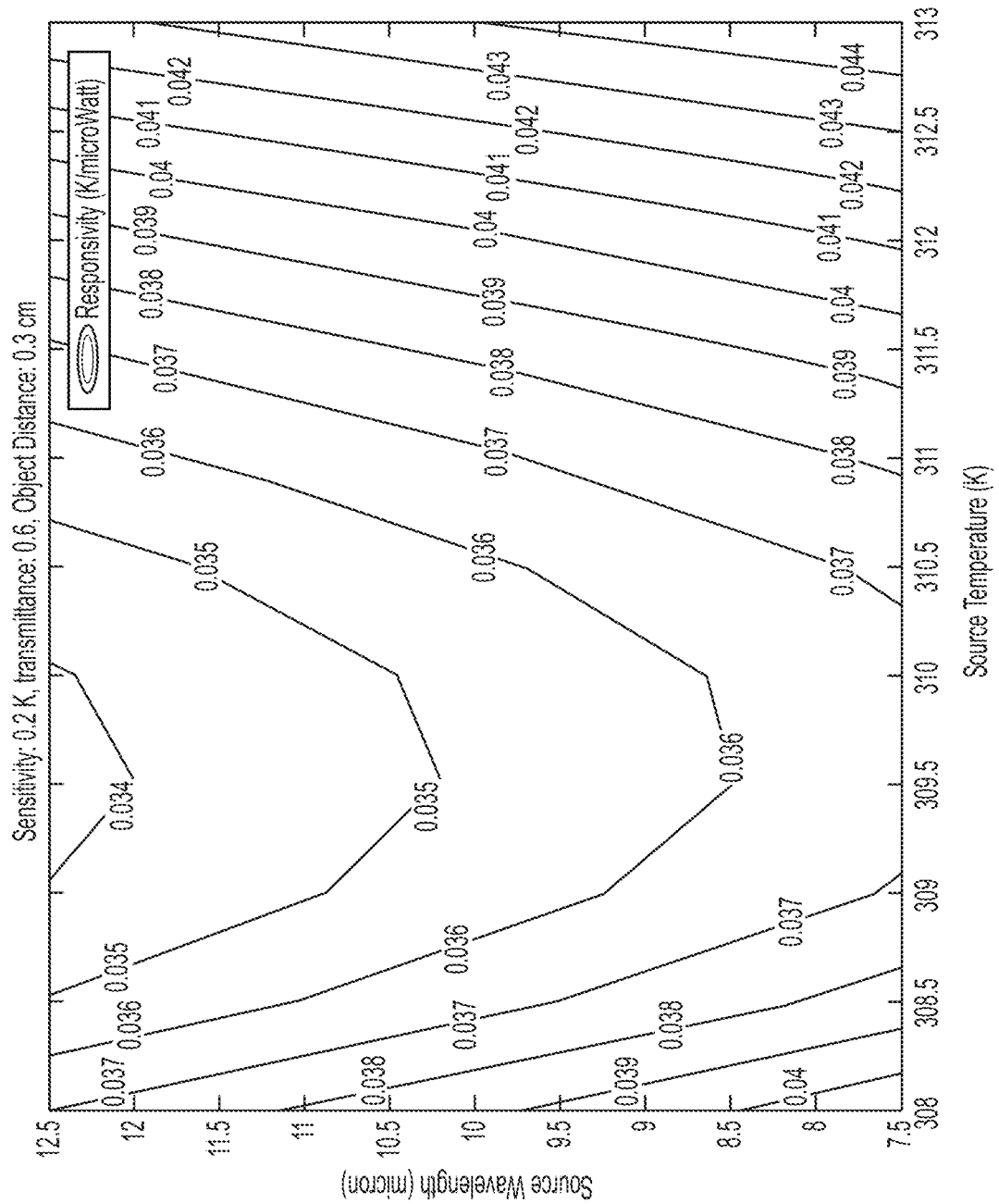
FIG. 4B is a plot depicting detector responsivity contours as a function of the source Temperature (T) and source wavelength (λ) at a given temperature sensitivity, air transmittance and object distance.
Figure 4C:
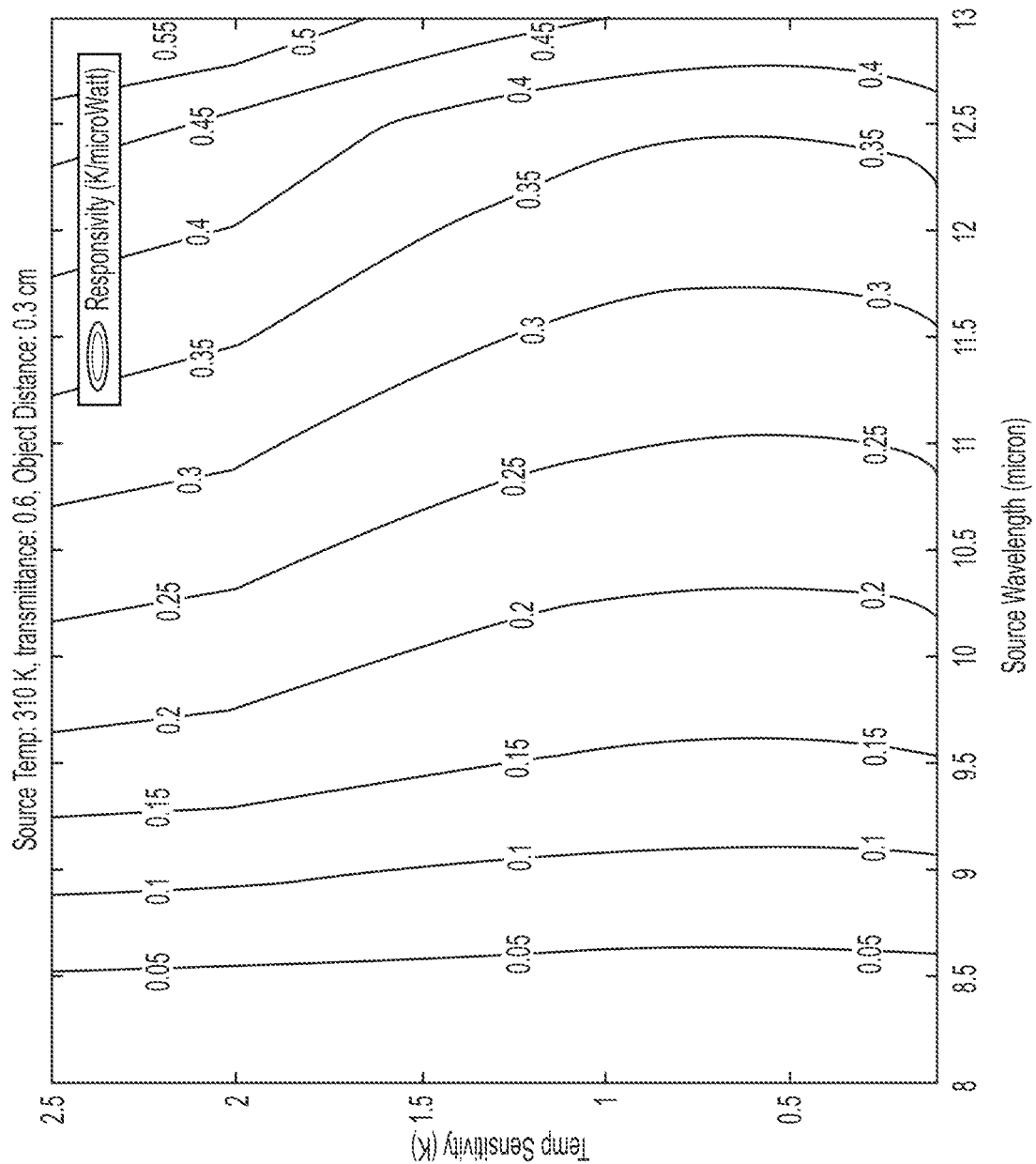
FIG. 4C is a plot showing detector responsivity contours as a function of the source wavelength (λ) and temperature sensitivity (ΔT) at a given source temperature, air transmittance and object distance.

As shown in FIG. 4A, the responsivity contours vary from 50-450 mK per microwatt. The responsivity at body temperature (310K) is 200 mK per micro Watt of the incident IR power, which is sufficient to overcome the NET of the detector. The lower bound of the incident IR wavelength was kept at 8 μm. FIG. 4B shows detector responsivity at the body temperature is in the range of 85-110 mK per micro Watt of the incident IR power with incident IR wavelength of 7.5-12.5 μm, which is enough to overcome the NET of the detector. FIG. 4C depicts the responsivity contours at the body temperature (310K) vary from 50-450 mK per microwatt. The responsivity at the wavelength corresponding to the maximal emitted IR power (e.g., the wavelength of 10 μm) is 200 mK per micro Watt of the incident IR power, which is enough to overcome the NET of the detector.

In certain embodiments, the present system is operated at a temperature lower than ambient temperature. In certain embodiments, the present system is operated at about room temperature (e.g., about 23° C.) or about physiological temperature (e.g., about 37° C.). The cells and the infrared camera may be substantially at the same temperature. Thermal noise may be decreased by lowering the operating temperature. Cells and the infrared imaging camera are at a temperature below 50° C. or below 15° C. or below 5° C.

In certain embodiments, IR detectors may operate with mid-IR at a small noise equivalent temperature (order of 10-100 mK) as compared to the natural temperature distribution (order of 1-10 K) and thermal resolution (order of 0.1-1 K) across different cellular and subcellular components of the tissue under examination.

In certain embodiments, the device may detect cancer volume, by generating 3-D images. Multiple images parallel to local epithelial surface (noninvasive/minimally invasive), or multiple images perpendicular to the local epithelium (minimally invasive) may create 3-D images. From the cancer volume, the maximum area and depth of cancer invasion may be determined.

In certain embodiments, the infrared imaging device for image acquisition is noninvasive (e.g., for superficial examination on skin to judge cancers in epidermis-BCC/SCC/Melanoma). The infrared imaging device may comprise a minimally noninvasive extension (e.g., an attachment to endoscopy/colonoscopy/colposcopy devices to examine Esophagus/Stomach/Colon/Uterus/Cervix).

In certain embodiments, the system operates at ambient or near ambient temperature.

Figure 25:
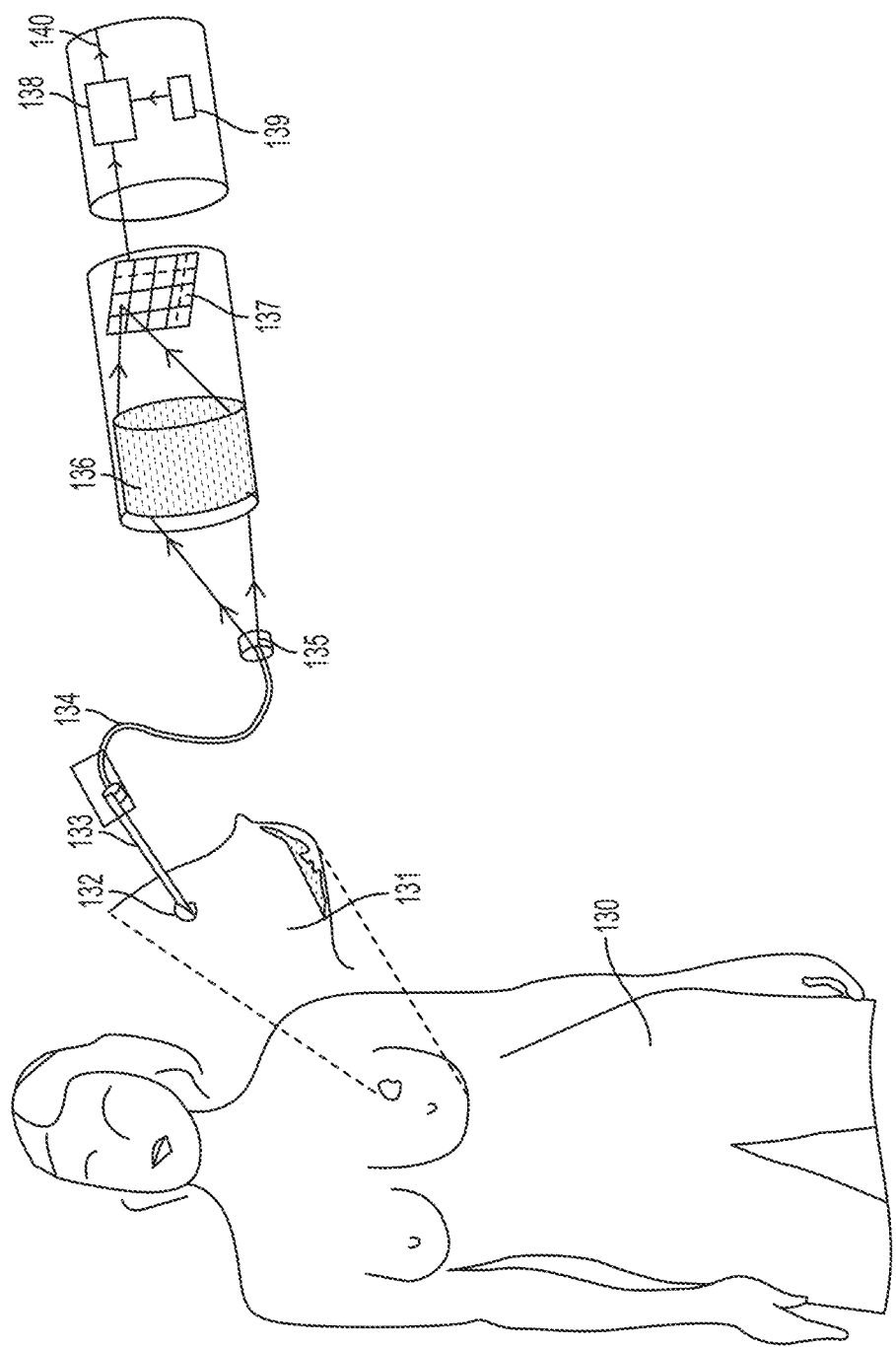
FIG. 25 illustrates an exemplary device for breast cancer detection. The device comprises an attachment (e.g., a biopsy needle) to access cells/tissues in internal sites of the breast.
Figure 26:
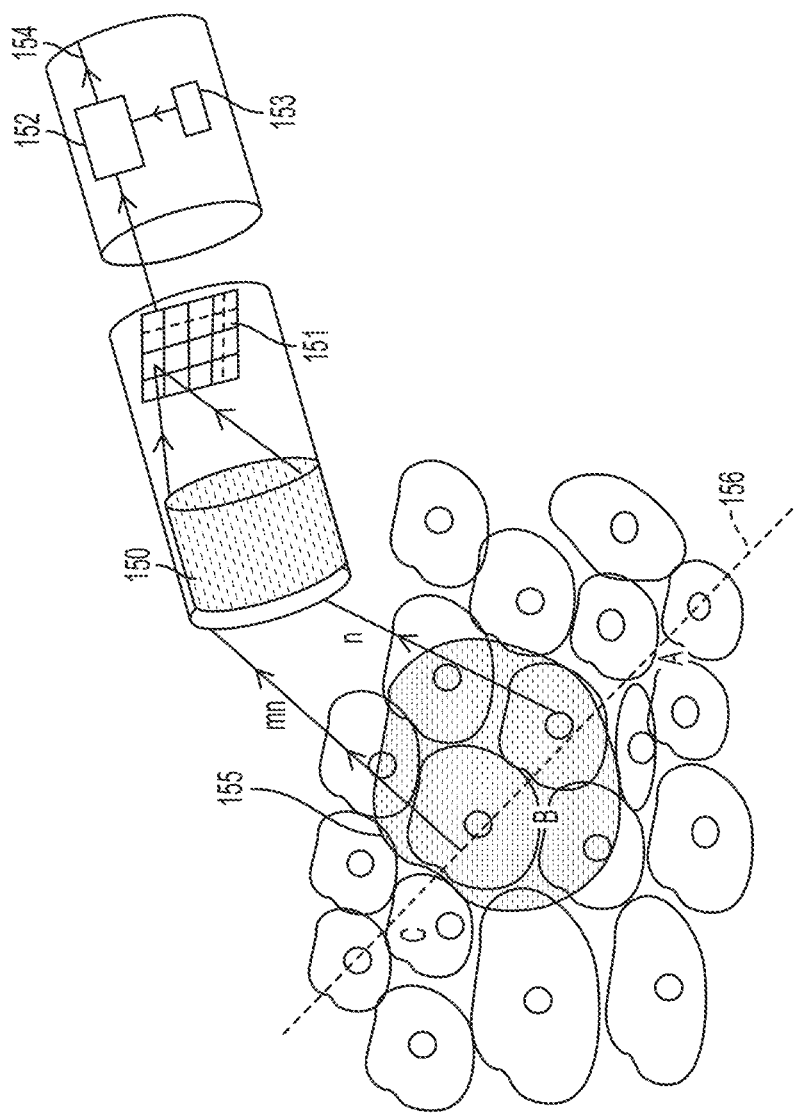
FIG. 26 illustrates an exemplary device for detecting a cancer boundary during a surgical operation. The device comprises a standard surgical imaging system or a hollow surgical biopsy needle.

In certain embodiments, the system/apparatus comprise one or more attachments, which assist in locating IR detector or collector nearby an area to be analyzed or diagnosed. In certain embodiments, the system/apparatus comprises a biopsy needle. For example, an apparatus to analyze a cell/tissue in a breast may have a biopsy needle as shown in FIG. 25. The needle (4) may have one or more channels. The needle channel is used to pass the signal (6) emitted from the breast tumor (3) to the 2-D detector. In certain embodiments, the system/apparatus comprises a standard surgical imaging system (e.g., LENS surgical system from Smith & Nephew, OEC from GE, 0-arm from Medtronic). In certain embodiments, the system/apparatus comprises a hollow surgical biopsy needle. As shown in FIG. 26, the device may work as an apparatus to detect the cancer boundary during surgical operation (e.g., biopsy). The needle or fiber may be used to pass the IR (m,n) emitted from different zones (A, B, C) of the cells/ tissues (1) to the 2-D detector which compares the normality status for zones A, B, C and determines where the cancer boundary or edge is located with high spatial resolution (e.g., cellular resolution, 1-10 micron).

Figure 23:
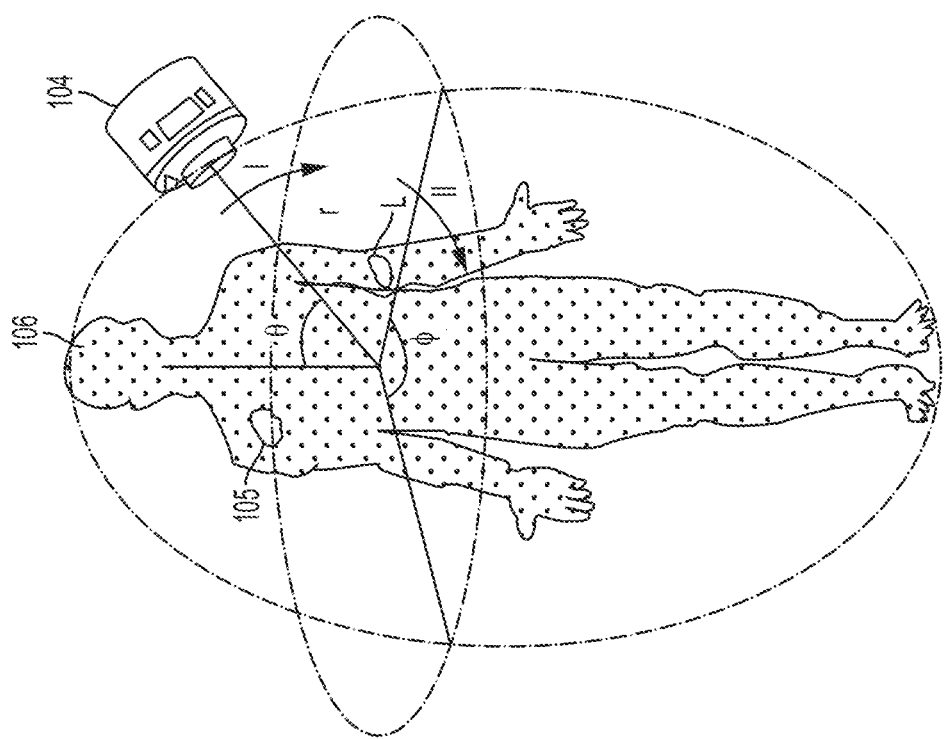
FIG. 23 illustrates an exemplary device for a full body scanner for detecting cancer.
Figure 24:
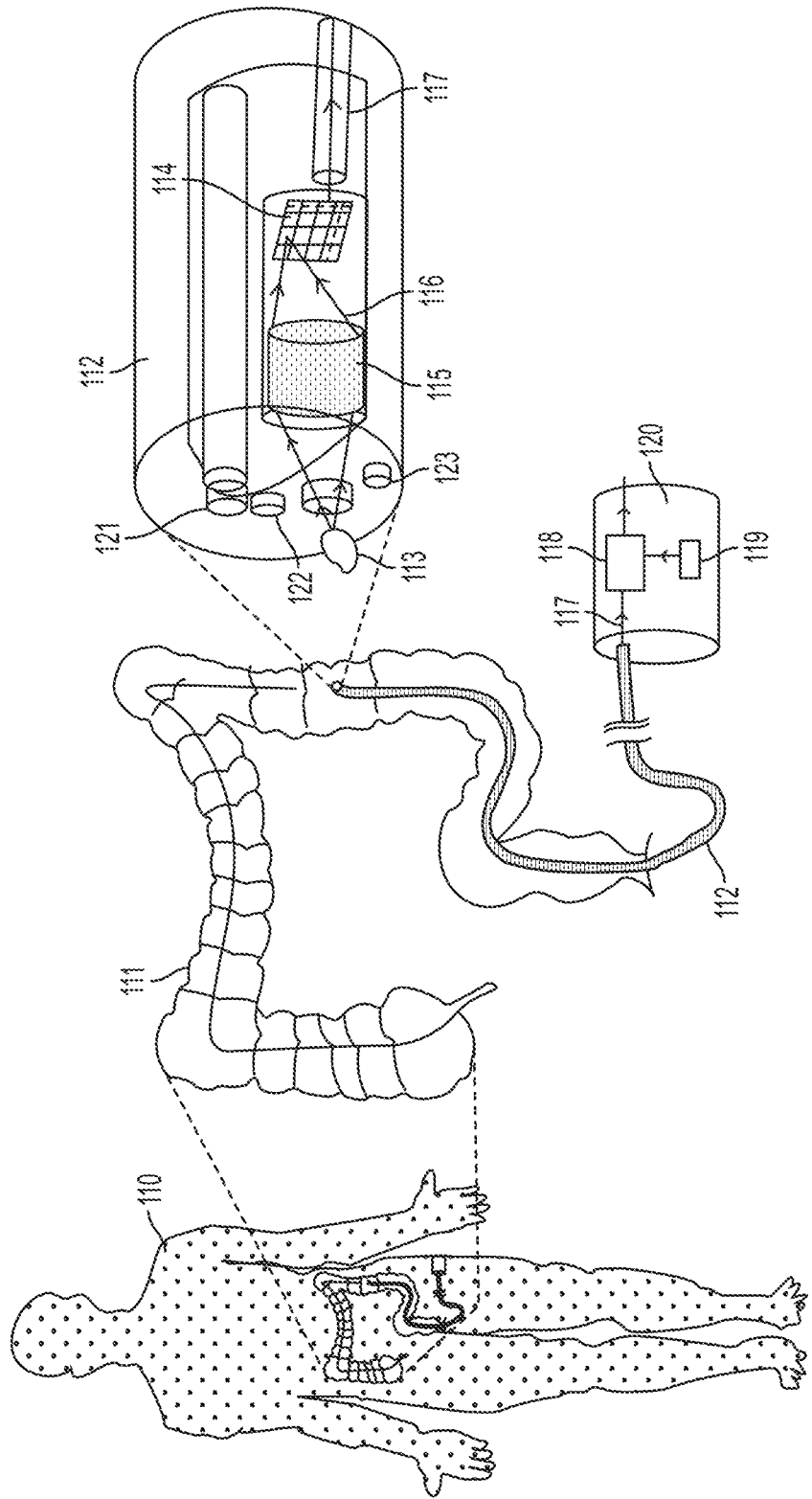
FIG. 24 illustrates an exemplary device for cancer detection from internal sites of a subject (e.g., not from skin).

In certain embodiments, the systems and methods described herein provide for features in vivo imaging of a subject. The systems and methods allow for the recording of multiple biological processes, functions or targets (FIGS. 23-25). The approach described herein can also be used to follow therapy for such diseases by imaging molecular events and biological pathways modulated by such therapy, including but not limited to determining efficacy, optimal timing, optimal dosing levels (including for individual patients or test subjects), pharmacodynamic parameters, and synergistic effects of combinations of therapy.

The systems and methods described herein can be used to help a physician, surgeon, or other medical personnel to identify and characterize areas of disease, such as arthritis, cancers, metastases or vulnerable or unstable plaque, to distinguish diseased and normal tissue, such as detecting tumor margins that are difficult to detect.

The approaches for IR imaging described herein can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring and/or development of drug therapy and delivery, including cell based therapies.

The systems and methods described herein can also be used in prognosis of a disease or disease condition. The systems and methods described herein can therefore be used, for example, to determine the presence of tumor cells and localization and metastases of tumor cells, the presence and localization of inflammation, including the presence of activated macrophages, for instance in atherosclerosis, arthritis, gout, or cellulitis, the presence and localization of vascular disease including areas at risk for acute occlusion (e.g., vulnerable plaques) in coronary and peripheral arteries, regions of expanding aneurysms, and unstable plaque in carotid arteries, and ischemic areas. The systems and methods described herein can also be used in identification and evaluation of cell death, injury, apoptosis, necrosis, hypoxia and angiogenesis. The systems and methods described herein can also be used in for monitoring trafficking and localization of certain cell types, including T-cells, tumor cells, immune cells, stem cells, and other cell types. In particular, this method may be used to monitor cell based therapies or cytology based diagnostics.

Figure 30:
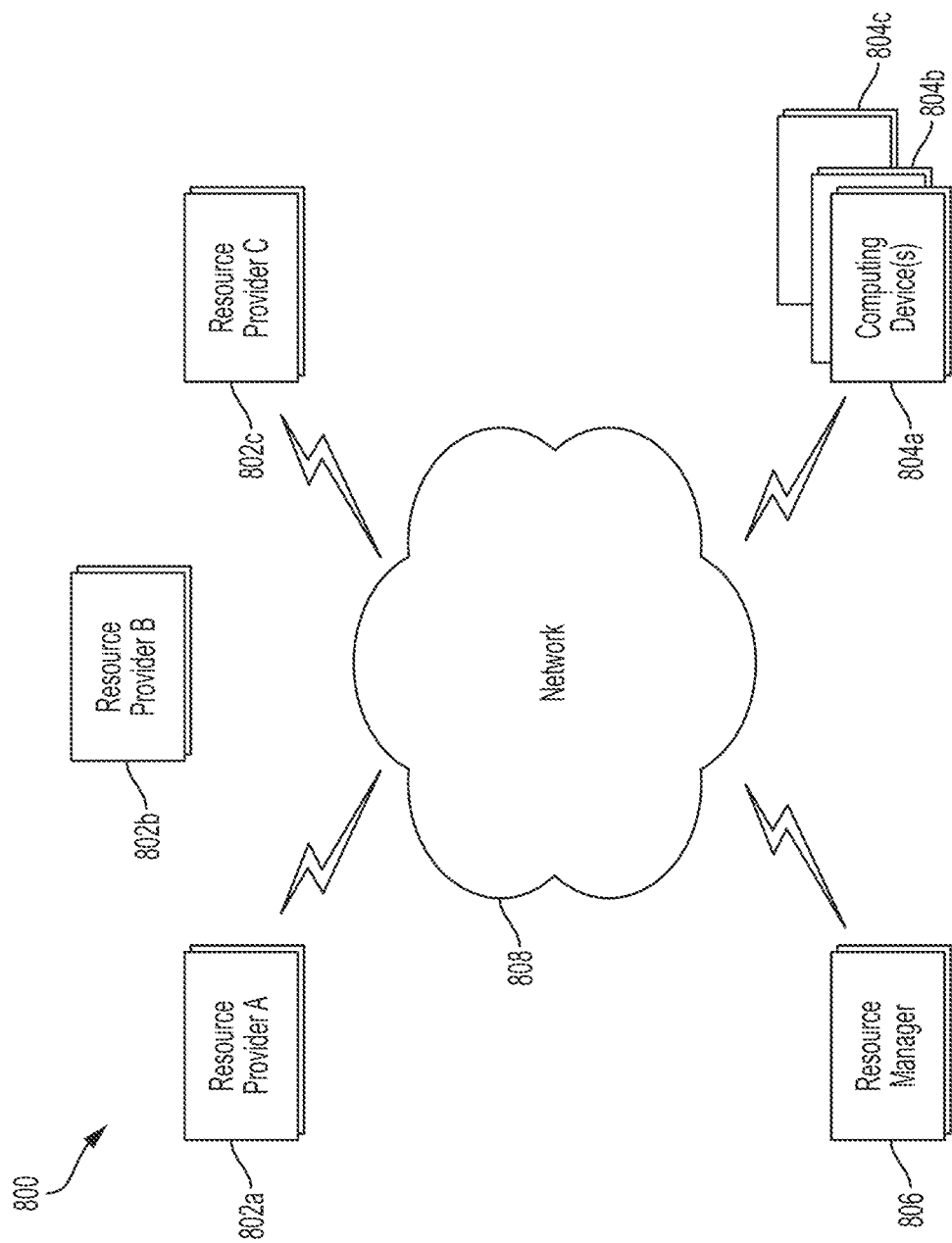
FIG. 30 is a block diagram of an example network environment for use in the methods and systems described herein, according to an illustrative embodiment.

As shown in FIG. 30, an implementation of a network environment 800 for use in providing systems and methods for cancer detection as described herein. In brief overview, a block diagram of an exemplary cloud computing environment 800 is shown and described. The cloud computing environment 800 may include one or more resource providers 802a, 802b, 802c (collectively, 802). Each resource provider 802 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 802 may be connected to any other resource provider 802 in the cloud computing environment 800. In some implementations, the resource providers 802 may be connected over a computer network 808. Each resource provider 802 may be connected to one or more computing device 804a, 804b, 804c (collectively, 804), over the computer network 808.

The cloud computing environment 800 may include a resource manager 806. The resource manager 806 may be connected to the resource providers 802 and the computing devices 804 over the computer network 808. In some implementations, the resource manager 806 may facilitate the provision of computing resources by one or more resource providers 802 to one or more computing devices 804. The resource manager 806 may receive a request for a computing resource from a particular computing device 804. The resource manager 806 may identify one or more resource providers 802 capable of providing the computing resource requested by the computing device 804. The resource manager 806 may select a resource provider 802 to provide the computing resource. The resource manager 806 may facilitate a connection between the resource provider 802 and a particular computing device 804. In some implementations, the resource manager 806 may establish a connection between a particular resource provider 802 and a particular computing device 804. In some implementations, the resource manager 806 may redirect a particular computing device 804 to a particular resource provider 802 with the requested computing resource.

Figure 31:
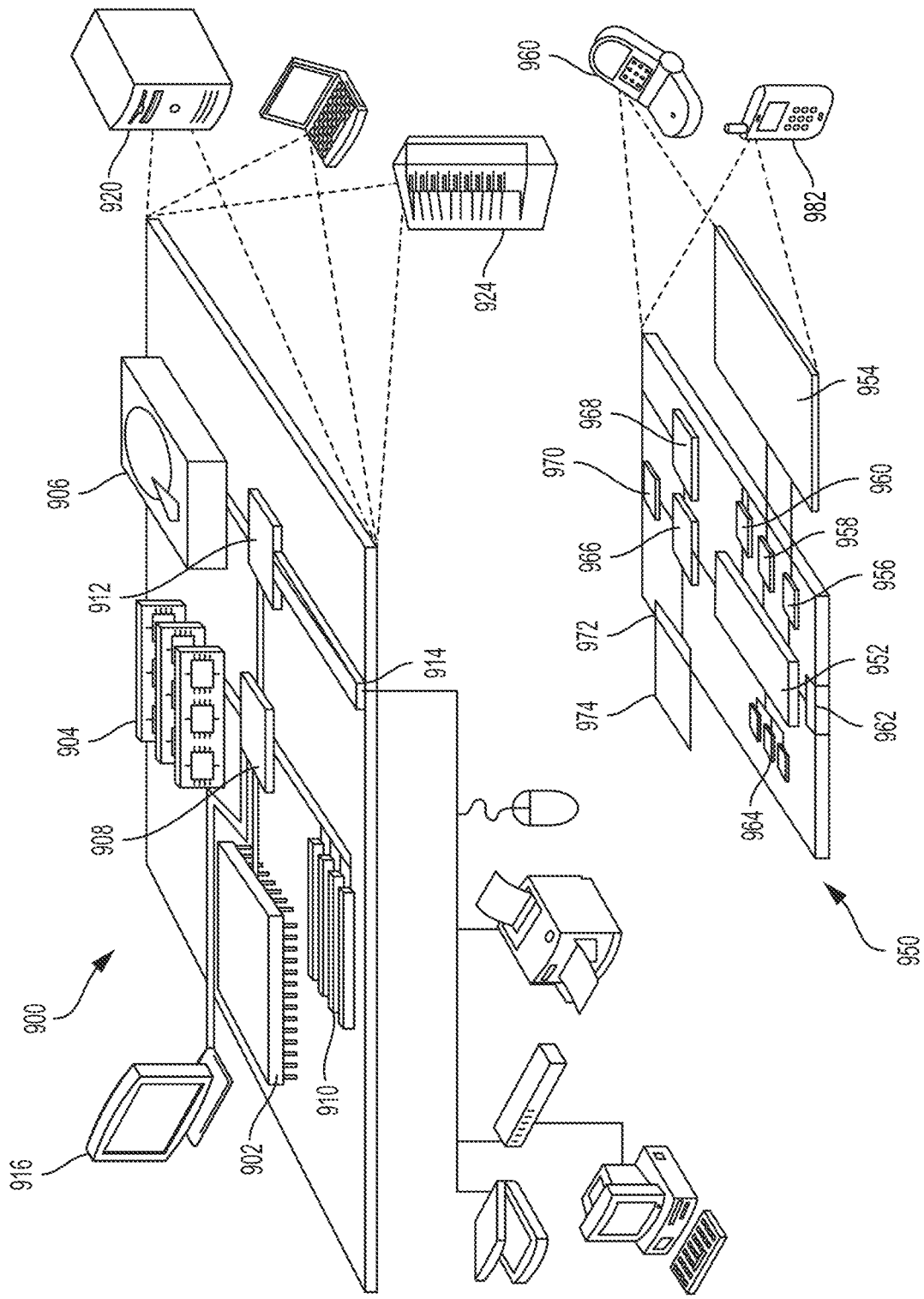
FIG. 31 is a block diagram of an example computing device and an example mobile computing device, for use in illustrative embodiments of the invention.

FIG. 31 shows an example of a computing device 900 and a mobile computing device 950 that can be used to implement the techniques described in this disclosure. The computing device 900 is intended to represent various forms of digital computers, such as laptops, desktops, workstations, personal digital assistants, servers, blade servers, mainframes, and other appropriate computers. The mobile computing device 950 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 900 includes a processor 902, a memory 904, a storage device 906, a high-speed interface 908 connecting to the memory 904 and multiple high-speed expansion ports 910, and a low-speed interface 912 connecting to a low-speed expansion port 914 and the storage device 906. Each of the processor 902, the memory 904, the storage device 906, the high-speed interface 908, the high-speed expansion ports 910, and the low-speed interface 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as a display 916 coupled to the high-speed interface 908. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 904 stores information within the computing device 900. In some implementations, the memory 904 is a volatile memory unit or units. In some implementations, the memory 904 is a non-volatile memory unit or units. The memory 904 may also be another form of computer-readable medium, such as a magnetic or optical disk.

The storage device 906 is capable of providing mass storage for the computing device 900. In some implementations, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 902), perform one or more methods, such as those described above. The instructions can also be stored by one or more storage devices such as computer- or machine-readable mediums (for example, the memory 904, the storage device 906, or memory on the processor 902).

The high-speed interface 908 manages bandwidth-intensive operations for the computing device 900, while the low-speed interface 912 manages lower bandwidth-intensive operations. Such allocation of functions is an example only. In some implementations, the high-speed interface 908 is coupled to the memory 904, the display 916 (e.g., through a graphics processor or accelerator), and to the high-speed expansion ports 910, which may accept various expansion cards (not shown). In the implementation, the low-speed interface 912 is coupled to the storage device 906 and the low-speed expansion port 914. The low-speed expansion port 914, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. In addition, it may be implemented in a personal computer such as a laptop computer 922. It may also be implemented as part of a rack server system 924. Alternatively, components from the computing device 900 may be combined with other components in a mobile device (not shown), such as a mobile computing device 950. Each of such devices may contain one or more of the computing device 900 and the mobile computing device 950, and an entire system may be made up of multiple computing devices communicating with each other.

The mobile computing device 950 includes a processor 952, a memory 964, an input/output device such as a display 954, a communication interface 966, and a transceiver 968, among other components. The mobile computing device 950 may also be provided with a storage device, such as a micro-drive or other device, to provide additional storage. Each of the processor 952, the memory 964, the display 954, the communication interface 966, and the transceiver 968, are interconnected using various buses, and several of the components may be mounted on a common motherboard or in other manners as appropriate.

The processor 952 can execute instructions within the mobile computing device 950, including instructions stored in the memory 964. The processor 952 may be implemented as a chipset of chips that include separate and multiple analog and digital processors. The processor 952 may provide, for example, for coordination of the other components of the mobile computing device 950, such as control of user interfaces, applications run by the mobile computing device 950, and wireless communication by the mobile computing device 950.

The processor 952 may communicate with a user through a control interface 958 and a display interface 956 coupled to the display 954. The display 954 may be, for example, a TFT (Thin-Film-Transistor Liquid Crystal Display) display or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may provide communication with the processor 952, so as to enable near area communication of the mobile computing device 950 with other devices. The external interface 962 may provide, for example, for wired communication in some implementations, or for wireless communication in other implementations, and multiple interfaces may also be used.

The memory 964 stores information within the mobile computing device 950. The memory 964 can be implemented as one or more of a computer-readable medium or media, a volatile memory unit or units, or a non-volatile memory unit or units. An expansion memory 974 may also be provided and connected to the mobile computing device 950 through an expansion interface 972, which may include, for example, a SIMM (Single In Line Memory Module) card interface. The expansion memory 974 may provide extra storage space for the mobile computing device 950, or may also store applications or other information for the mobile computing device 950. Specifically, the expansion memory 974 may include instructions to carry out or supplement the processes described above, and may include secure information also. Thus, for example, the expansion memory 974 may provide as a security module for the mobile computing device 950, and may be programmed with instructions that permit secure use of the mobile computing device 950. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 952), perform one or more methods, such as those described above. The instructions can also be stored by one or more storage devices, such as one or more computer- or machine-readable mediums (for example, the memory 964, the expansion memory 974, or memory on the processor 952). In some implementations, the instructions can be received in a propagated signal, for example, over the transceiver 968 or the external interface 962.

The mobile computing device 950 may communicate wireles sly through the communication interface 966, which may include digital signal processing circuitry where necessary. The communication interface 966 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 968 using a radio-frequency. In addition, short-range communication may occur, such as using a Bluetooth®, Wi-FiTM, or other such transceiver (not shown). In addition, a GPS (Global Positioning System) receiver module 970 may provide additional navigation- and location-related wireless data to the mobile computing device 950, which may be used as appropriate by applications running on the mobile computing device 950.

The mobile computing device 950 may also communicate audibly using an audio codec 960, which may receive spoken information from a user and convert it to usable digital information. The audio codec 960 may likewise generate audible sound for a user, such as through a speaker, e.g., in a handset of the mobile computing device 950. Such sound may include sound from voice telephone calls, may include recorded sound (e.g., voice messages, music files, etc.) and may also include sound generated by applications operating on the mobile computing device 950.

The mobile computing device 950 may be implemented in a number of different forms, as shown in the FIG. 31. For example, it may be implemented as a cellular telephone 980. It may also be implemented as part of a smart-phone 982, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While apparatus, systems, and methods have been particularly shown and described with reference to specific preferred embodiments, it should be understood by those skilled in the art that various changes in form and detail may be made therein without departing from the spirit and scope of the invention as defined by the appended claims.

EXAMPLES

Example 1: Validation Study

The present example describes a validation study of the methods described herein.

For this study, diagnosed and annotated H&E images of tumor slices were purchased from Leeds university hospital for this validation study. The images were from patients who suffered BCC and/or SCC. Each image typically contains 100-500 field of views. A blind pool of 1000 samples from the H&E images was taken randomly. One sample was a field of view of an H&E image of a tumor. Each field of view typically contained 500-1000 cells, but at least 100 cells. The samples did not have a damaged or torn part or cell debris from tissue fixing.

As described above, each of the cells in the pool was segmented into the cellular area and the nuclear area. Then, the nuclear area feature and the nuclear contrast feature of each cell were calculated to obtain the information surface value. The diagnostic scores were derived from (1) the ensemble average of local specific heats among cells in each of the subgroups sorted by the information surface values (e.g., specificity index) and (2) the junction curvature of the curve of $<C_L>$ vs L (e.g., shape feature). The calculated diagnostic scores were compared with the pre-determined reference diagnostic scale. The statistical values are summarized in Table 1.

For the identification of skin cancer spectra, the present method identified cancer cells over normal cells with high sensitivity and specificity without false positive (FP) or false negative (FN). Additionally, the present method diagnosed Malignant Melanoma including subtleties with high sensitivity and specificity. For BCC cases, there were 25 false positives (due to 25 SCC cases misidentified as BCC) and no false negatives. For SCC case, there were 25 false negatives (due to 25 SCC cases misidentified as BCC) and no false positives.

The ratios of the true positive rate to the false positive rate (slope of the ROC curve) for all four types of cancer detection were $\gg 1$.

TABLE 1

| Diagnosis (1000 samples) | True positive (TP) | True negative (TN) | False positive (FP) | False negative (FN) | Sensitivity (TP/ (TP + FN)) | Specificity (TN/ (TN + FP)) | ROC curve slope (TP-rate/ FP rate) |
|---|---|---|---|---|---|---|---|
| Cancer vs Normal | 800 | 200 | 0 | 0 | 100% | 100% | ∞ (>>1) |
| MM (including subtleties) | 400 | 600 | 0 | 0 | 100% | 100% | ∞ (>>1) |
| BCC (including subtleties) | 200 | 775 | 25 | 0 | 100% | 90% | 80 (>>1) |
| SCC (including subtleties) | 175 | 800 | 0 | 25 | 97% | 100% | ∞ (>>1) |

Example 2: Diagnosis of Fibroepitheliomas of Pinkus

The present example describes, among other things, exemplary cancer detection.

A patient presented with a history of a slowly enlarging growth on the lower back. On examination, a dome-shaped, sessile, flesh-colored lesion was identified. The patient was referred to dermatology specialist services. Dermoscopy was suspicious and the lesion was fully excised for diagnostic purposes. Histopathological assessment revealed a fibroepithelioma of Pinkus, which had been resected with clear surgical margins. Fibroepitheliomas of Pinkus are rare variants of basal cell carcinoma that present as poorly pigmented, exophytic, slow-growing skin lesions which typically affect the lower trunk. Fibroepitheliomas of Pinkus are recognized mimics of common benign skin lesions such as fibroepithelial polyps, dermal nevi or seborrheic keratosis and therefore often risk being overlooked clinically. However, Fibroepitheliomas of Pinkus can be successfully diagnosed by dermoscopy (circa 90% of cases), typically followed by histopathological confirmation. Microscopically, Fibroepitheliomas of Pinkus feature multiple, thin anastomosing cords of basaloid epithelial cells extending into the underlying dermis, entrapping fibrotic stroma which are thought to initial invasion along eccrine ducts. Like other basal cell carcinomas, fibroepitheliomas of Pinkus generally follow an indolent course but can be locally aggressive, although they do not metastasize. Treatment is typically by surgical excision.

Figure 11A:
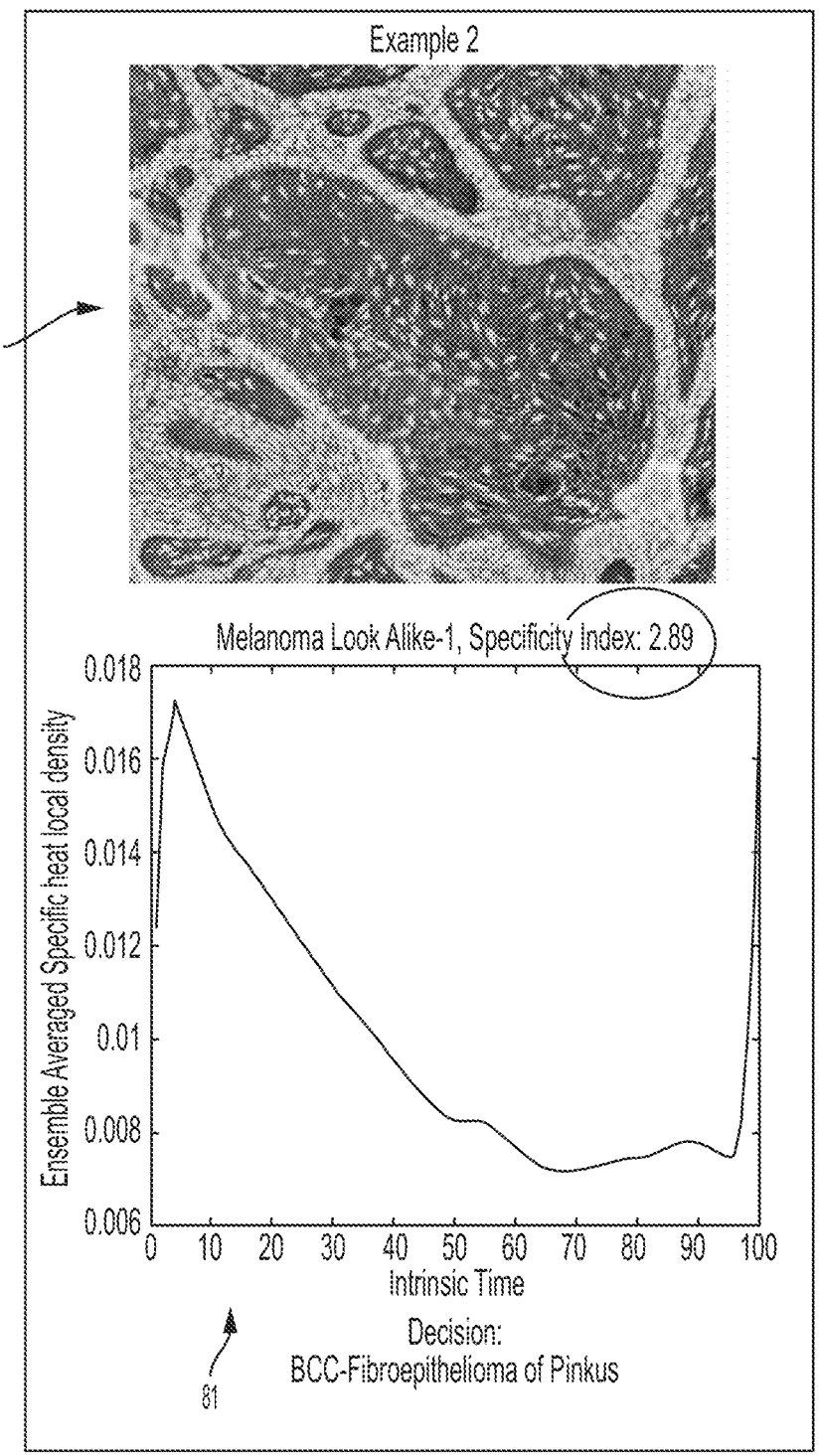

As shown in FIG. 11A, the present example is an illustrative case for the strength of the systems/methods in the present disclosure, which has been developed to distinguish between a range of benign and malignant cutaneous lesions. This lesion was posed as a deliberate challenge since the present system had not previously been exposed to a fibroepithelioma of Pinkus. The present system correctly concluded that the sample was basal cell carcinoma after independent and blinded review of the case. The distinction between more common variants of basal cell carcinoma and fibroepitheliomas of Pinkus is morphological, but from a management and prognostication perspective, the distinction is largely academic as their behavior is comparable. This example serves to highlight that the present system/method is capable of recognizing key cytological features that are intrinsic to basal cell carcinomas regardless of the overall appearance/histoarchitecture of the tumor. In certain embodiments, the present system not only is able to distinguish between benign and malignant lesions, but also is able to differentiate common lesions from more aggressive cutaneous malignancies such as squamous cell carcinomas and melanomas, which both have a metastatic potential and carry a worse prognosis. It is important that the present system/method does not rely on variations in intrinsic tumor architecture. Indeed, despite usually being a useful diagnostic aid to diagnosticians, tumor architecture can also occasionally prove to be a histopathological diagnostic pitfall and result in misdiagnoses (e.g., in failing to distinguish between Spitz nevi, nodular basal cell carcinomas and malignant melanomas).

Example 3: Diagnosis of Basosquamous Carcinoma

A patient presented with a right-sided nodular, scaly and very focally ulcerated lesion affecting the preauricular skin (FIG. 11B). Dermoscopy revealed the lesion to be suspicious and it was surgically excised. Histological evaluation revealed a heterogeneous epidermal tumor consisting of hyperchromatic basaloid cells with palisading separated by an abrupt transition zone from a component with eosinophilic squamous differentiation and evident cytological atypia. There was no evidence of lymphovascular space invasion or perineural involvement in the planes of section, and the surgical resection margins were free of tumor. The diagnosis of basosquamous carcinoma was confirmed according to variable Ber-EP4 immunopositivity across the lesion constituents.

Basosquamous carcinoma is a relatively common but unusual epidermal malignancy with morphological features that are a composite of both basal cell and squamous cell carcinomas. It is not a collision carcinoma involving two distinct entities but rather involves morphologically distinct clonal subpopulations within the same tumor. However, its behavior is reminiscent of squamous cell carcinoma insofar as it is more locally invasive, aggressive, and has a higher propensity for metastasis than basal cell carcinoma. Accordingly, it carries a worse prognosis and warrants longer-term follow-up.

In this Example, the present system/method appropriately identified both components of the lesion in different areas, highlighting the fact that this was not a simple basal cell carcinoma, but instead a basosquamous carcinoma. Although this is not necessarily a challenging diagnosis for the histopathologist, rapid diagnostic confirmation of the nature of the lesion obviates the need for further immunohistochemical assessment. As such, for more subtle lesions or where the diagnosis may remain problematic due to limited tumor representation in the planes of section, the present system/method offers the clear benefit of reducing the turnaround times allied with requiring further levels or the immunohistochemical assessment of heterogeneous Ber-EP4 positivity.

Example 4: Diagnosis of Lentigo Maligna

A patient presented with a slow-growing 2×1.5 cm pigmented, flat lesion on the left side of the face on an area of sun-damaged skin in conjunction with other lesions with appearances in keeping with seborrheic keratosis (FIG. 11C). Dermoscopy was equivocal and, given the size of the lesion, a punch biopsy was obtained for diagnostic purposes. Histopathological evaluation revealed a contiguous population of atypical melanocytes scattered along the dermoepidermal junction extending to the margins of the biopsy and overlying a dermis with prominent solar elastosis. Complete excision of the lesion was subsequently performed.

Lentigo malignas are a subtype of melanoma in situ (i.e., non-invasive), and thus considered by some to be premalignant—compare lentigo maligna melanoma which demonstrates invasion into the underlying dermis. Progression to lentigo maligna melanoma is low, typically <5%. One of the difficulties with the macroscopic and dermoscopic evaluation of lentigo maligna is that it can commonly associate with other, pigmented benign cutaneous lesions of sun-damaged skin, such as lentigines and lentigo senilis. As a result, diagnosis is typically based on histopathological assessment. Moreover, due to the fact that they are flat, broadly unremarkable, slow-growing lesions in the main, patients may present late, by which time lesions are usually too large to be eligible for excision biopsy given the uncertainty of the diagnosis. As a result, these are frequently diagnosed by punch biopsy initially, as in this case, with wider excision/Mohs surgery with/without imiquimod therapy subsequently, as appropriate.

In this example, the present system/method was able to identify the populations of atypical melanocytes. The diagnostic challenge in this instance, where the algorithm would prove helpful, is in the identification of the distribution of atypical melanocytes with a view to identifying truly negative margins. Difficulties in determining the presence of truly negative margins are, expectedly, a contributory factor to recurrence.

Example 5: Blind Study

Figure 11D:
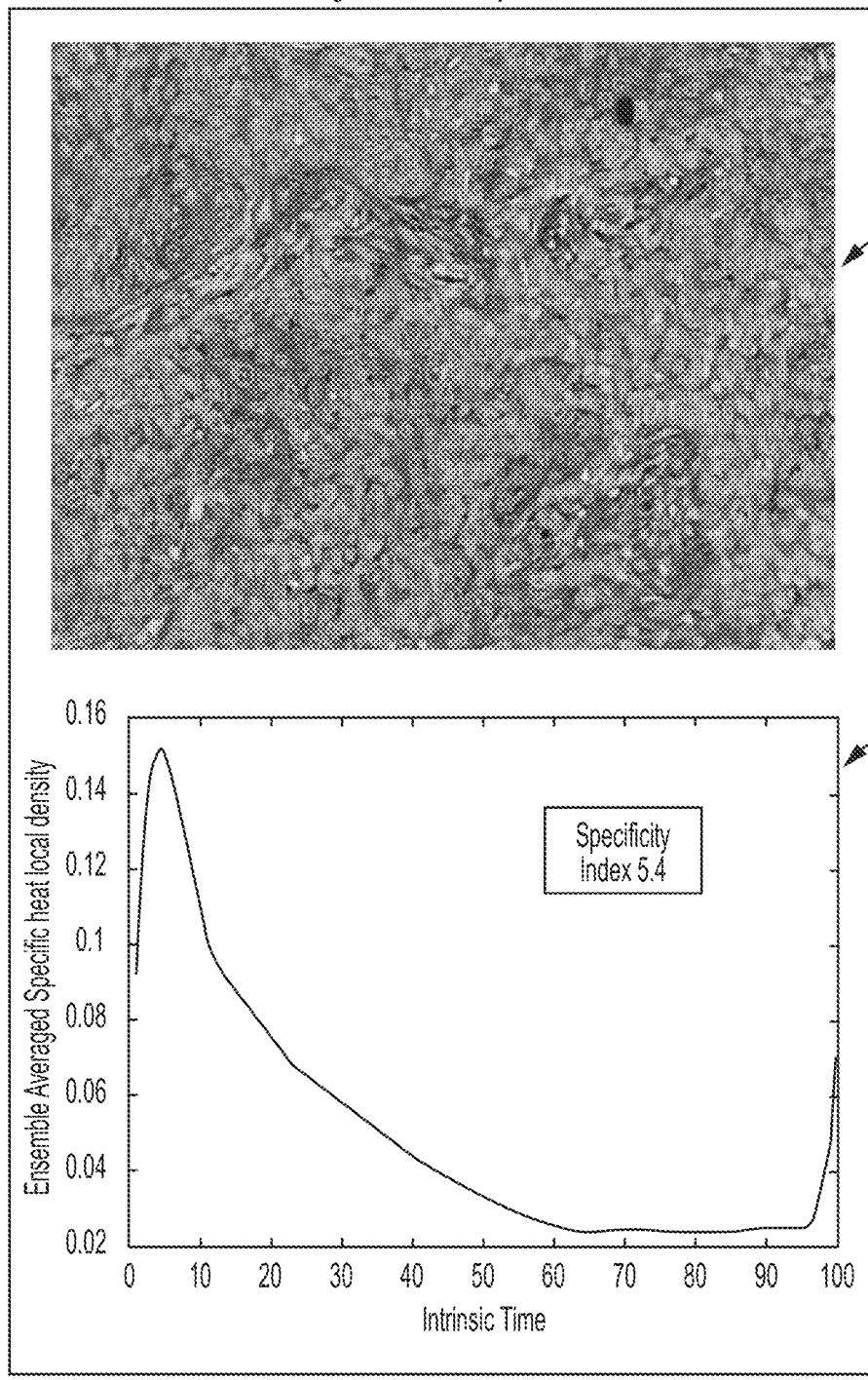
FIG. 11D shows blind diagnosis of poorly differentiated squamous cell carcinoma (SCC) with dentritic Melanocytes—a Melanoma mimic as described in Example 5.
Figure 12A:
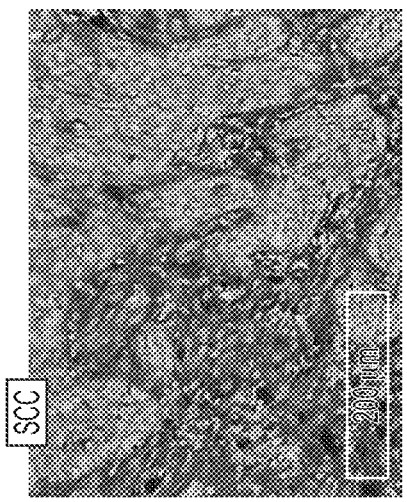
Figure 12B:
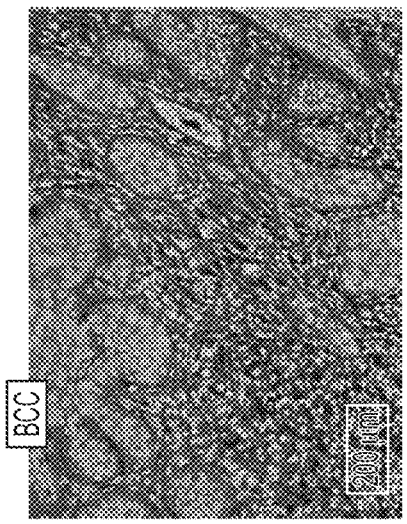
Figure 12C:
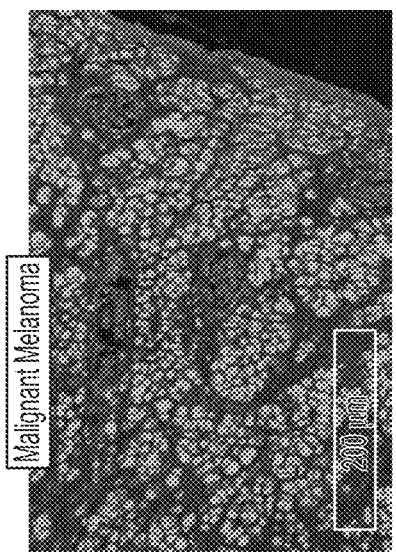
Figure 12D:
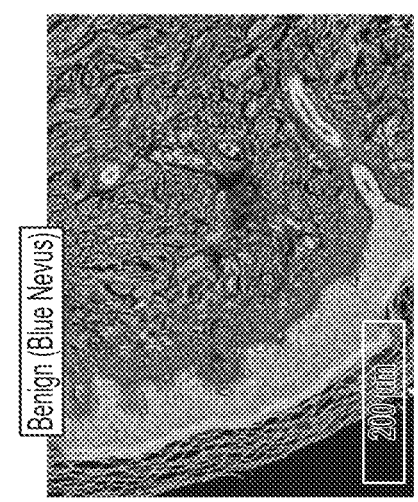
Figure 12E:
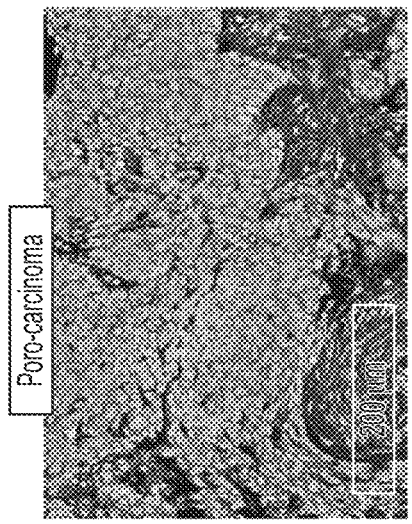
Figure 12F:
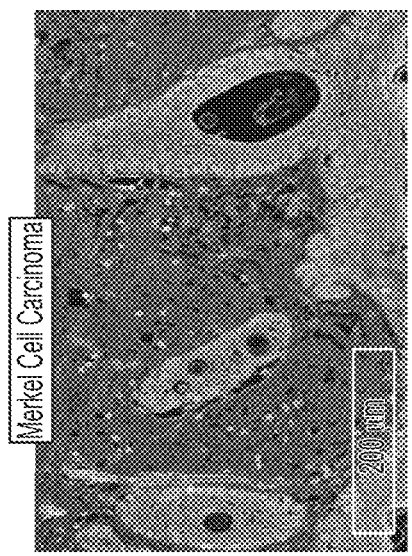
Figure 13C:
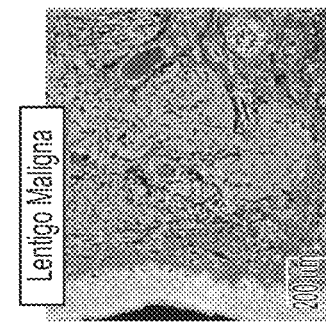
Figure 13G:
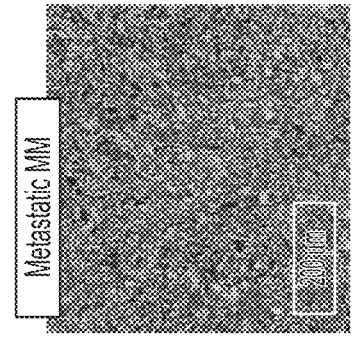
Figure 13B:
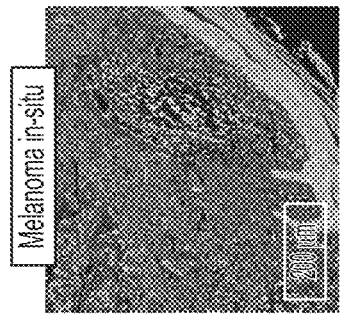
Figure 13F:
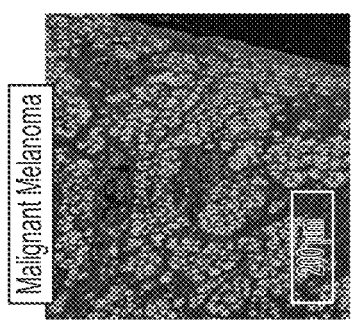
Figure 13A:
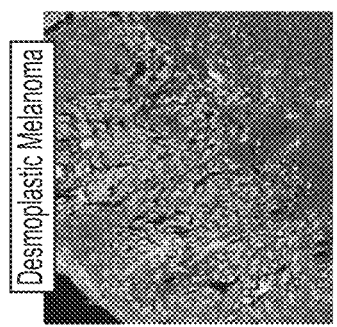
Figure 13E:
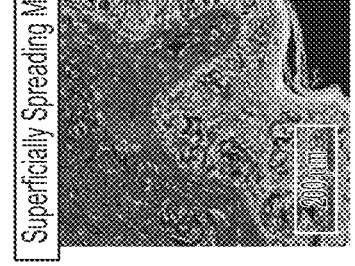
Figure 13D:
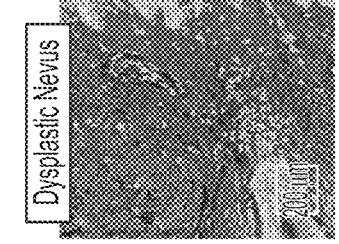
Figure 14A:
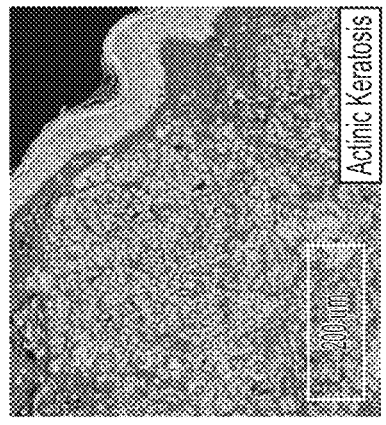
Figure 14B:
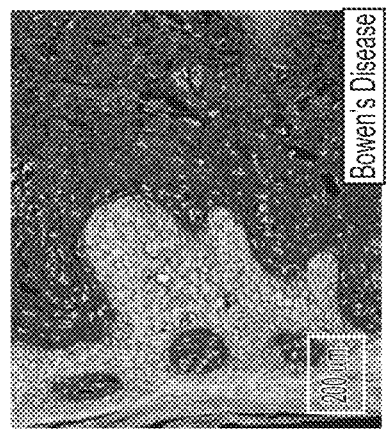
Figure 14C:
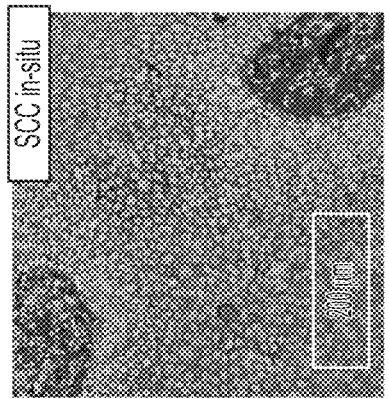
Figure 14D:
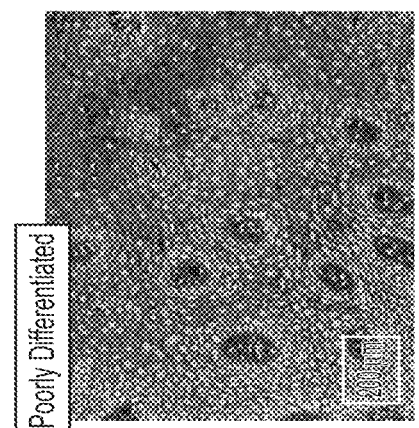
Figure 14E:
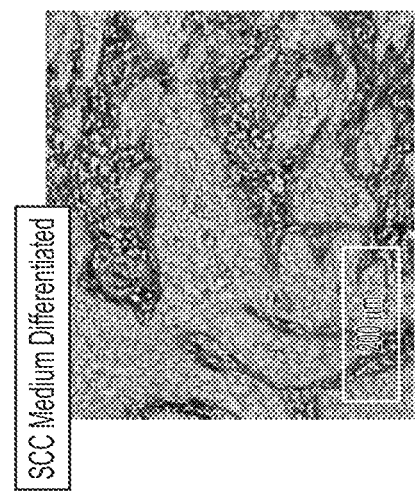
Figure 14F:
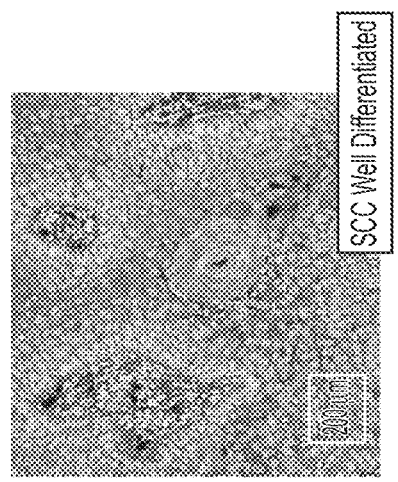
Figure 16A:
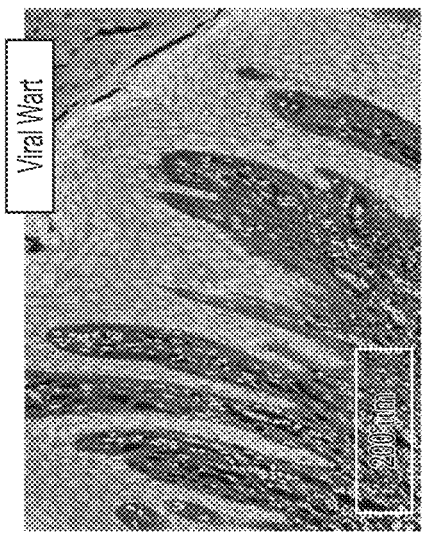
Figure 16B:
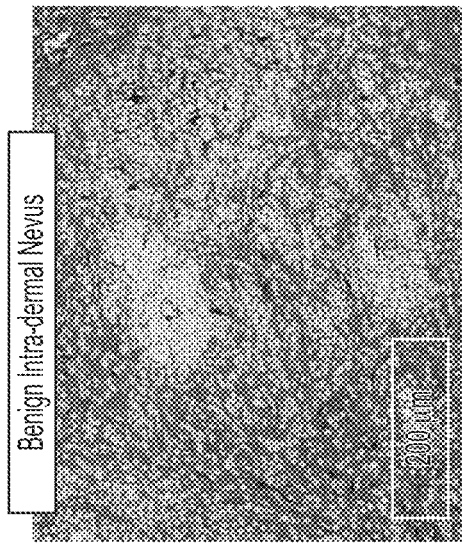
Figure 16C:
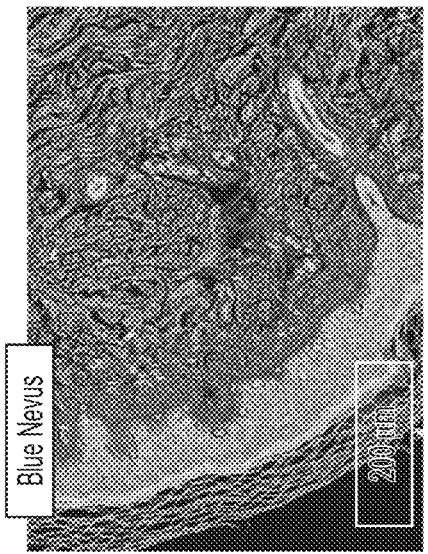
Figure 16D:

A patient presented with a slow growing, hyperkeratotic, painless lesion on her right lateral calf (FIG. 11D). Dermoscopic evaluation by a dermatologist suggested Bowen's disease. The area was biopsied with a 3 mm punch and sent for histopathological assessment. The biopsy showed a pleomorphic, multifocal dermal epithelioid lesion with mitotic figures and occasional apoptotic bodies. Scattered deposits of melanin pigment were noted at the margins of the dermal tumor lobules, where a brisk chronic inflammatory infiltrate was present. The initial histopathology working diagnosis was one of malignant melanoma. Immunohistochemical analysis was performed in order to confirm the diagnosis. In parallel, the slide was scanned and the digital image was analyzed by the present system/method, which diagnosed a poorly differentiated squamous cell carcinoma. An unusual immunoprofile was eventually returned, revealing admixed cell populations within the lesion: MNF116 immunopositive pleomorphic cells mingled with an abundant population of S100 and Melan A immunopositive cells with extensive dendritic processes. These features were those of a poorly differentiated squamous cell carcinoma, as diagnosed by the present system/method. The unusual presence of numerous colonizing dendritic melanocytes has however been responsible for the original impression of this being a melanocytic lesion.

As described in Examples 1-4, the system/method disclosed herein appears to provide a surprisingly accurate diagnostic result for mimics, subtle cases of diagnosis, and melanoma look-alike cases. FIG. 11D was difficult to be diagnosed by mere human histopathologist's eye but needed additional immunohistochemical (IHC) staining to resolve the subtlety in the diagnosis. By contrast, some embodiments of the present system could blind diagnose the cases accurately from the same images without additional IHC staining.

Example 6: Reference Diagnostic Scale for Various Cancers

The present example describes, among other things, obtaining diagnostic scores from various cancers, their respective subtypes, benign inflammations, and various normal healthy conditions, which can be used for a reference diagnostic scale.

The diagnostic scores listed in Tables 2-13 are derived from H&E tissue images of FIGS. 12A-19B. To obtain the diagnostic scores, first, cells in the images were identified. Each of the cells was segmented into the cellular area and the nuclear area. Then, the nuclear area feature and the nuclear contrast feature of each cell were calculated to obtain the information surface value for each cell, as described above. In Table 2, the diagnostic scores were derived from the specificity index and the junction curvature of the curve of $<C_L>$ vs L. In Tables 3-6, and 11-13, the diagnostic scores were calculated from the specificity index, the log thermal capacity and the junction coordinates that are values of L at the junctions of the curve of $<C>$ vs L. These diagnostic scores from known samples can be assigned to the reference diagnostic scale. The updated reference diagnostic scale incorporating the diagnostic scores in Tables 2-13 can provide accurate diagnosis for unknown samples regarding normality status, cancer type and/or cancer stage. For example, a calculated diagnostic score from an unknown sample can be mapped on the updated reference diagnostic scale which can provide details of the cancer. Each row of Tables 2-13 shows (i) the representative values of the diagnostic scores, specificity index and shape feature(s) from one sample and (ii) the reference scale range including the average and standard deviation of diagnostic scales from 200-1000 samples.

TABLE 2

| Diagnostic scores from FIGS. 12A-12F | | | | |
|---|---|---|---|---|
| Skin Diagnosis | Diagnostic Score (F1 = SI/JC) | Specificity Index (SI) | Shape Feature (Junction Curvature, JC) | Reference Scale Range |
| Merkel Cell Carcinoma | 1931 | 19.31 | 0.01 | 1801.7 ± 142.0 |

TABLE 2-continued

Diagnostic scores from FIGS. 12A-12F

| Skin Diagnosis | Diagnostic Score (F1 = SI/JC) | Specificity Index (SI) | Shape Feature (Junction Curvature, JC) | Reference Scale Range |
|---|---|---|---|---|
| Squamous Cell Carcinoma | 342 | 6.83 | 0.02 | 355.8 ± 26.9 |
| Poro-Carcinoma | 54 | 5.44 | 0.1 | 53.8 ± 1.5 |
| Basal Cell Carcinoma | 36 | 3.55 | 0.1 | 36.2 ± 3.3 |
| Malignant Melanoma | 29 | 1.43 | 0.05 | 28.2 ± 2.9 |
| Benign & Normal | −8 | −0.08 | 0.01 | −0.7 ± 0.8 |

TABLE 3

Diagnostic scores from FIGS. 13A-13G

| Melanoma Differential Diagnosis | Diagnostic Score $F2 = \dfrac{\Pi_i B_i \times C}{SI}$ | Specificity Index (SI) | Log Thermal Capacity (C) | Shape Feature (junction coordinate, $B_i$) | Ref-Scale Range |
|---|---|---|---|---|---|
| Superficially Spreading MM | 5707 | 0.58 | 749.57 | {1.2, 1.6, 2.3} | 5500 ± 253 |
| Desmoplastic Melanoma | 1359 | 1.28 | 724.69 | {1, 1.2, 2} | 1405 ± 54.6 |
| in-situ MM | 1300 | 1.67 | 602.93 | {1, 1.8, 2} | 1325 ± 25.2 |
| Malignant Melanoma | 1210 | 3.29 | 518.53 | {1.6, 2, 2.4} | 1240 ± 35.1 |
| Metastaic MM (Invasive) | 990 | 2.02 | 578.85 | {1.2, 1.6, 1.8} | 960 ± 32.5 |
| Lentigo Maligna (pre-invasive) | 435 | 3.65 | 472.71 | {1.2, 1.4, 2} | 440 ± 11.2 |
| Dysplastic Nevus (pre-malignant) | −2357 | −0.62 | 676.41 | {0.9, 1.2, 2} | −2000 ± 402.3 |

TABLE 4

Diagnostic scores from FIGS. 14A-14F

| SCC Differential Diagnosis | Sub-type/ Variant | Diagnostic Score $F2 = \dfrac{\Pi_i B_i \times C}{SI}$ | Specificity Index (SI) | Log Thermal Capacity (C) | Shape Feature (junction coordinate, $B_i$) | Ref-Scale Range |
|---|---|---|---|---|---|---|
| Bowen's Disease | Pre-invasive | 2510 | 1.01 | 718.51 | {1.2, 1.4, 2.1} | 2500 ± 240.2 |
| Poorly Differentiated SCC | High Grade | 1670 | 2.28 | 661.14 | {1.6, 1.8, 2} | 1700 ± 150.1 |
| in-situ SCC | In situ disease | 883 | 2.34 | 538.31 | {1.2, 1.6, 2} | 850 ± 75 |
| Actinic Keratosis | Pre-malignant | 586 | 2.33 | 542.24 | {1, 1.4, 1.8} | 605 ± 60.5 |
| Medium Differentiated SCC | Medium Grade | 328 | 3.76 | 467.53 | {1.1, 1.2, 2} | 325 ± 32.4 |
| Well Differentiated SCC | Low Grade | 160 | 8.91 | 338.46 | 1.2, 1.6, 2.2} | 150 ± 15.3 |

TABLE 5

Diagnosis scores of BCC from FIGS. 15A-15E

| BCC Differential Diagnosis | Diagnostic Score $F2 = \dfrac{\Pi_i B_i \times C}{SI}$ | Specificity Index (SI) | Log Thermal Capacity (C) | Shape Feature (junction coordinate, $B_i$) | Ref-Scale Range |
|---|---|---|---|---|---|
| Infiltrative BCC | 150 | 3.55 | 479.98 | {1.2, 1.6, 2.2} | 150 ± 12.5 |
| BCC | 211 | 4.72 | 437.16 | {1.4, 1.6, 2} | 210 ± 18.6 |
| Bowen's with | 536 | 3.88 | 464.21 | {1.4, 1.6, 2} | 530 ± 55.2 |
| Infiltrative BCC Nodular BCC | 1493 | 2.08 | 560.13 | {1.4, 1.8, 2.2} | 1500 ± 145.1 |
| Superficially Spreading BCC | 1898 | 1.32 | 662.96 | {1.2, 1.5, 2.1} | 1850 ± 175.4 |

TABLE 6

Diagnostic scores of skin Benign Nevus (Moles) and other varieties from FIGS. 16A-16D

| Skin Benign Varieties | Diagnostic Score $F2 = \dfrac{\Pi_i B_i \times C}{SI}$ | Specificity Index (SI) | Log Thermal Capacity (C) | Shape Feature (junction coordinate, $B_i$) | Ref-Scale Range |
|---|---|---|---|---|---|
| Blue Nevus | −46678 | −0.08 | 785.83 | {1.2, 1.8, 2.2} | −45500 ± 4150 |
| Viral wart | 8338 | 0.27 | 893.32 | {1, 1.4, 1.8} | 8200 ± 850 |
| Benign intra-dermal nevus | 670 | 2.09 | 416.12 | {1.1, 1.5, 1.8} | 655 ± 50.4 |
| Compound Nevus | 463 | 5.24 | 479.98 | {1.2, 1.6, 2.2} | 460 ± 45.6 |

TABLE 7

Figure 17A:
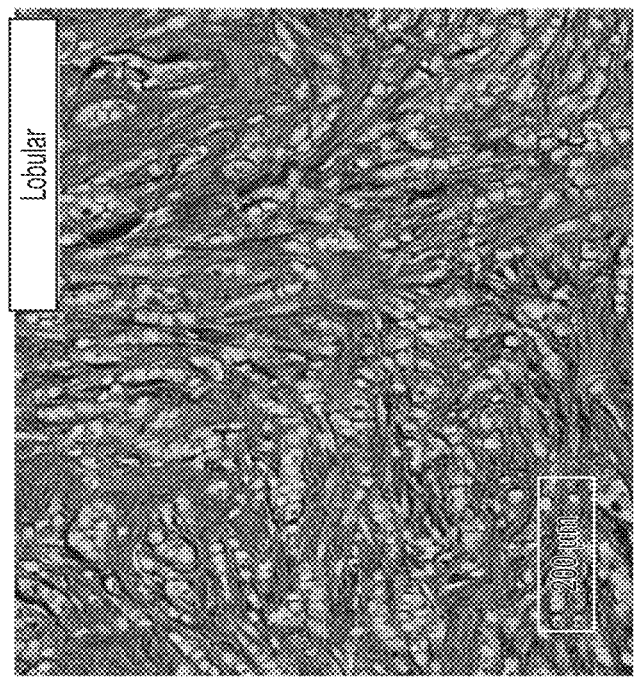
Figure 17B:
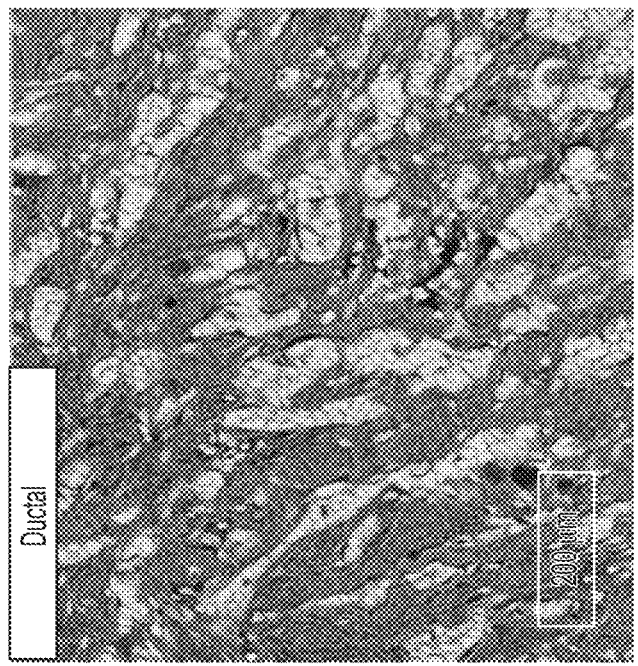

Diagnosis of breast cancer from FIGS. 17A-17B

| Breast Cancer Diagnosis | Diagnostic Score $F2 = \dfrac{\Pi_i B_i \times C}{SI}$ | Specificity Index (SI) | Log Thermal Capacity (C) | Shape Feature (junction coordinate, $B_i$) | Ref-Scale Range |
|---|---|---|---|---|---|
| Ductal | 619 | 2.37 | 265 | {0.8, 1.6, 2} | 600 ± 50.2 |
| Lobular | 377 | 7.32 | 59 | {1.8, 2, 2.2} | 375 ± 70.1 |

Table 7 includes diagnostic indexes of breast cancers. This result shows the diagnostic capability of the present system/method beyond skin cancer, to cancer of other tissue origins such as breast and confirms the universal nature of the underlying diagnostic methods and variables.

TABLE 8

Figure 18C:
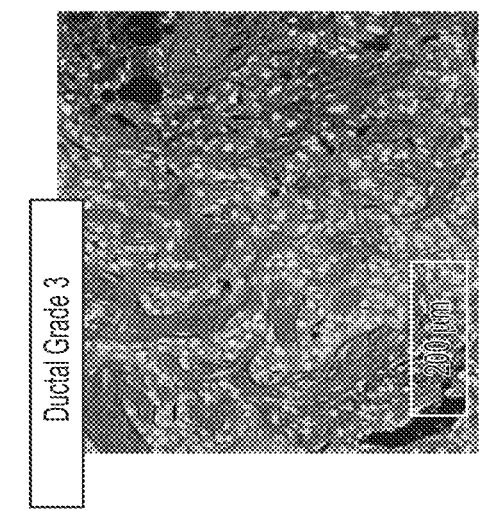
FIG. 18A-18C depict ductal breast cancer with different grades.
Figure 18B:
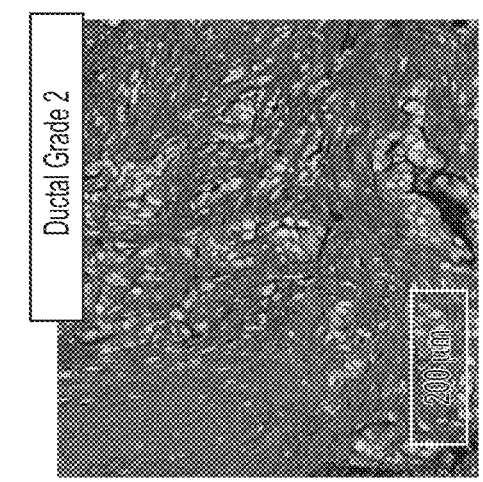
Figure 18A:
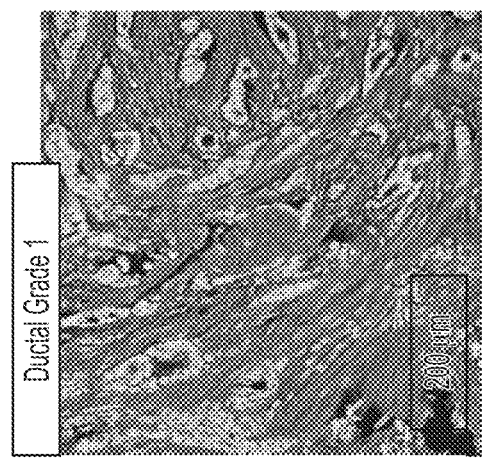

Diagnostic scores of breast cancer grading (Ductal) from FIGS. 18A-18C

| Ductal Cancer Grading | Diagnostic Score $F2 = \dfrac{\Pi_i B_i \times C}{SI}$ | Specificity Index (SI) | Log Thermal Capacity (C) | Shape Feature (junction coordinate, $B_i$) | Ref-Scale Range |
|---|---|---|---|---|---|
| Grade 1 | 627.2 | 1.78 | 364 | {1.4, 1.8, 2.2} | 620 ± 12.5 |
| Grade 2 | 654.3 | 1.58 | 418 | {1.2, 1.8, 2} | 650 ± 15.2 |
| Grade 3 | 670.6 | 1.7 | 398 | {1.2, 1.6, 2} | 675 ± 9.5 |

TABLE 9

Figure 19B:
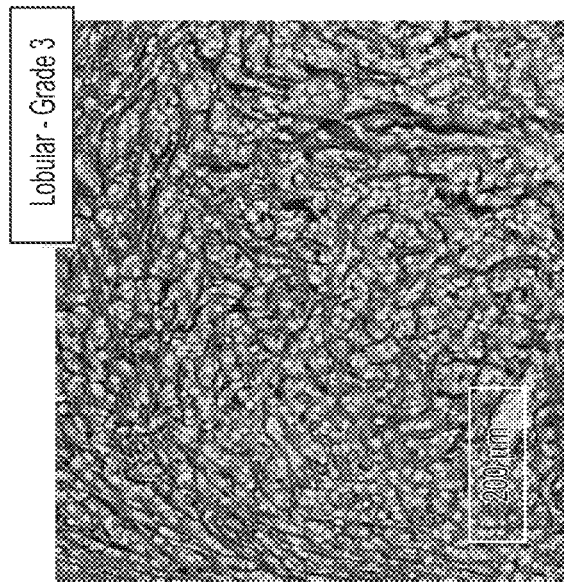
Figure 19A:
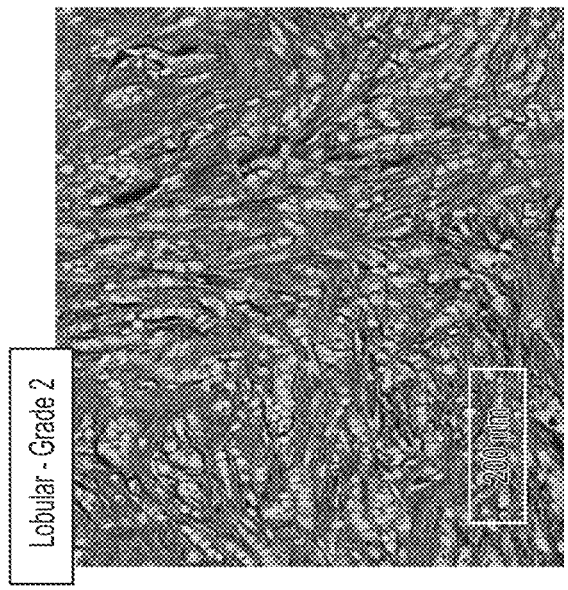

Diagnostic scores of breast cancer grading (Lobular) from FIGS. 19A-19B

| Lobular Cancer Grading | Diagnostic Score $F2 = \dfrac{\Pi_i B_i \times C}{SI}$ | Specificity Index (SI) | Log Thermal Capacity (C) | Shape Feature (junction coordinate, $B_i$) | Ref-Scale Range |
|---|---|---|---|---|---|
| Grade 2 | 371.7 | 7.45 | 53 | {1.2, 1.5, 2} | 370 ± 65.3 |
| Grade 3 | 468.4 | 4.22 | 113 | {1, 1.2, 1.8} | 445 ± 40.4 |

Tables 9 and 10 include diagnostic scores of grading breast cancers. Breast cancer grading protocol is typically less efficient and diagnosed inconsistently by different pathologists. The diagnostic ability of breast cancer grading of the present system/method directly from the digital image of biopsy slides without any additional staining protocol has advantages in the disease prognosis and efficacy of the available therapeutics.

Example 7: IR Images of Dummy Cells

The present example describes, among other things, obtaining IR images from cell mimicking objects, and calculation of information surfaces from the images as shown in FIGS. 32A-32C and 33A-33C.

Each source was a blackbody emitting thermal IR radiation from concentric inner and outer circular disk held at two different temperature T2 and T1 (T2>T1). Each individual 'cell equivalent IR source' was fabricated from a blackbody material and consisted of two concentric disks (one large and one small diameter) machined from treated birch wood with the smaller disk (3 mm thick) placed concentrically on top of the bigger disk (6 mm thick). Two disks were kept thermally insulated from each other using three alternate thin layers of rock wool and polystyrene placed in between them. Two disks were individually heated at two different surface temperatures by keeping them in contact with two individual heat reservoir (heated copper plate between 30-50° C.) equilibrated with the ambient environment. Alternatively, electrically heated (around 800° C.) two silicon carbide concentric disk insulated from each other by ceramic fiber wool were also tested and gave similar results. Each of the cell equivalent IR sources consisted of an inner 'small' source (brighter disk) at a higher temperature (T2) and an outer 'big' source (dimmer annular ring) with a lower temperature (T1). In FIG. 32A, the small brighter disk of the cell equivalent source has a diameter (R2) of 1.2 mm and temperature (T2) of 38° C. The big dimmer disk has a diameter (R1) of 2.5 mm, and temperature (T1) of 37° C. FIG. 33A has two cell equivalent sources. The big cell equivalent sources (left) has R1=10 mm, T1=37-38° C., R2=5 mm, T2=38-40° C., and the small cell equivalent sources (right) has R1=5 mm, T1=37-38° C., R2=2.5 mm, T2=38-40° C.

The IR images of the disk sources shown here were taken with a calibrated 2-D uncooled Vanadium Oxide IR detector (DRS Infrared) with 640×480 pixel resolution (pixel size 17 µm) and sensitivity NEdT <50 mK, using a 25.4 mm diameter ZnSe lens (f=50.8 mm) and a focusing ZnSe lens (f=9mm, f1.4) to focus the image on the detector.

The output voltage signal $S(\lambda)$ from each pixel of the 2D detector represents the intensity I (i.e., photon energy flux N (E)) of the emitted signal from the cell equivalent IR sources. The intensity I was integrated over a broad band of emitted signal wavelength λ (e.g., λ=8-14 µm). The optical system (e.g., lens or reflective objective) formed an image on the 2D spatial array of detector pixel because of the difference of IR photon flux signal $S(\lambda)$ measured by individual pixel emitted from different parts of the object differing in temp.

These cell equivalent IR sources images were used to calculate ensemble averaged thermodynamic and metabolic information. The images and their corresponding measurement of spatial and energy thermodynamic signal show that the device is capable of imaging a single or collection of spatially separated individual cell equivalent IR sources. Such signals measured experimentally by the device from the cell equivalent IR sources are used for obtaining thermal contours and corresponding points in the feature planes. Such points in the feature plane can compute a diagnostic index, thereby determining the normality status of such system.

Example 8: IR Images of Live Cells

The present example describes, among other things, obtaining IR images from live cells by devices as described in the present application.

Figure 35A:
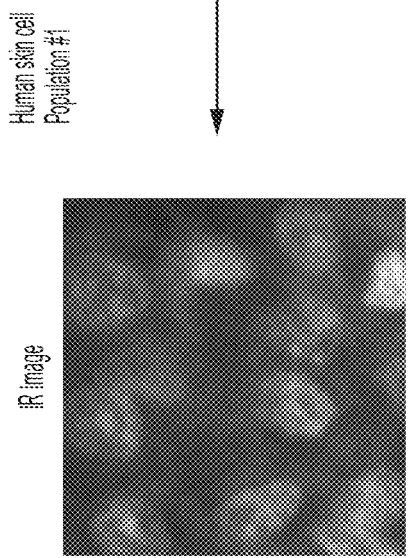
FIGS. 35A and 36A show IR images of multiple biological cells. The images were obtained from a calibrated 2-D uncooled vanadium oxide IR detector coupled with a reflective optical system.
Figure 35B:
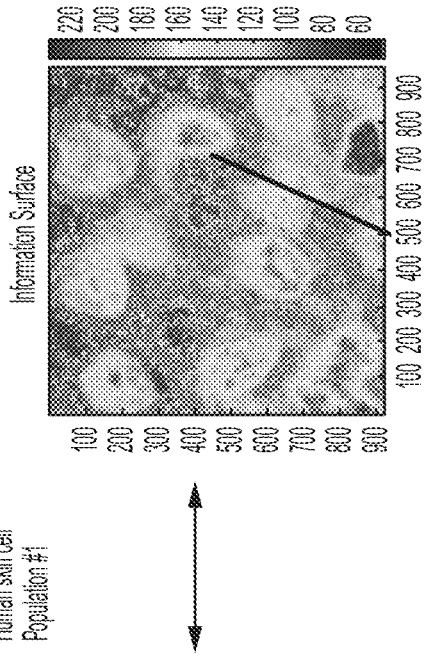
Figure 35C:
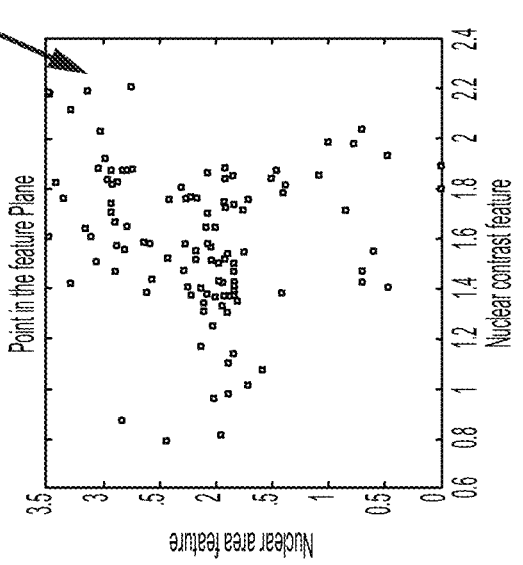
Figure 36A:
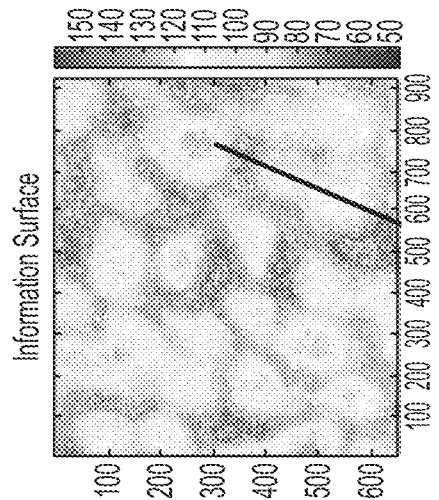
Figure 36B:
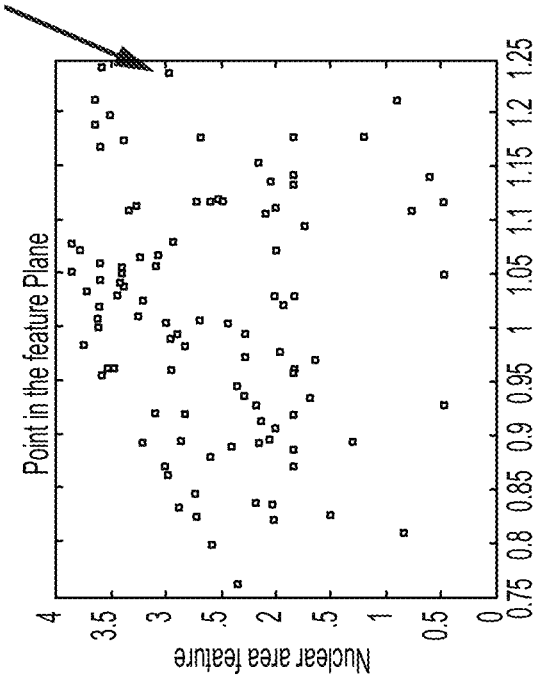
Figure 36C:
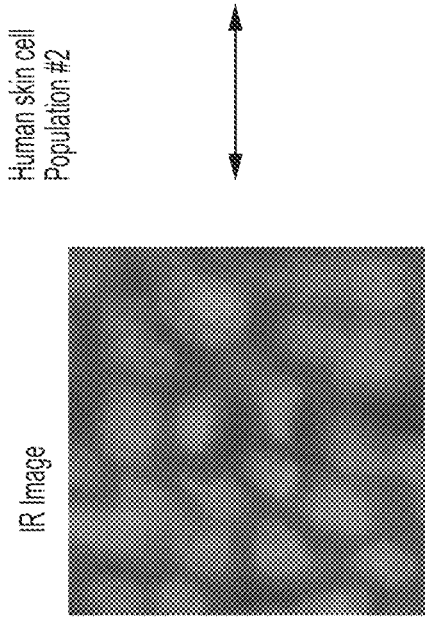

FIG. 34A depicts a single biological cell, and FIGS. 35A and 36A do multiple live biological cells (e.g., tissue) imaged by the IR optical system comprising a vanadium oxide detector (as described in FIGS. 1 and 2). The cells in FIGS. 34A, 35A and 36A show temperature differences between their nucleus and cytoplasm. The nucleus and cytoplasm in each cell may have behaved as a blackbody emitting thermal IR radiation at two different temperatures.

The tissue samples were collected and spread on a black slide (made from saline coated black anodized aluminum). The imaging system comprised a calibrated 2-D uncooled Vanadium Oxide IR detector with 640×480 pixel resolution and sensitivity of NEdT <50 mK, and a 36X Schwartzschild Cassegranian reflective IR objective (numerical aperture NA 0.5). To focus the IR radiation from the sample on the detector, a mirror and/or a focusing ZnSe lens (f=9 mm) was used. The output voltage signal $S(\lambda)$ from each pixel of the 2-D detector was an integration of the intensity I (i.e., photon energy flux N(E)) of the emitted IR signal from the cells over a broad band of emitted signal wavelength λ (e.g., λ=8-14 µm).

$$S(\lambda) = \int I(\lambda) d\lambda = \int N(E) dE \qquad (11)$$

The optical system created an image on the 2-D spatial array of detector pixel. IR photon flux signal S(k) measured by individual pixel emitted from the different parts of the object had different temperatures. The detector output voltage signals $S(\lambda)_{m,n}$ (m=1 . . . 640, n=1 . . . 480) from each detector pixel were fed to a signal processing board comprising an FPGA controller. The FPGA controller was connected (through Camera Link cable) to a PCIe Express frame grabber card (Imperx VCE-CLPCIe0) installed in a computer running FrameLink Express software (or/and software written in C++ using FrameLink SDK). The software saved the detector image as monochrome jpeg (or optionally as raw or bmp) format.

As shown in FIGS. 34A, 35A, and 36A, the optical device exemplified herein is capable of imaging a single or multiple spatially-separated biological cell(s) with temperature gradients in the nuclear and/or cellular area(s). The thermal and thermodynamic diagnostic parameters including the diagnostic scores were successfully calculated from the images obtained by the device. The present example confirms that the methods described herein also can diagnose the normality status of cells from IR images.

Example 9: Calibration of IR Imaging Device

The present example describes the calibration of an imaging system comprising a calibrated 2-D uncooled Vanadium Oxide IR detector (DRS Infrared) with 640×480 pixel resolution and sensitivity of NEdT <50mK, and a 15× Schwartzschild Cassegranian reflective IR objective (numerical aperture NA 0.58).

Figure 37A:
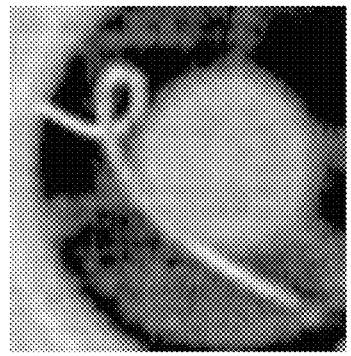
FIGS. 37A-37F are IR images obtained from an exemplary IR imaging device, according to illustrative embodiments of the present invention.
Figure 37B:
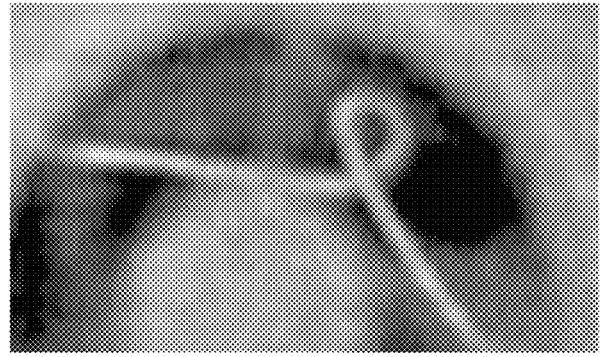
Figure 37C:
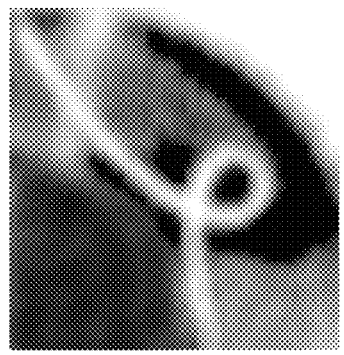
Figure 37D:
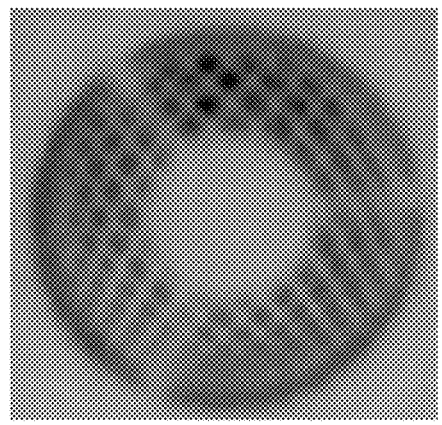
Figure 37E:
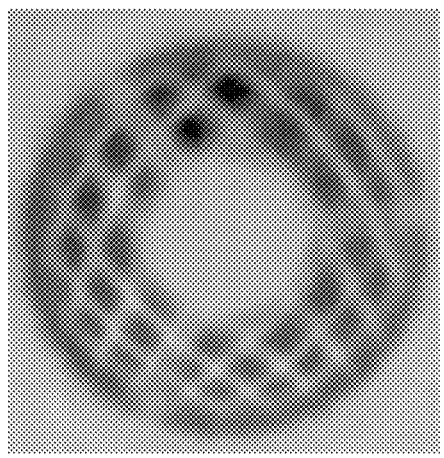
Figure 37F:
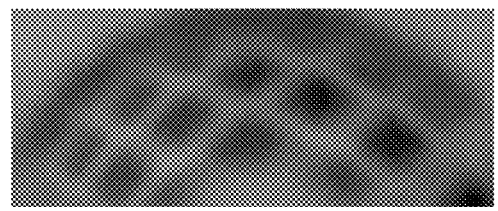

To calibrate the IR imaging device, various home-made micron-scale objects (e.g., metal wire, metal wire loop, silver XY micromesh) were used as shown in FIGS. 37A-37F. In FIGS. 37A-37C, three different types of wires were used to form the loops. FIG. 37A is an IR image of the loop made from a copper wire with a diameter of 561 µm. FIG. 37B is an IR image of the loop made from a bronze wire with a diameter of 222 µm. FIG. 37C is an IR image of the loop made from a copper wire with a diameter of 160 µm. The diameter of each loop was about the twice the diameter of the wire. FIGS. 37D-37F depict the IR grid (or IR cross hair) made from micron-scale silver mesh (e.g., a mesh with a diameter of 270 µm and an opening size of 1580 µm) with various magnifications. The sizes of the metal wires (bronze and copper), the wire loops and the silver micromesh were measured using a 1951 USAF Resolution Targets (Thorlabs R3L3S1P positive pattern) under an inverted optical microscope. The IR images were taken at room temperature (with or without frictional heating from hands) utilizing the optical magnification system and the uncooled vanadium oxide IR detector. The magnified 2-D images recorded IR emitted from the wires or meshes. This exemplary IR imaging device setup had the resolution of 160 µm. The IR objectives used in this example appear to absorb a negligible amount of visible light and IR irradiation.

What is claimed is:

1. A method comprising:
   receiving, by a processor, data representing at least one cell that has been identified in an area of an image and segmented into a nuclear area and a cellular area;
   calculating, by the processor for the at least one cell and based at least in part on the data, a plurality of information surface values each derived as a function of both:
      (i) a nuclear contrast feature, wherein the nuclear contrast feature comprises a temperature difference between the nuclear area and the cellular area; and
      (ii) a nuclear area feature, wherein the nuclear area feature comprises a ratio of the nuclear area to a nuclear volume projection;
   calculating, by the processor, a diagnostic score based at least in part on the plurality of information surface values; and
   determining, by the processor based at least in part on the diagnostic score, a normality status of the area of the image.

2. The method of claim 1, wherein determining the normality status based at least in part on the diagnostic score comprises comparing the diagnostic score with a reference scale.

3. The method of claim 1, wherein calculating the diagnostic score further comprises calculating a specificity index by:
   calculating an ensemble average of local specific heats for each of subpopulations of cells within the area of the image; and
   integrating the ensemble average of the local specific heats over cell cycle stages or intrinsic cell cycle time.

4. The method of claim 1, wherein calculating the diagnostic score further comprises calculating a log thermal capacity by integrating logarithm of local specific heats for each of subpopulations of cells.

5. The method of claim 1, wherein the normality status indicates a presence, in the area of the image, of one or more of a cancer and one or more of stages of the cancer.

6. The method of claim 1, further comprising:
   comparing the normality score of the area with a second normality score associated with a second area adjacent to the area; and
   identifying, based on the comparison, the existence of a cancer boundary between the area and the second area.

7. The method of claim 1, wherein the area of the image is associated with a biological fluid sample.

8. The method of claim 1, wherein the area of the image corresponds to at least a portion of a hematoxylin and eosin ("H&E") stain sample.

9. The method of claim 1, further comprising monitoring, by the processor based at least in part on the normality status, trafficking and localization of one or more cell types.

10. The method of claim 1, wherein the normality status indicates a presence, in the area of the image, of one or more of inflammation, vascular disease, cell death, injury, apoptosis, necrosis, hypoxia, and angiogenesis.

11. A system comprising: a processor;
   a memory having instructions stored thereon, wherein the instructions, when executed by the processor, cause the processor to perform operations comprising:
   receiving, by a processor, data representing at least one cell that has been identified in an area of an image and segmented into a nuclear area and a cellular area;
   calculating, by the processor for the at least one cell and based at least in part on the data, a plurality of information surface values each derived as a function of both:
      (i) a nuclear contrast feature, wherein the nuclear contrast feature comprises a temperature difference between the nuclear area and the cellular area; and
      (ii) a nuclear area feature, wherein the nuclear area feature comprises a ratio of the nuclear area to a nuclear volume projection;
   calculating, by the processor, a diagnostic score based at least in part on the plurality of information surface values; and
   determining, by the processor based at least in part on the diagnostic score, a normality status of the area of the image.

12. The system of claim 11, wherein determining the normality status based at least in part on the diagnostic score comprises comparing the diagnostic score with a reference scale.

13. The system of claim 11, wherein calculating the diagnostic score further comprises calculating a specificity index by:

calculating an ensemble average of local specific heats for each of subpopulations of cells within the area of the image; and integrating the ensemble average of the local specific heats over cell cycle stages or intrinsic cell cycle time.

14. The system of claim 11, wherein calculating the diagnostic score further comprises calculating a log thermal capacity by integrating logarithm of local specific heats for each of subpopulations of cells.

15. The system of claim 11, wherein the instructions, when executed by the processor, cause the processor to perform operations further comprising determining, based at least in part on the normality status, one or more of a presence of cancer in the area of the image, and one or more of stages of cancer associated with the area of the image.

16. The system of claim 11, wherein the instructions, when executed by the processor, cause the processor to perform operations further comprising:

comparing the normality score of the area with a second normality score associated with a second area adjacent to the area; and identifying, based on the comparison, the existence of a cancer boundary between the area and the second area.

17. The system of claim 11, wherein the area of the image is associated with a biological fluid sample.

18. The system of claim 11, wherein the area of the image corresponds to at least a portion of a hematoxylin and eosin ("H&E") stain sample.

19. The system of claim 11, further comprising monitoring, by the processor based at least in part on the normality status, trafficking and localization of one or more cell types.

20. The system of claim 11, wherein the normality status indicates a presence, in the area of the image, of one or more of inflammation, vascular disease, cell death, injury, apoptosis, necrosis, hypoxia, and angiogenesis.

21. The method of claim 1, wherein the nuclear contrast feature is generated by operations comprising:

determining, for a cell of the at least one cell, temperature data characterizing a temperature of the nuclear area of the cell;

determining, for the cell of the one or more cells, temperature data characterizing a temperature of the cellular area of the cell; and determining the nuclear contrast feature based at least in part on a difference between: (a) the temperature data characterizing the nuclear area of the cell, and (b) the temperature data characterizing the cellular area of the cell.

* * * * *